US012741098B2

(12) United States Patent
Ulla

(10) Patent No.: US 12,741,098 B2
(45) **Date of Patent: *Sep. 22, 2026**

(54) DEVICES AND METHODS FOR PRECISION DOSE DELIVERY

(71) Applicant: Regeneron Pharmaceuticals, Inc., Tarrytown, NY (US)

(72) Inventor: Sibgat Ulla, Rensselaer, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/872,959

(22) Filed: Jul. 25, 2022

(65) Prior Publication Data

US 2022/0355040 A1 Nov. 10, 2022

Related U.S. Application Data

(63) Continuation of application No. 17/218,875, filed on Mar. 31, 2021, now Pat. No. 11,433,186, and a (Continued)

(51) Int. Cl.
*A61M 5/315* (2006.01)

(52) U.S. Cl.
CPC .... *A61M 5/31536* (2013.01); *A61M 5/31511* (2013.01); *A61M 5/31583* (2013.01); *A61M 5/31593* (2013.01)

(58) Field of Classification Search
CPC ........... A61M 2005/31508; A61M 2005/1787; A61M 5/31501; A61M 5/31505; A61M 5/31595; A61M 5/31506; A61M 5/31536
See application file for complete search history.

(56) References Cited

U.S. PATENT DOCUMENTS 2,129,675 A 9/1938 Cole
2,375,711 A 5/1945 Joseph
(Continued)

FOREIGN PATENT DOCUMENTS

AU 54957/69 11/1970
AU 40517/85 A 10/1985
(Continued)

OTHER PUBLICATIONS

Decision of Patent Grant in Korean Application No. 10-2020-7019695, dated Aug. 11, 2023, 4 pages (in Korean with English translation).

(Continued)

*Primary Examiner* — Emily L Schmidt
(74) *Attorney, Agent, or Firm* — Bookoff McAndrews, PLLC

(57) ABSTRACT

Disclosed herein are delivery devices for delivering a volume of a drug product, placebo product, or other product including a fluid. The devices may include a barrel having a longitudinal axis, a proximal end region, and a distal end region. The proximal end region may include an opening, and the barrel may be configured to receive a drug therein. A plunger rod may be disposed at least partially inside the barrel and protruding from the opening. The plunger rod may include a rack having a plurality of teeth. The device may further include a pinion having a plurality of teeth configured to engage with the plurality of teeth of the rack, and rotation of the pinion against the rack may move at least a part of the plunger rod along the longitudinal axis of the barrel.

20 Claims, 30 Drawing Sheets

Related U.S. Application Data continuation of application No. 17/517,464, filed on Nov. 2, 2021, said application No. 17/218,875 is a continuation of application No. 16/900,747, filed on Jun. 12, 2020, now abandoned, said application No. 17/517,464 is a continuation of application No. 16/900,747, filed on Jun. 12, 2020, now abandoned, which is a continuation of application No. PCT/US2018/065192, filed on Dec. 12, 2018.

(60) Provisional application No. 62/722,252, filed on Aug. 24, 2018, provisional application No. 62/676,047, filed on May 24, 2018, provisional application No. 62/598,212, filed on Dec. 13, 2017.

(56) References Cited

U.S. PATENT DOCUMENTS 2,739,590 A 3/1956 Yochem
2,792,834 A 5/1957 Leon
3,122,280 A 2/1964 Goda
3,128,765 A 4/1964 Tint
3,236,423 A 2/1966 Marbach et al.
3,236,434 A 2/1966 Taddeau
3,337,095 A 8/1967 Marbach et al.
3,608,550 A 9/1971 Stawski
3,610,241 A 10/1971 Lemarie
3,797,487 A 3/1974 Schmidt
3,934,586 A 1/1976 Easton et al.
3,965,945 A 6/1976 Ross
4,117,728 A 10/1978 Johnson
4,152,939 A 5/1979 Renshaw
4,357,971 A 11/1982 Friedman
4,391,272 A 7/1983 Staempfli
4,444,335 A 4/1984 Wood et al.
4,475,905 A 10/1984 Himmelstrup
4,654,035 A 3/1987 Ando
4,840,616 A 6/1989 Banks
4,852,768 A 8/1989 Bartsch
4,871,094 A 10/1989 Gall et al.
4,915,692 A 4/1990 Verlier
4,915,695 A 4/1990 Koobs
5,009,645 A 4/1991 Silver et al.
5,080,649 A 1/1992 Vetter
5,084,017 A 1/1992 Maffetone
RE33,821 E 2/1992 Banks
5,092,842 A 3/1992 Bechtold et al.
5,114,406 A 5/1992 Gabriel et al.
5,284,132 A 2/1994 Geier
5,295,976 A 3/1994 Harris
5,318,544 A 6/1994 Drypen et al.
5,358,497 A 10/1994 Dorsey et al.
5,364,374 A 11/1994 Morrison et al.
5,370,620 A 12/1994 Shonfeld
5,380,295 A 1/1995 Vacca
5,439,643 A 8/1995 Liebert
5,485,853 A 1/1996 Stubbs
5,507,727 A 4/1996 Crainich
5,533,970 A 7/1996 Berger et al.
5,545,147 A 8/1996 Harris
5,554,122 A 9/1996 Emanuel
5,593,391 A 1/1997 Stanners
5,688,251 A 11/1997 Chanoch
5,700,247 A 12/1997 Grimard et al.
5,795,337 A 8/1998 Grimard
5,801,156 A 9/1998 Robinson et al.
5,807,343 A 9/1998 Tucker et al.
5,807,345 A 9/1998 Grabenkort
5,820,603 A 10/1998 Tucker et al.
5,827,233 A 10/1998 Futagawa et al.
5,833,669 A 11/1998 Wyrick
5,834,313 A 11/1998 Lin
5,843,034 A 12/1998 Redfern et al.
5,904,897 A 5/1999 Kendall et al.
5,911,950 A 6/1999 Chen et al.
5,919,418 A 7/1999 Kendall et al.
5,925,316 A 7/1999 Kendall et al.
5,951,526 A 9/1999 Korisch et al.
5,961,495 A 10/1999 Walters et al.
5,961,921 A 10/1999 Addy et al.
5,971,956 A 10/1999 Epstein
5,976,113 A 11/1999 Morigi et al.
5,980,487 A 11/1999 Jones et al.
5,980,825 A 11/1999 Addy et al.
5,988,452 A 11/1999 Dent et al.
6,030,579 A 2/2000 Addy et al.
6,042,571 A 3/2000 Hjertman et al.
6,066,294 A 5/2000 Lin et al.
6,068,817 A 5/2000 Addy et al.
6,077,480 A 6/2000 Edwards et al.
6,096,010 A 8/2000 Walters et al.
6,096,266 A 8/2000 Duroselle
6,120,730 A 9/2000 Palaniappan et al.
6,126,640 A 10/2000 Tucker et al.
6,132,679 A 10/2000 Conviser
6,132,680 A 10/2000 Addy et al.
6,142,976 A 11/2000 Kubo
6,142,977 A 11/2000 Kolberg et al.
6,164,044 A 12/2000 Porfano et al.
6,174,502 B1 1/2001 Addy et al.
6,187,265 B1 2/2001 Wu et al.
6,189,195 B1 2/2001 Reilly et al.
6,189,292 B1 2/2001 Odell et al.
6,193,931 B1 2/2001 Lin et al.
6,203,756 B1 3/2001 Lin et al.
6,224,828 B1 5/2001 Lin et al.
6,228,324 B1 5/2001 Hasegawa et al.
6,250,052 B1 6/2001 Porfano et al.
6,263,641 B1 7/2001 Odell et al.
6,264,629 B1 7/2001 Landau
6,273,152 B1 8/2001 Buehler et al.
6,279,622 B1 8/2001 Nguyen et al.
6,319,235 B1 11/2001 Yoshino
6,319,480 B1 11/2001 Addy et al.
6,325,972 B1 12/2001 Jacobs et al.
6,349,850 B1 2/2002 Cheikh
6,378,526 B1 4/2002 Bowman et al.
6,390,155 B1 5/2002 Nguyen
6,391,008 B1 5/2002 Tsai
6,394,111 B1 5/2002 Jacobs et al.
6,397,849 B1 6/2002 Bowman et al.
6,398,762 B1 6/2002 Vetter et al.
6,406,666 B1 6/2002 Cicha et al.
6,419,656 B1 7/2002 Vetter et al.
6,450,993 B1 9/2002 Lin
6,451,254 B1 9/2002 Wang et al.
6,451,255 B1 9/2002 Williams et al.
6,451,272 B1 9/2002 Fryer et al.
6,454,874 B1 9/2002 Jacobs et al.
6,491,881 B2 12/2002 Fryer et al.
6,494,964 B1 12/2002 Jacobs et al.
6,495,100 B1 12/2002 Lin et al.
6,511,457 B2 1/2003 Thompson
D470,234 S 2/2003 Mahurkar
6,516,817 B2 2/2003 Jacobs et al.
6,516,818 B2 2/2003 Jacobs et al.
6,528,015 B1 3/2003 Lin et al.
6,528,016 B1 3/2003 Kohler et al.
6,528,017 B2 3/2003 Jacobs et al.
6,530,399 B2 3/2003 Nguyen et al.
6,530,906 B2 3/2003 Hu
6,562,006 B1 5/2003 Hjertman et al.
6,589,481 B1 7/2003 Lin et al.
6,627,150 B1 9/2003 Wang et al.
6,645,429 B1 11/2003 Raniwala
6,656,426 B1 12/2003 Wang et al.
6,656,427 B2 12/2003 Lin et al.
6,673,313 B2 1/2004 Wang et al.
6,682,696 B1 1/2004 Bjerborn
D489,819 S 5/2004 Ford
6,734,405 B2 5/2004 Centanni et al.
6,746,647 B2 6/2004 Kohler et al.
6,746,652 B2 6/2004 Khorzad et al.
6,790,410 B2 9/2004 Metzner et al.

(56) References Cited

U.S. PATENT DOCUMENTS 6,792,743 B2 9/2004 Odell et al.
6,807,797 B2 10/2004 Forsberg et al.
6,808,681 B2 10/2004 Bjerborn
6,815,206 B2 11/2004 Lin et al.
6,852,279 B2 2/2005 Williams et al.
6,906,296 B2 6/2005 Centanni et al.
6,942,638 B1 9/2005 Quinn
6,945,962 B2 9/2005 Koenig et al.
6,967,315 B2 11/2005 Centanni et al.
6,977,061 B2 12/2005 Lin et al.
6,996,952 B2 2/2006 Gupta et al.
7,014,813 B1 3/2006 Watling et al.
7,040,485 B2 5/2006 Gupta et al.
7,048,887 B2 5/2006 Frost et al.
7,108,832 B2 9/2006 Christensen et al.
7,146,746 B2 12/2006 Kawasaki
7,169,133 B2 1/2007 Broennimann et al.
7,179,419 B2 2/2007 Lin et al.
7,201,869 B2 4/2007 Williams et al.
D543,625 S 5/2007 Numata et al.
7,229,590 B2 6/2007 Awakowicz et al.
7,229,591 B2 6/2007 Wu et al.
7,246,627 B2 7/2007 Jacobs et al.
7,252,800 B2 8/2007 Jacobs et al.
7,267,806 B2 9/2007 Kendall et al.
7,273,594 B2 9/2007 Lin et al.
7,285,254 B2 10/2007 Lin et al.
7,294,305 B2 11/2007 Lin et al.
7,303,748 B2 12/2007 Wiegand et al.
7,329,241 B2 2/2008 Horvath et al.
7,354,581 B2 4/2008 Cedarbaum et al.
7,396,347 B2 7/2008 Hjertman et al.
7,407,494 B2 8/2008 Boström et al.
7,452,504 B2 11/2008 Wu et al.
7,459,133 B2 12/2008 Swank
7,468,159 B2 12/2008 Lin et al.
7,481,974 B2 1/2009 Sizer
7,491,371 B2 2/2009 Moller et al.
7,517,334 B2 4/2009 Jacobs et al.
7,531,172 B2 5/2009 Stahl et al.
7,531,173 B2 5/2009 Wiegand et al.
7,534,233 B2 5/2009 Schiller et al.
7,553,486 B2 6/2009 Finger
7,556,767 B2 7/2009 Lin et al.
7,564,983 B2 7/2009 Ibuka et al.
7,569,180 B2 8/2009 Kohler et al.
7,575,716 B2 8/2009 Wu et al.
7,582,257 B2 9/2009 Bedard et al.
7,604,773 B2 10/2009 Ekstrom et al.
7,608,218 B2 10/2009 Fryer et al.
7,611,495 B1 11/2009 Gianturco
7,638,090 B2 12/2009 Hyde et al.
7,640,782 B2 1/2010 Hill
7,645,267 B2 1/2010 Vetter et al.
7,666,369 B2 2/2010 Bondar
7,670,550 B2 3/2010 Lin et al.
7,704,237 B2 4/2010 Fisher et al.
7,704,238 B2 4/2010 Diller et al.
7,704,426 B2 4/2010 Earhart et al.
7,713,473 B2 5/2010 Kendall et al.
7,727,195 B2 6/2010 Norton
7,727,201 B2 6/2010 Kirchhofer
7,727,464 B2 6/2010 Frost
7,749,200 B2 7/2010 Graf et al.
7,754,156 B2 7/2010 Hyde et al.
7,803,316 B2 9/2010 Lin et al.
7,807,100 B2 10/2010 Choperena et al.
7,807,164 B2 10/2010 Furfine et al.
7,811,263 B2 10/2010 Burren et al.
7,824,610 B2 11/2010 Ko
7,850,906 B2 12/2010 Watling et al.
D631,153 S 1/2011 McGlothlin et al.
7,880,887 B2 2/2011 Olson et al.
7,892,486 B2 2/2011 Mizuno et al.
7,910,055 B2 3/2011 Bondar
7,918,824 B2 4/2011 Bishop et al.
7,954,521 B2 6/2011 Py et al.
7,954,672 B2 6/2011 Keller
7,976,506 B2 7/2011 Vitullo et al.
7,981,361 B2 7/2011 Bacik
8,017,074 B2 9/2011 Arnold et al.
8,029,725 B2 10/2011 Olsson et al.
8,034,288 B2 10/2011 Burns et al.
8,039,022 B2 10/2011 Minamikawa et al.
8,062,590 B1 11/2011 Ricciardi et al.
8,071,021 B2 12/2011 Hill
8,075,533 B2 12/2011 Lee
8,075,547 B2 12/2011 Lee
8,105,293 B2 1/2012 Pickhard
8,110,156 B2 2/2012 Ricciardi et al.
8,114,342 B2 2/2012 Jung et al.
8,118,788 B2 2/2012 Frezza
8,124,127 B2 2/2012 Faucher et al.
8,132,600 B2 3/2012 Py et al.
8,147,752 B2 4/2012 Iwashita et al.
8,147,771 B2 4/2012 Yokoi et al.
8,163,234 B2 4/2012 Fedegari
8,178,042 B2 5/2012 Jung et al.
8,187,597 B2 5/2012 Shima et al.
8,196,741 B2 6/2012 Finke et al.
8,205,416 B2 6/2012 Hansen
8,216,575 B2 7/2012 Yu
8,221,679 B2 7/2012 Golkowski
8,230,616 B2 7/2012 McLaren et al.
8,246,577 B2 8/2012 Schrul et al.
8,246,949 B2 8/2012 Higuchi et al.
8,263,016 B2 9/2012 Kanner
8,263,102 B2 9/2012 Labrecque et al.
8,268,238 B2 9/2012 Bondar et al.
8,268,257 B2 9/2012 Frost
8,276,583 B2 10/2012 Farieta et al.
8,277,724 B2 10/2012 Jung et al.
8,312,836 B2 11/2012 Corbeil et al.
8,323,582 B2 12/2012 Ko
8,329,098 B2 12/2012 Kanner
8,329,113 B2 12/2012 Kanner
8,329,119 B2 12/2012 Pearcy et al.
8,333,931 B2 12/2012 Kanner
8,337,772 B2 12/2012 Laumer et al.
8,343,435 B2 1/2013 Kanner
8,348,905 B2 1/2013 Radmer et al.
8,349,272 B2 1/2013 Hill
8,357,331 B2 1/2013 McVey et al.
8,366,680 B2 2/2013 Raab
8,366,995 B2 2/2013 McLaren et al.
8,367,099 B2 2/2013 Herweck et al.
8,388,761 B2 3/2013 Iwashita et al.
8,394,068 B2 3/2013 Kosinski et al.
8,399,006 B2 3/2013 De Juan, Jr. et al.
8,414,912 B2 4/2013 Ciolino et al.
8,425,837 B2 4/2013 Carbone et al.
8,428,447 B2 4/2013 Von Stenglin
8,431,076 B2 4/2013 Fraundorfer
8,431,077 B2 4/2013 Goncalves
8,435,459 B2 5/2013 Reddy et al.
8,444,919 B2 5/2013 Erickson
8,486,332 B1 7/2013 Ricciardi et al.
8,497,004 B2 7/2013 Davis et al.
8,506,900 B1 8/2013 Ricciardi et al.
8,521,273 B2 8/2013 Kliman
8,529,832 B2 9/2013 Lee
8,574,618 B2 11/2013 Herweck et al.
8,574,627 B2 11/2013 Martakos et al.
8,591,807 B2 11/2013 Berentsveig et al.
8,591,808 B2 11/2013 Berentsveig et al.
8,597,680 B2 12/2013 Coppeta et al.
8,617,109 B2 12/2013 Kronestedt et al.
8,621,824 B2 1/2014 Mielnik et al.
8,623,395 B2 1/2014 De Juan, Jr. et al.
8,628,501 B2 1/2014 Hadden
8,636,713 B2 1/2014 Prausnitz et al.
8,641,982 B2 2/2014 Burgmeier et al.
8,652,403 B2 2/2014 Reddy et al.
8,657,804 B2 2/2014 Horne et al.

(56) References Cited

U.S. PATENT DOCUMENTS 8,658,089 B2 2/2014 Berentsveig et al.
8,658,092 B2 2/2014 Kohler et al.
8,663,555 B2 3/2014 Shiosawa
8,663,639 B2 3/2014 Dor et al.
8,685,336 B2 4/2014 Bondar
8,685,337 B2 4/2014 Beckmann et al.
8,696,986 B2 4/2014 Rovison, Jr. et al.
8,703,066 B2 4/2014 Vaughn et al.
8,715,570 B2 5/2014 Lindblad et al.
8,721,601 B2 5/2014 Burren et al.
8,721,983 B2 5/2014 Yokoi et al.
8,721,984 B2 5/2014 Carbone et al.
8,722,077 B2 5/2014 Labrecque et al.
8,722,132 B2 5/2014 Labrecque et al.
8,727,117 B2 5/2014 Maasarani
8,741,227 B2 6/2014 Yokoi et al.
8,758,679 B2 6/2014 Hyde et al.
8,758,681 B2 6/2014 Golkowski
8,765,064 B2 7/2014 Yokoi et al.
8,771,595 B2 7/2014 Paskalov
8,790,576 B2 7/2014 Bauer et al.
8,808,225 B2 8/2014 Prausnitz et al.
8,808,622 B2 8/2014 Arnold et al.
8,808,631 B2 8/2014 Hill et al.
8,821,807 B2 9/2014 Schwartz et al.
8,821,943 B2 9/2014 Kompella et al.
8,834,790 B2 9/2014 Boschi et al.
8,834,808 B2 9/2014 Drenguis
8,834,884 B2 9/2014 Trogden et al.
8,840,836 B2 9/2014 Olson
8,858,978 B2 10/2014 Labrecque et al.
8,865,066 B2 10/2014 Rovison et al.
8,871,145 B2 10/2014 Paskalov
8,894,926 B2 11/2014 Hanada et al.
8,900,201 B2 12/2014 Edhouse et al.
8,911,402 B2 12/2014 Veasey et al.
8,911,426 B2 12/2014 Coppeta et al.
8,911,768 B2 12/2014 Whitcup et al.
8,915,404 B2 12/2014 Farne'et al.
8,919,359 B2 12/2014 Iwashita et al.
8,932,535 B2 1/2015 Hyde et al.
8,936,577 B2 1/2015 Lee et al.
8,940,245 B2 1/2015 Reddy et al.
8,945,048 B2 2/2015 Thorley et al.
8,945,468 B2 2/2015 Reddy et al.
8,948,863 B2 2/2015 Kraft et al.
8,956,655 B2 2/2015 Lyons et al.
8,956,830 B2 2/2015 Prentice et al.
8,961,872 B2 2/2015 Fehr et al.
8,962,023 B2 2/2015 Labrecque et al.
8,974,730 B2 3/2015 Burns et al.
8,974,737 B2 3/2015 Erickson
8,979,807 B2 3/2015 Grunhut et al.
8,992,484 B2 3/2015 Radmer et al.
8,992,837 B2 3/2015 Jung et al.
8,992,853 B2 3/2015 Stratman et al.
D729,931 S 5/2015 Takeuchi et al.
9,022,001 B2 5/2015 Shafto
9,022,079 B2 5/2015 Py et al.
9,023,350 B2 5/2015 Gallo Barraco
9,028,749 B2 5/2015 Ryu et al.
9,033,934 B2 5/2015 Karlsson et al.
9,034,249 B2 5/2015 Foreman et al.
9,044,548 B2 6/2015 Miller et al.
9,050,385 B2 6/2015 Weinberger et al.
9,078,435 B2 7/2015 Dunn
9,078,943 B2 7/2015 Herold et al.
9,101,679 B2 8/2015 Robitaille et al.
9,108,835 B2 8/2015 Hayakawa et al.
9,114,212 B2 8/2015 Enggaard et al.
9,120,660 B2 9/2015 Sangi et al.
9,120,661 B2 9/2015 Sangi et al.
9,125,960 B2 9/2015 Stratman et al.
9,125,988 B2 9/2015 Karlsson
9,138,005 B2 9/2015 Berentsveig et al.
9,144,648 B2 9/2015 Lesch, Jr. et al.
D741,476 S 10/2015 Hiraoka et al.
9,156,576 B2 10/2015 Pjanic et al.
9,173,968 B2 11/2015 Hanada
9,180,047 B2 11/2015 Andino et al.
9,180,217 B2 11/2015 Arnold et al.
9,186,460 B2 11/2015 Macdonald et al.
9,192,164 B2 11/2015 Berentsveig et al.
9,192,567 B2 11/2015 Rabinovich-Guilatt et al.
9,192,725 B2 11/2015 Kawamura
9,213,341 B2 12/2015 Hill
9,217,168 B2 12/2015 Prentice
9,220,631 B2 12/2015 Sigg et al.
9,220,820 B2 12/2015 Faucher et al.
D747,796 S 1/2016 Romao
9,238,106 B2 1/2016 Jones
9,241,491 B2 1/2016 Berentsveig et al.
9,242,053 B2 1/2016 Wozencroft
9,242,753 B2 1/2016 Gay et al.
9,248,229 B2 2/2016 Devouassoux et al.
9,254,338 B2 2/2016 Yancopoulos
9,254,343 B2 2/2016 Herold et al.
9,265,604 B2 2/2016 Woods
9,265,814 B2 2/2016 Kauper et al.
9,265,827 B2 2/2016 Wiegand et al.
9,271,866 B2 3/2016 Humayun et al.
9,284,369 B2 3/2016 Ferrara et al.
9,289,560 B2 3/2016 Raab et al.
9,295,744 B2 3/2016 Rovison et al.
9,302,021 B2 4/2016 Klobusnik
9,308,124 B2 4/2016 Humayun et al.
9,320,647 B2 4/2016 Lerner et al.
9,320,819 B2 4/2016 Koyama
9,320,820 B2 4/2016 Rovison, Jr. et al.
9,339,573 B2 5/2016 Seidenberg et al.
9,340,594 B2 5/2016 Furfine et al.
9,345,838 B2 5/2016 Plumptre
9,345,866 B2 5/2016 Kubo et al.
9,352,104 B2 5/2016 Thorley et al.
9,358,301 B2 6/2016 Friberg et al.
9,364,571 B2 6/2016 Ahiska
9,388,239 B2 7/2016 Baldi et al.
D765,241 S 8/2016 Holland
9,402,928 B2 8/2016 Tremblay et al.
9,403,330 B2 8/2016 Laumer et al.
9,408,746 B2 8/2016 Lerner et al.
9,408,931 B1 8/2016 Ricciardi et al.
9,408,965 B2 8/2016 Christensen
9,410,191 B2 8/2016 Alvarez, Jr. et al.
9,414,960 B2 8/2016 Woods
9,421,129 B2 8/2016 Lerner
9,427,485 B2 8/2016 Tremblay et al.
9,439,991 B2 9/2016 Schwartz et al.
9,452,138 B2 9/2016 Trollsas et al.
9,452,231 B2 9/2016 Nonnenmacher
9,457,114 B2 10/2016 Loy
9,463,259 B2 10/2016 Hanada
9,474,688 B2 10/2016 Weeks et al.
9,474,815 B2 10/2016 Dufresne et al.
9,475,225 B2 10/2016 Giraud et al.
D770,612 S 11/2016 Green et al.
9,480,763 B2 11/2016 Dufresne et al.
9,480,764 B2 11/2016 Tremblay et al.
9,480,765 B2 11/2016 Tremblay et al.
9,487,810 B2 11/2016 Prentice et al.
9,498,549 B2 11/2016 Kanno et al.
9,504,603 B2 11/2016 Lerner
9,505,598 B2 11/2016 Niehr et al.
9,505,830 B2 11/2016 Ordas et al.
9,522,202 B1 12/2016 Ahiska et al.
9,522,205 B2 12/2016 Ahiska
9,526,837 B2 12/2016 Carrel et al.
9,526,841 B2 12/2016 Kubo et al.
9,533,065 B2 1/2017 Foreman et al.
9,533,100 B2 1/2017 Jones
9,539,352 B2 1/2017 Keener et al.
9,539,391 B2 1/2017 Lee et al.
9,541,487 B2 1/2017 Saito et al.
9,545,473 B2 1/2017 Devouassoux et al.

(56) References Cited

U.S. PATENT DOCUMENTS 9,545,481 B1 1/2017 Rafaat
9,554,968 B2 1/2017 Weikart et al.
9,555,146 B2 1/2017 Fehr et al.
D778,174 S 2/2017 Zhang et al.
9,561,297 B2 2/2017 Kreber
9,566,360 B2 2/2017 Morikawa et al.
9,566,361 B2 2/2017 Morikawa et al.
9,572,800 B2 2/2017 Zarnitsyn et al.
9,572,932 B2 2/2017 Eggert et al.
9,572,940 B2 2/2017 Horlock
9,592,324 B2 3/2017 Herweck et al.
9,593,004 B2 3/2017 Hayakawa et al.
9,597,377 B2 3/2017 Fan
9,603,739 B2 3/2017 Lerner
9,604,015 B2 3/2017 Gramage Pina
9,604,740 B2 3/2017 Py
9,616,368 B2 4/2017 Turbett et al.
9,617,135 B2 4/2017 Hayakawa et al.
9,617,136 B2 4/2017 Hayakawa et al.
9,629,936 B2 4/2017 Salmisuo
9,636,253 B1 5/2017 Andino et al.
9,636,332 B2 5/2017 Zarnitsyn et al.
9,637,604 B2 5/2017 Ito et al.
9,650,444 B2 5/2017 Wiegand et al.
9,662,244 B2 5/2017 Hatta et al.
9,662,412 B2 5/2017 Ferrell et al.
9,662,450 B2 5/2017 Jones et al.
9,663,810 B2 5/2017 Prentice
D790,691 S 6/2017 Davis et al.
9,668,915 B2 6/2017 Haffner et al.
9,669,069 B2 6/2017 Yancopoulos
9,669,988 B2 6/2017 Kojima et al.
9,675,763 B2 6/2017 Huet
9,677,105 B2 6/2017 Collins et al.
9,682,154 B2 6/2017 Leubitz et al.
9,682,163 B2 6/2017 Loy et al.
9,682,175 B2 6/2017 Labrecque et al.
9,694,095 B2 7/2017 Paskalov
9,708,390 B2 7/2017 Sivakumar et al.
RE46,510 E 8/2017 Odell et al.
D794,185 S 8/2017 Dolk et al.
D794,187 S 8/2017 Dolk et al.
9,717,854 B2 8/2017 Evans et al.
9,724,438 B2 8/2017 Turbett
9,737,667 B2 8/2017 Holmqvist et al.
9,750,832 B2 9/2017 Paver, Jr.
9,750,887 B2 9/2017 Hirschel et al.
9,750,888 B2 9/2017 Raab et al.
9,757,452 B2 9/2017 Pham
9,766,012 B2 9/2017 McLaren et al.
9,770,361 B2 9/2017 Andino et al.
9,770,559 B2 9/2017 Armstrong
D800,900 S 10/2017 Darras et al.
9,775,924 B2 10/2017 Tanimoto et al.
9,788,995 B2 10/2017 Prausnitz et al.
9,802,726 B2 10/2017 Mielnik et al.
9,814,795 B2 11/2017 Dufresne et al.
9,814,796 B2 11/2017 Dunn
9,814,840 B2 11/2017 Cowe et al.
9,827,341 B2 11/2017 Fehr et al.
9,833,523 B2 12/2017 Christoforidis et al.
9,849,244 B2 12/2017 Plumptre et al.
9,867,948 B2 1/2018 Selz et al.
9,872,961 B2 1/2018 Fourt et al.
D810,282 S 2/2018 Ratjen
9,895,259 B2 2/2018 Lerner
9,896,480 B2 2/2018 Mackel et al.
D812,223 S 3/2018 Evans et al.
D814,026 S 3/2018 Darras et al.
9,907,913 B2 3/2018 Kosinski et al.
9,913,750 B2 3/2018 Lerner
9,919,057 B2 3/2018 Kim et al.
9,925,340 B2 3/2018 Glocker
D815,279 S 4/2018 Darras et al.
9,931,330 B2 4/2018 Zarnitsyn et al.
9,932,630 B2 4/2018 Alvarez, Jr. et al.
9,937,099 B2 4/2018 Weikart et al.
9,937,335 B2 4/2018 Moss et al.
9,943,573 B2 4/2018 Constable et al.
9,950,116 B2 4/2018 Plumptre et al.
9,956,114 B2 5/2018 Andino et al.
9,957,324 B2 5/2018 Josiah et al.
9,962,333 B2 5/2018 Gaillard et al.
9,962,493 B2 5/2018 Guthart
9,968,603 B2 5/2018 Astafieva et al.
9,968,743 B2 5/2018 Kuwahara et al.
9,982,032 B2 5/2018 Park et al.
D819,805 S 6/2018 Knight et al.
9,993,568 B2 6/2018 Kim et al.
9,995,706 B2 6/2018 Schenk et al.
9,999,595 B2 6/2018 Rakic et al.
10,004,788 B2 6/2018 Constable et al.
10,010,447 B2 7/2018 Kashani et al.
10,016,338 B2 7/2018 Weikart et al.
10,022,502 B2 7/2018 Wong et al.
10,034,922 B2 7/2018 Kim
10,035,850 B2 7/2018 Gekkieva et al.
10,046,027 B2 8/2018 Jensen et al.
10,058,106 B2 8/2018 Itarashiki et al.
10,064,997 B2 9/2018 Evans et al.
10,065,784 B2 9/2018 Tanoguchi
10,073,949 B2 9/2018 Ballou, Jr. et al.
10,080,682 B2 9/2018 Horvath et al.
D830,540 S 10/2018 Rolfs et al.
D830,543 S 10/2018 Walker et al.
10,092,708 B2 10/2018 Thorley et al.
10,106,605 B2 10/2018 Ghosh et al.
10,111,975 B2 10/2018 Laflamme et al.
10,117,774 B2 11/2018 Humayun et al.
10,130,681 B2 11/2018 Yancopoulos
10,137,249 B2 11/2018 Oakley et al.
D838,363 S 1/2019 Katagiri et al.
10,166,142 B2 1/2019 De Juan, Jr. et al.
10,172,682 B2 1/2019 Van Der Raad-Meijer et al.
10,179,206 B2 1/2019 Bendek et al.
10,195,348 B2 2/2019 Komann
10,196,685 B2 2/2019 Alvarez, Jr. et al.
10,206,813 B2 2/2019 Haffner et al.
10,213,556 B2 2/2019 Young et al.
10,213,557 B2 2/2019 Eggert et al.
10,213,558 B2 2/2019 Raghuveer et al.
10,214,338 B2 2/2019 Devouassoux et al.
10,226,728 B2 3/2019 Turbett et al.
10,232,119 B2 3/2019 Raab et al.
D845,476 S 4/2019 Evans et al.
10,245,178 B1 4/2019 Heitzmann et al.
10,245,335 B2 4/2019 Turbett et al.
D849,935 S 5/2019 Rolfs et al.
10,293,068 B2 5/2019 Ruley et al.
10,293,965 B2 5/2019 Lu et al.
D851,753 S 6/2019 Green
10,329,073 B2 6/2019 Tanoguchi
10,350,306 B2 7/2019 Sieving et al.
10,350,346 B2 7/2019 Kerschbaumer et al.
10,363,214 B2 7/2019 Whitcup et al.
10,369,107 B2 8/2019 McDonnel et al.
10,370,442 B2 8/2019 Portugal et al.
10,376,582 B2 8/2019 Cini et al.
10,383,954 B2 8/2019 Leubitz et al.
10,383,966 B2 8/2019 Dufresne et al.
10,385,842 B2 8/2019 Kuczek et al.
10,391,259 B2 8/2019 Tran et al.
10,420,724 B2 9/2019 Jarrett et al.
10,426,659 B2 10/2019 Myung et al.
10,426,817 B2 10/2019 Rudolf et al.
D865,946 S 11/2019 Horlock
10,471,212 B2 11/2019 Ashmead et al.
10,478,335 B2 11/2019 Lerner
10,517,756 B2 12/2019 Andino et al.
10,519,226 B2 12/2019 Rau et al.
10,524,957 B2 1/2020 Lerner
10,537,494 B2 1/2020 Weikart et al.
10,537,563 B2 1/2020 Adams et al.
10,556,008 B2 2/2020 Pham

(56) References Cited

U.S. PATENT DOCUMENTS 10,568,934 B2 2/2020 Hohman
10,568,951 B2 2/2020 Sigl
D878,569 S 3/2020 Reynolds et al.
D878,576 S 3/2020 Johnson
10,576,128 B2 3/2020 Sigl
10,588,855 B2 3/2020 Ambati et al.
10,603,427 B2 3/2020 Hasumi
10,617,557 B2 4/2020 De Juan et al.
10,632,013 B2 4/2020 Prausnitz et al.
10,653,621 B2 5/2020 Wu et al.
10,656,152 B2 5/2020 De Juan, Jr. et al.
10,683,345 B2 6/2020 Duerr et al.
D889,639 S 7/2020 Johnson et al.
D891,611 S 7/2020 Valentin et al.
10,709,803 B2 7/2020 Laflamme et al.
10,710,759 B2 7/2020 Lu et al.
10,722,396 B2 7/2020 Andino et al.
D892,313 S 8/2020 Lin
D892,321 S 8/2020 Newton
10,730,825 B2 8/2020 Bavik et al.
10,730,944 B2 8/2020 Giurleo et al.
10,751,417 B2 8/2020 Adams et al.
10,752,901 B2 8/2020 Corson et al.
D895,110 S 9/2020 Takada et al.
10,765,759 B2 9/2020 Healy et al.
10,773,014 B2 9/2020 Maasarani
10,781,027 B2 9/2020 Devouassoux et al.
10,786,462 B2 9/2020 Jarrett et al.
10,799,639 B2 10/2020 Wei
10,799,642 B2 10/2020 Wong et al.
10,806,630 B2 10/2020 Price et al.
10,813,788 B2 10/2020 De Juan, Jr. et al.
10,813,789 B2 10/2020 Haffner et al.
10,821,221 B2 11/2020 Takahashi et al.
10,828,345 B2 11/2020 Yancopoulos
10,839,960 B2 11/2020 Ballou, Jr. et al.
10,851,165 B2 12/2020 Freeman et al.
10,857,205 B2 12/2020 Yancopoulos
10,888,601 B2 1/2021 Yancopoulos
10,905,586 B2 2/2021 Prausnitz et al.
10,905,587 B2 2/2021 Lerner
10,905,784 B2 2/2021 Kelly et al.
10,906,969 B2 2/2021 Lee et al.
10,912,714 B2 2/2021 Weikart et al.
10,925,927 B2 2/2021 Brockmeyer et al.
10,961,304 B2 3/2021 Eriksson et al.
10,973,681 B2 4/2021 Andino et al.
10,973,879 B2 4/2021 Vitti et al.
10,980,766 B2 4/2021 Huang et al.
10,980,890 B2 4/2021 Kim et al.
10,993,834 B2 5/2021 Kahook
11,007,259 B2 5/2021 Murakami et al.
11,020,530 B2 6/2021 Takeuchi et al.
11,020,531 B2 6/2021 Ashmead et al.
11,026,885 B2 6/2021 Ashton et al.
11,028,448 B2 6/2021 Innocenti et al.
11,052,094 B2 7/2021 Ostrow et al.
11,052,095 B2 7/2021 Ostrow et al.
11,052,130 B2 7/2021 Kim et al.
11,065,151 B2 7/2021 De Juan, Jr. et al.
11,077,188 B2 8/2021 Kauvar et al.
11,078,262 B2 8/2021 Hughes et al.
11,090,445 B2 8/2021 Diaz et al.
11,096,822 B2 8/2021 Yamamoto et al.
11,098,110 B2 8/2021 Gekkieva et al.
11,103,552 B2 8/2021 Graham et al.
11,103,644 B2 8/2021 Bryant et al.
11,110,001 B2 9/2021 Bachelder et al.
11,110,226 B2 9/2021 Bryant et al.
11,111,291 B2 9/2021 Famili et al.
11,116,695 B2 9/2021 Weikart et al.
11,135,266 B2 10/2021 Kerwin et al.
11,147,925 B2 10/2021 Bryant et al.
11,154,420 B2 10/2021 Yamamoto et al.
11,160,918 B2 11/2021 Cook et al.
11,161,916 B2 11/2021 Gschwind et al.
11,179,521 B2 11/2021 Bryant et al.
11,185,499 B2 11/2021 Desai et al.
11,185,635 B2 11/2021 Bryant et al.
11,202,762 B2 12/2021 Mihov et al.
11,209,444 B2 12/2021 Baldwin et al.
D940,302 S 1/2022 Wu
D940,306 S 1/2022 Osypka et al.
11,214,426 B2 1/2022 Devouassoux et al.
11,219,552 B2 1/2022 Olson
11,241,380 B2 2/2022 Freeman et al.
11,253,572 B2 2/2022 Yancopoulos
11,253,620 B2 2/2022 Golkowski et al.
11,266,608 B2 3/2022 Kang-Mieler et al.
11,266,743 B2 3/2022 Wimley et al.
11,291,636 B2 4/2022 Chen et al.
11,298,405 B2 4/2022 Brockmeyer et al.
11,298,437 B2 4/2022 Conseil et al.
D950,721 S 5/2022 Howes et al.
D953,089 S 5/2022 Scheinert
11,331,430 B2 5/2022 Dobson
D954,258 S 6/2022 Hang et al.
D954,942 S 6/2022 Lee
D956,205 S 6/2022 Nimkar et al.
11,351,347 B2 6/2022 Myung et al.
11,369,591 B2 6/2022 Jarrett et al.
D957,630 S 7/2022 Punim
11,382,955 B2 7/2022 Ferrara
11,383,006 B2 7/2022 Hughes et al.
11,389,594 B2 7/2022 Smith et al.
D961,067 S 8/2022 Schootstra et al.
11,400,080 B2 8/2022 Maturi
11,406,592 B2 8/2022 De Juan, Jr. et al.
11,419,985 B2 8/2022 Wei
11,426,306 B2 8/2022 Haffner et al.
D965,141 S 9/2022 Oldfield et al.
11,433,118 B2 9/2022 Ferrara
11,452,811 B2 9/2022 Kerschbaumer et al.
D967,414 S 10/2022 Cebadera Miranda
11,458,199 B2 10/2022 Santos et al.
11,459,374 B2 10/2022 Tustian et al.
11,478,465 B2 10/2022 Eriksson et al.
D969,992 S 11/2022 Espinoza
11,504,431 B2 11/2022 Prausnitz et al.
11,505,593 B2 11/2022 Wang et al.
11,510,869 B2 11/2022 Doshi
D973,203 S 12/2022 Tyrsing et al.
D973,873 S 12/2022 Tyrsing et al.
11,518,984 B2 12/2022 Her et al.
11,524,998 B2 12/2022 Bigelow et al.
11,525,001 B2 12/2022 Giurleo et al.
11,534,396 B2 12/2022 Blizzard et al.
11,541,139 B2 1/2023 Eveland
11,542,317 B1 1/2023 Wang et al.
11,554,215 B2 1/2023 Hawson et al.
11,559,428 B2 1/2023 Andino et al.
11,559,520 B2 1/2023 Surber
11,559,564 B2 1/2023 Yancopoulos
11,564,834 B2 1/2023 Bley et al.
11,564,907 B2 1/2023 Muller et al.
D979,054 S 2/2023 Lee-Sepsick et al.
D979,750 S 2/2023 Dyk
11,576,948 B2 2/2023 Ferrara
11,584,774 B2 2/2023 Iyer et al.
11,596,545 B2 3/2023 Andino et al.
11,596,667 B2 3/2023 Rezaei
D983,965 S 4/2023 Siddiqui
11,618,782 B2 4/2023 Ziegelaar et al.
11,622,884 B2 4/2023 Bley et al.
11,633,300 B2 4/2023 Lazar
11,633,545 B2 4/2023 Vedrine et al.
D986,413 S 5/2023 Atterbury et al.
D987,820 S 5/2023 Yabe
11,642,214 B2 5/2023 Loria
11,642,310 B2 5/2023 De Juan, Jr. et al.
11,654,046 B2 5/2023 Weikart et al.
11,660,266 B2 5/2023 Jiang et al.
D989,302 S 6/2023 Hang et al.
D989,951 S 6/2023 Renou et al.

(56) References Cited

U.S. PATENT DOCUMENTS 11,666,632 B2 6/2023 Brockmeyer et al.
11,672,800 B2 6/2023 Campbell et al.
11,679,027 B2 6/2023 De Juan, Jr. et al.
11,680,266 B2 6/2023 D'Amore et al.
11,692,027 B2 7/2023 Kraft et al.
11,707,506 B2 7/2023 Yancopoulos
11,707,531 B2 7/2023 Iyer
11,707,577 B2 7/2023 Shetty et al.
11,723,982 B2 8/2023 Healy et al.
11,725,246 B2 8/2023 Ghosh et al.
11,730,794 B2 8/2023 Yancopoulos
11,738,007 B2 8/2023 Gurkan et al.
11,738,064 B2 8/2023 Kim et al.
11,739,294 B2 8/2023 Klassen et al.
D998,146 S 9/2023 Kelleher et al.
11,752,101 B2 9/2023 Yamamoto et al.
11,752,225 B2 9/2023 Shieu et al.
11,759,577 B2 9/2023 Shanley et al.
11,766,489 B2 9/2023 Kirn et al.
11,786,396 B2 10/2023 De Juan, Jr. et al.
11,793,926 B2 10/2023 Cook et al.
11,795,136 B2 10/2023 Bavik et al.
11,806,513 B2 11/2023 Bowman et al.
11,813,196 B2 11/2023 Erickson et al.
11,819,454 B2 11/2023 Nazzaro
11,826,431 B2 11/2023 Wei et al.
D1,025,354 S 4/2024 Ullsten et al.
D1,028,225 S 5/2024 Kubo et al.
D1,037,440 S 7/2024 Suzuki et al.
12,048,837 B2 7/2024 Bryant et al.
12,059,555 B2 8/2024 Mismar et al.
D1,048,392 S 10/2024 Hang et al.
2001/0021382 A1 9/2001 Ferrara et al.
2002/0098187 A1 7/2002 Ferrara et al.
2002/0161334 A1 10/2002 Castellano et al.
2002/0177819 A1 11/2002 Barker et al.
2002/0194630 A1 12/2002 Manning et al.
2003/0004467 A1 1/2003 Musick et al.
2003/0032928 A1 2/2003 Sudo et al.
2003/0139707 A1 7/2003 Hommann et al.
2003/0236503 A1 12/2003 Koenig et al.
2004/0064105 A1 4/2004 Capes et al.
2004/0097883 A1 5/2004 Roe
2004/0122359 A1 6/2004 Wenz et al.
2004/0162528 A1 8/2004 Horvath et al.
2004/0199113 A1 10/2004 Capes et al.
2004/0220524 A1 11/2004 Sadowski et al.
2004/0236285 A1 11/2004 Fisher et al.
2005/0004530 A1 1/2005 Grabenkort et al.
2005/0027255 A1 2/2005 Lavi et al.
2005/0090782 A1 4/2005 Marshall et al.
2005/0131354 A1 6/2005 Tachikawa et al.
2005/0182370 A1 8/2005 Hato
2005/0215957 A1 9/2005 Hynes
2006/0153693 A1 7/2006 Fiechter et al.
2006/0193862 A1 8/2006 Ferrara et al.
2006/0223027 A1 10/2006 Smith et al.
2006/0258988 A1 11/2006 Keitel et al.
2006/0264815 A1 11/2006 Hommann et al.
2006/0270984 A1 11/2006 Hommann
2006/0270985 A1 11/2006 Hommann et al.
2007/0016142 A1 1/2007 Burren et al.
2007/0027101 A1 2/2007 Guyer et al.
2007/0059302 A1 3/2007 Baca et al.
2007/0088268 A1 4/2007 Edwards et al.
2007/0190058 A1 8/2007 Shams
2007/0203144 A1 8/2007 Kusari et al.
2007/0233001 A1 10/2007 Burroughs et al.
2007/0233009 A1 10/2007 Kirchhofer
2007/0253959 A1 11/2007 Ferrara et al.
2007/0265580 A1 11/2007 Tachikawa et al.
2007/0280902 A1 12/2007 Rabinovich-Guilatt et al.
2007/0281913 A1 12/2007 Rabinovich-Guilatt et al.
2007/0281914 A1 12/2007 Rabinovich-Guilatt et al.
2008/0019977 A1 1/2008 Adamis
2008/0065027 A1 3/2008 Sharp
2008/0071227 A1 3/2008 Moser et al.
2008/0082044 A1 4/2008 Sharon et al.
2008/0135130 A1 6/2008 Py et al.
2008/0160019 A1 7/2008 Wood et al.
2008/0181900 A1 7/2008 Ferrara et al.
2008/0183138 A1 7/2008 Moser et al.
2008/0202961 A1 8/2008 Sharp
2008/0208123 A1 8/2008 Hommann
2008/0269692 A1 10/2008 James et al.
2009/0005735 A1 1/2009 Wikner et al.
2009/0062746 A1 3/2009 Heffernan et al.
2009/0074786 A1 3/2009 Dor et al.
2009/0087424 A1 4/2009 Miyamoto et al.
2009/0098139 A1 4/2009 Katz et al.
2009/0149743 A1 6/2009 Barron et al.
2009/0169556 A1 7/2009 Ferrara et al.
2009/0196903 A1 8/2009 Kliman
2009/0254036 A1 10/2009 Asmussen et al.
2009/0275914 A1 11/2009 Harms et al.
2009/0299278 A1 12/2009 Lesch, Jr. et al.
2010/0010472 A1 1/2010 Moore
2010/0016807 A1 1/2010 Thilly
2010/0036320 A1 2/2010 Cox et al.
2010/0111963 A1 5/2010 Shams
2010/0119523 A1 5/2010 Ferrara et al.
2010/0152671 A1 6/2010 Raab et al.
2010/0160894 A1 6/2010 Julian et al.
2010/0175779 A1 7/2010 Ogawa et al.
2010/0185205 A1 7/2010 Novakovic et al.
2010/0186739 A1 7/2010 Kronestedt et al.
2010/0292672 A1 11/2010 Lee
2010/0298779 A1 11/2010 Hetzler et al.
2010/0305514 A1 12/2010 Valenti et al.
2010/0316652 A1 12/2010 Ferrara et al.
2010/0318063 A1 12/2010 Soll
2011/0009829 A1 1/2011 Kosinski et al.
2011/0009830 A1 1/2011 Kosinski et al.
2011/0092915 A1 4/2011 Olson et al.
2011/0098640 A1 4/2011 Horne et al.
2011/0110932 A1 5/2011 Patel
2011/0190709 A1 8/2011 Mitsuno et al.
2011/0276026 A1 11/2011 Dowds
2011/0287024 A1 11/2011 Ferrara et al.
2012/0009185 A1 1/2012 Shams
2012/0035528 A1 2/2012 Coppeta et al.
2012/0070428 A1 3/2012 Chan et al.
2012/0104045 A1 5/2012 Chang
2012/0114524 A1 5/2012 Sigg
2012/0128670 A1 5/2012 Barr et al.
2012/0143146 A1 6/2012 Strehl et al.
2012/0197211 A1 8/2012 Brister et al.
2012/0203184 A1 8/2012 Selz et al.
2012/0226240 A1 9/2012 Bedford et al.
2012/0232492 A1 9/2012 Hato
2012/0245530 A1 9/2012 Oden et al.
2012/0283654 A1 11/2012 MacDonald et al.
2012/0316509 A1 12/2012 Kayser et al.
2013/0004384 A1 1/2013 Yoo
2013/0004486 A1 1/2013 Chan et al.
2013/0006192 A1 1/2013 Teucher et al.
2013/0028911 A1 1/2013 Ferrara et al.
2013/0060232 A1 3/2013 Adlon et al.
2013/0082057 A1 4/2013 Schiff et al.
2013/0085452 A1 4/2013 Schiff et al.
2013/0085455 A1 4/2013 Manke et al.
2013/0085458 A1 4/2013 Manke et al.
2013/0110054 A1 5/2013 Raab et al.
2013/0136697 A1 5/2013 Kannan et al.
2013/0150803 A1 6/2013 Shetty et al.
2013/0195806 A1 8/2013 Gay et al.
2013/0197016 A1 8/2013 Brigell et al.
2013/0218081 A1 8/2013 Roth
2013/0218130 A1 8/2013 Plumptre et al.
2013/0224110 A1 8/2013 Bynoe
2013/0289491 A1 10/2013 Kramer et al.
2013/0296779 A1 11/2013 Kuehne et al.
2013/0303985 A1 11/2013 Wotton et al.
2013/0310744 A1 11/2013 Brereton et al.

(56) References Cited

U.S. PATENT DOCUMENTS

2013/0317431 A1 11/2013 Kramer et al.
2013/0317477 A1 11/2013 Edwards et al.
2013/0323242 A1 12/2013 Everett et al.
2013/0324924 A1 12/2013 Brereton et al.
2014/0005610 A1 1/2014 Kakiuchi et al.
2014/0012227 A1 1/2014 Sigg et al.
2014/0058335 A1 2/2014 Mudd
2014/0086934 A1 3/2014 Shams
2014/0093499 A1 4/2014 Gschwind et al.
2014/0114208 A1 4/2014 Smith et al.
2014/0135712 A1 5/2014 Horne et al.
2014/0148792 A1 5/2014 Coppeta et al.
2014/0179621 A1 6/2014 Patel et al.
2014/0180217 A1 6/2014 Kuczek et al.
2014/0221934 A1 8/2014 Janvier et al.
2014/0223862 A1 8/2014 Nicoletti et al.
2014/0271622 A1 9/2014 Prentice
2014/0288507 A1 9/2014 Samuel
2014/0294816 A1 10/2014 Shima et al.
2014/0303556 A1 10/2014 Travanty
2014/0336589 A1 11/2014 Sund et al.
2014/0350516 A1 11/2014 Schwab et al.
2014/0377276 A1 12/2014 Ferrara et al.
2015/0017163 A1 1/2015 Patel et al.
2015/0018771 A1 1/2015 Schenker et al.
2015/0037422 A1 2/2015 Kaplan et al.
2015/0051551 A1 2/2015 Hirschel et al.
2015/0073355 A1 3/2015 Hirschel et al.
2015/0078961 A1 3/2015 Opie
2015/0105734 A1 4/2015 Bryant et al.
2015/0119810 A1 4/2015 Jakob et al.
2015/0126458 A1 5/2015 Hohman et al.
2015/0152503 A1 6/2015 Boisen et al.
2015/0157709 A1 6/2015 Everett et al.
2015/0157801 A1 6/2015 Tran et al.
2015/0182623 A1 7/2015 Everett et al.
2015/0190566 A1 7/2015 Okihara
2015/0202289 A1 7/2015 Shima et al.
2015/0224266 A1 8/2015 Plumptre et al.
2015/0297453 A1 10/2015 Kim et al.
2015/0297454 A1 10/2015 Sanders et al.
2015/0297675 A1 10/2015 Osborne
2015/0297839 A1 10/2015 Sanders et al.
2015/0320782 A1 11/2015 Panjwani et al.
2015/0328151 A1 11/2015 Ballou, Jr. et al.
2015/0335826 A1 11/2015 Huet
2015/0352298 A1 12/2015 Egerström et al.
2015/0374924 A1 12/2015 Keitel et al.
2016/0008540 A1 1/2016 Fourt et al.
2016/0022919 A1 1/2016 Cammish et al.
2016/0038589 A1 2/2016 Patel
2016/0106928 A1 4/2016 Davis et al.
2016/0129080 A1 5/2016 Osborne
2016/0130321 A1 5/2016 Burian
2016/0137717 A1 5/2016 Burian
2016/0144122 A1 5/2016 Locati et al.
2016/0144128 A1 5/2016 Oakley et al.
2016/0151578 A1 6/2016 Oakley et al.
2016/0159893 A1 6/2016 Burian et al.
2016/0168240 A1 6/2016 Burian et al.
2016/0193421 A1 7/2016 Bayer et al.
2016/0213852 A1 7/2016 Harms et al.
2016/0220540 A1 8/2016 Peters et al.
2016/0220759 A1 8/2016 Enggaard et al.
2016/0220761 A1 8/2016 Shetty et al.
2016/0220762 A1 8/2016 Goral et al.
2016/0228642 A1 8/2016 Cowe
2016/0264969 A1 9/2016 Patel et al.
2016/0279339 A1 9/2016 Schenker et al.
2016/0296550 A1 10/2016 Patel et al.
2016/0310417 A1 10/2016 Prausnitz et al.
2016/0317752 A1 11/2016 Cowe
2016/0325047 A1 11/2016 Vedrine et al.
2016/0347492 A1 12/2016 Lu et al.
2017/0042816 A1 2/2017 Trollsas et al.
2017/0056469 A1 3/2017 Iezzi
2017/0056923 A1 3/2017 Hioki et al.
2017/0057635 A1 3/2017 Strayer
2017/0080086 A1 3/2017 Vitti et al.
2017/0080159 A1 3/2017 Wei
2017/0100284 A1 4/2017 Lerner
2017/0100306 A1 4/2017 Weikart et al.
2017/0100542 A1 4/2017 Norton et al.
2017/0100543 A1 4/2017 Cabiri et al.
2017/0157207 A1 6/2017 Hohman et al.
2017/0157316 A1 6/2017 Browne
2017/0173161 A1 6/2017 Kaplan et al.
2017/0173267 A1 6/2017 Ashmead et al.
2017/0182253 A1 6/2017 Folk et al.
2017/0182259 A1 6/2017 Fukushi et al.
2017/0189619 A1 7/2017 Constantineau et al.
2017/0197024 A1 7/2017 Kiminami et al.
2017/0203043 A1 7/2017 Rusch et al.
2017/0203052 A1 7/2017 Abe et al.
2017/0224435 A1 8/2017 Godfrey et al.
2017/0232199 A1 8/2017 Fiedler
2017/0233782 A1 8/2017 Collins et al.
2017/0246401 A1 8/2017 Keenan
2017/0258633 A1 9/2017 Vure et al.
2017/0274147 A1 9/2017 Raghuveer et al.
2017/0281872 A1 10/2017 Guthart
2017/0290987 A1 10/2017 Mandaroux et al.
2017/0296756 A1 10/2017 Giraud et al.
2017/0340830 A1 11/2017 Wieselblad et al.
2018/0036488 A1 2/2018 Wei
2018/0042765 A1 2/2018 Noronha et al.
2018/0057602 A1 3/2018 Theuer et al.
2018/0126085 A1 5/2018 Bowman et al.
2018/0126086 A1 5/2018 Kosinski et al.
2018/0133288 A1 5/2018 Kim et al.
2018/0147214 A1 5/2018 Ostrow et al.
2018/0171004 A1 6/2018 Gokarn et al.
2018/0177948 A1 6/2018 Raab et al.
2018/0177949 A1 6/2018 Malefijt et al.
2018/0194835 A1 7/2018 Burian et al.
2018/0207091 A1 7/2018 Brown
2018/0221483 A1 8/2018 Gaillard et al.
2018/0221584 A1 8/2018 Grimoldby et al.
2018/0228649 A1 8/2018 Lerner
2018/0237430 A1 8/2018 Peters et al.
2018/0243513 A1 8/2018 Rolfs et al.
2018/0250474 A1 9/2018 Wei
2018/0251457 A1 9/2018 Peters et al.
2018/0256747 A1 9/2018 Hawthorne et al.
2018/0263816 A1 9/2018 Lerner
2018/0264111 A1 9/2018 Pedrussio et al.
2018/0280622 A1 10/2018 Li et al.
2018/0280623 A1 10/2018 Pilkington
2018/0311319 A1 11/2018 Constable et al.
2018/0326126 A1 11/2018 Fiedler
2018/0333296 A1 11/2018 Heitzmann et al.
2018/0333300 A1 11/2018 Lerner
2018/0361080 A1 12/2018 Diaz et al.
2019/0001065 A1 1/2019 Daniel
2019/0015597 A1 1/2019 Holmqvist et al.
2019/0016817 A1 1/2019 Taddei et al.
2019/0030253 A1 1/2019 Barbour
2019/0076603 A1 3/2019 Thorley et al.
2019/0111212 A1 4/2019 Schiff et al.
2019/0143049 A1 5/2019 Bilgic
2019/0183842 A1 6/2019 Huang et al.
2019/0201430 A1 7/2019 Vavvas et al.
2019/0231986 A1 8/2019 Devaraneni et al.
2019/0290485 A1 9/2019 Andino et al.
2019/0343918 A1 11/2019 Graham et al.
2019/0358123 A1 11/2019 Weikart et al.
2019/0365565 A1 12/2019 Bryant et al.
2019/0381008 A1 12/2019 Zeitz et al.
2019/0381087 A1 12/2019 Patel et al.
2019/0388522 A1 12/2019 Burian et al.
2020/0000635 A1 1/2020 Lerner
2020/0001062 A1 1/2020 Moss et al.
2020/0002411 A1 1/2020 Famili et al.
2020/0023076 A1 1/2020 Fotin-Mleczek et al.

(56) References Cited

U.S. PATENT DOCUMENTS

| | | | |
|---|---|---|---|
| 2020/0031917 | A1 | 1/2020 | Kraft et al. |
| 2020/0048341 | A1 | 2/2020 | Ghosh et al. |
| 2020/0054635 | A1 | 2/2020 | Campbell et al. |
| 2020/0069770 | A1 | 3/2020 | Rudolf et al. |
| 2020/0069814 | A1 | 3/2020 | Zhao et al. |
| 2020/0069816 | A1 | 3/2020 | Kim et al. |
| 2020/0085735 | A1 | 3/2020 | Brown |
| 2020/0093852 | A1 | 3/2020 | Nelms et al. |
| 2020/0129435 | A1 | 4/2020 | Akbari et al. |
| 2020/0147056 | A1 | 5/2020 | Maturi |
| 2020/0155764 | A1 | 5/2020 | Kakiuchi et al. |
| 2020/0163877 | A1 | 5/2020 | Santos et al. |
| 2020/0171244 | A1 | 6/2020 | Weikart et al. |
| 2020/0179167 | A1 | 6/2020 | Bryant et al. |
| 2020/0188405 | A1 | 6/2020 | Kaushal |
| 2020/0188589 | A1 | 6/2020 | Hawson et al. |
| 2020/0188590 | A1 | 6/2020 | Hamlin |
| 2020/0188593 | A1 | 6/2020 | Carrel et al. |
| 2020/0190179 | A1 | 6/2020 | Sigg et al. |
| 2020/0206025 | A1 | 7/2020 | Chalberg, Jr. et al. |
| 2020/0214888 | A1 | 7/2020 | Bryant et al. |
| 2020/0214889 | A1 | 7/2020 | Lerner |
| 2020/0215079 | A1 | 7/2020 | Yang et al. |
| 2020/0222233 | A1 | 7/2020 | Rotenstreich |
| 2020/0222547 | A1 | 7/2020 | Stark et al. |
| 2020/0230237 | A1 | 7/2020 | Kauvar et al. |
| 2020/0237862 | A1 | 7/2020 | Sigl |
| 2020/0237997 | A1 | 7/2020 | Brockmeyer et al. |
| 2020/0261266 | A1 | 8/2020 | Bley et al. |
| 2020/0268899 | A1 | 8/2020 | Iyer |
| 2020/0270299 | A1 | 8/2020 | Iyer et al. |
| 2020/0276261 | A1 | 9/2020 | Zhao et al. |
| 2020/0276322 | A1 | 9/2020 | Wimley et al. |
| 2020/0277364 | A1 | 9/2020 | Yoo et al. |
| 2020/0297869 | A1 | 9/2020 | Cepeda et al. |
| 2020/0297919 | A1 | 9/2020 | Hemminger et al. |
| 2020/0368331 | A1 | 11/2020 | Borodic |
| 2020/0368445 | A1 | 11/2020 | Weber et al. |
| 2020/0375889 | A1 | 12/2020 | Hughes et al. |
| 2020/0384203 | A1 | 12/2020 | Wong et al. |
| 2020/0390724 | A1 | 12/2020 | Arkin et al. |
| 2020/0390725 | A1 | 12/2020 | Arkin et al. |
| 2020/0390907 | A1 | 12/2020 | Sieving et al. |
| 2020/0399656 | A1 | 12/2020 | Neitz et al. |
| 2020/0405808 | A1 | 12/2020 | Hohman |
| 2020/0405898 | A1 | 12/2020 | Laflamme et al. |
| 2021/0000758 | A1 | 1/2021 | Arkin et al. |
| 2021/0008158 | A1 | 1/2021 | Hohman et al. |
| 2021/0008284 | A1 | 1/2021 | Fiedler |
| 2021/0015662 | A1 | 1/2021 | Haffner et al. |
| 2021/0017266 | A1 | 1/2021 | Racine et al. |
| 2021/0022918 | A1 | 1/2021 | Prausnitz et al. |
| 2021/0023173 | A1 | 1/2021 | Yancopoulos |
| 2021/0030945 | A1 | 2/2021 | Cook et al. |
| 2021/0047692 | A1 | 2/2021 | Ghosh et al. |
| 2021/0060258 | A1 | 3/2021 | Mismar et al. |
| 2021/0077645 | A1 | 3/2021 | Mismar et al. |
| 2021/0085745 | A1 | 3/2021 | Innocenti et al. |
| 2021/0100856 | A1 | 4/2021 | Gasmi et al. |
| 2021/0107999 | A1 | 4/2021 | Ehrlich et al. |
| 2021/0113660 | A1 | 4/2021 | Park et al. |
| 2021/0115124 | A1 | 4/2021 | Koenig et al. |
| 2021/0121524 | A1 | 4/2021 | Yancopoulos |
| 2021/0128840 | A1 | 5/2021 | Lilly et al. |
| 2021/0138034 | A1 | 5/2021 | Rudolf et al. |
| 2021/0139576 | A1 | 5/2021 | Osborne et al. |
| 2021/0147542 | A1 | 5/2021 | Giurleo et al. |
| 2021/0161706 | A1 | 6/2021 | Bryant et al. |
| 2021/0161971 | A1 | 6/2021 | Nagy et al. |
| 2021/0169689 | A1 | 6/2021 | Bley et al. |
| 2021/0169896 | A1 | 6/2021 | Zhao et al. |
| 2021/0169975 | A1 | 6/2021 | Rezaei |
| 2021/0170029 | A1 | 6/2021 | Gillespie et al. |
| 2021/0177951 | A1 | 6/2021 | Clube |
| 2021/0178080 | A1 | 6/2021 | Shetty et al. |
| 2021/0196510 | A1 | 7/2021 | De Juan, Jr. et al. |
| 2021/0205410 | A1 | 7/2021 | Vitti et al. |
| 2021/0207166 | A1 | 7/2021 | Layton et al. |
| 2021/0212940 | A1 | 7/2021 | Yamamoto et al. |
| 2021/0220173 | A1 | 7/2021 | Andino et al. |
| 2021/0220435 | A1 | 7/2021 | Brockmeyer et al. |
| 2021/0220436 | A1 | 7/2021 | Kim et al. |
| 2021/0228539 | A1 | 7/2021 | Corson et al. |
| 2021/0228574 | A1 | 7/2021 | Whitcup et al. |
| 2021/0230261 | A1 | 7/2021 | Yonan et al. |
| 2021/0236649 | A1 | 8/2021 | Burian et al. |
| 2021/0260047 | A1 | 8/2021 | Zarnitsyn et al. |
| 2021/0260297 | A1 | 8/2021 | Sawaguchi |
| 2021/0275447 | A1 | 9/2021 | Hong et al. |
| 2021/0283142 | A1 | 9/2021 | Ostrow et al. |
| 2021/0283336 | A1 | 9/2021 | Bryant et al. |
| 2021/0292402 | A1 | 9/2021 | Sawaguchi |
| 2021/0315776 | A1 | 10/2021 | Hang et al. |
| 2021/0322213 | A1 | 10/2021 | Kahook |
| 2021/0322400 | A1 | 10/2021 | Eriksson et al. |
| 2021/0324062 | A1 | 10/2021 | Freichel et al. |
| 2021/0332142 | A1 | 10/2021 | Yan et al. |
| 2021/0338678 | A1 | 11/2021 | Zablow |
| 2021/0340242 | A1 | 11/2021 | Gekkieva et al. |
| 2021/0347852 | A1 | 11/2021 | Olson et al. |
| 2021/0353456 | A1 | 11/2021 | Rotenstreich |
| 2021/0353714 | A1 | 11/2021 | Graham et al. |
| 2021/0355206 | A1 | 11/2021 | Ghosh et al. |
| 2021/0361769 | A1 | 11/2021 | Kauvar et al. |
| 2021/0363231 | A1 | 11/2021 | Famili et al. |
| 2021/0363270 | A1 | 11/2021 | Park et al. |
| 2021/0379012 | A1 | 12/2021 | Corson et al. |
| 2021/0379161 | A1 | 12/2021 | Buice et al. |
| 2021/0393436 | A1 | 12/2021 | Prausnitz et al. |
| 2021/0393649 | A1 | 12/2021 | Ostrow et al. |
| 2021/0393738 | A1 | 12/2021 | Ke |
| 2021/0393883 | A1 | 12/2021 | Shluzas |
| 2021/0395833 | A1 | 12/2021 | Innocenti et al. |
| 2022/0015945 | A1 | 1/2022 | Lerner |
| 2022/0023245 | A1 | 1/2022 | Snyder et al. |
| 2022/0023529 | A1 | 1/2022 | Cook et al. |
| 2022/0025032 | A1 | 1/2022 | Bigelow et al. |
| 2022/0031952 | A1 | 2/2022 | Bryant et al. |
| 2022/0054586 | A1 | 2/2022 | Kim et al. |
| 2022/0071924 | A1 | 3/2022 | Arkin et al. |
| 2022/0079876 | A1 | 3/2022 | Blizzard et al. |
| 2022/0079889 | A1 | 3/2022 | Panigrahi |
| 2022/0087863 | A1 | 3/2022 | Bachelder et al. |
| 2022/0096596 | A1 | 3/2022 | Hohman |
| 2022/0111015 | A1 | 4/2022 | Constable et al. |
| 2022/0112278 | A1 | 4/2022 | Li et al. |
| 2022/0117888 | A1 | 4/2022 | Jiang et al. |
| 2022/0133866 | A1 | 5/2022 | Schraermeyer |
| 2022/0133889 | A1 | 5/2022 | Dranoff et al. |
| 2022/0133908 | A1 | 5/2022 | Rejman et al. |
| 2022/0133981 | A1 | 5/2022 | Dumont et al. |
| 2022/0142924 | A1 | 5/2022 | McDonnell et al. |
| 2022/0143137 | A1 | 5/2022 | Witt et al. |
| 2022/0162296 | A1 | 5/2022 | Lin et al. |
| 2022/0168142 | A1 | 6/2022 | Saim et al. |
| 2022/0175881 | A1 | 6/2022 | Hohman et al. |
| 2022/0175883 | A1 | 6/2022 | Brockmeyer et al. |
| 2022/0220194 | A1 | 7/2022 | Ziegelaar et al. |
| 2022/0226270 | A1 | 7/2022 | Bazan et al. |
| 2022/0227855 | A1 | 7/2022 | Tsiros et al. |
| 2022/0249594 | A1 | 8/2022 | Zhao et al. |
| 2022/0274976 | A1 | 9/2022 | Peters et al. |
| 2022/0280341 | A1 | 9/2022 | Prausnitz et al. |
| 2022/0280608 | A1 | 9/2022 | Pakola et al. |
| 2022/0306732 | A1 | 9/2022 | Bakhle et al. |
| 2022/0331345 | A1 | 10/2022 | Klier et al. |
| 2022/0339108 | A1 | 10/2022 | Jarrett et al. |
| 2022/0339148 | A1 | 10/2022 | Devries et al. |
| 2022/0339360 | A1 | 10/2022 | Young et al. |
| 2022/0347094 | A1 | 11/2022 | Blizzard et al. |
| 2022/0348646 | A1 | 11/2022 | Bigelow et al. |
| 2022/0348678 | A1 | 11/2022 | Kolesnick et al. |
| 2022/0354968 | A1 | 11/2022 | Calias et al. |
| 2022/0356236 | A1 | 11/2022 | Bigelow et al. |

(56) References Cited

U.S. PATENT DOCUMENTS

| | | | |
|---|---|---|---|
| 2022/0362441 | A1 | 11/2022 | Fiedler |
| 2022/0378962 | A1 | 12/2022 | Sias et al. |
| 2022/0379044 | A1 | 12/2022 | Chitnis et al. |
| 2022/0380478 | A1 | 12/2022 | Lederman |
| 2022/0387554 | A1 | 12/2022 | Nelson |
| 2022/0395557 | A1 | 12/2022 | McLaughlin et al. |
| 2022/0401390 | A1 | 12/2022 | Feener et al. |
| 2023/0010108 | A1 | 1/2023 | Zhao et al. |
| 2023/0029307 | A1 | 1/2023 | Ferrara |
| 2023/0047299 | A1 | 2/2023 | Sawaguchi |
| 2023/0052782 | A1 | 2/2023 | Hamlin et al. |
| 2023/0054032 | A1 | 2/2023 | Pandey |
| 2023/0056821 | A1 | 2/2023 | Lu et al. |
| 2023/0063116 | A1 | 3/2023 | Martin et al. |
| 2023/0066364 | A1 | 3/2023 | Eriksson et al. |
| 2023/0078528 | A1 | 3/2023 | Lerner |
| 2023/0080971 | A1 | 3/2023 | Miller |
| 2023/0089914 | A1 | 3/2023 | Kansara et al. |
| 2023/0090539 | A1 | 3/2023 | Haffner et al. |
| 2023/0091723 | A1 | 3/2023 | Weikart et al. |
| 2023/0097413 | A1 | 3/2023 | Behar-Cohen et al. |
| 2023/0103552 | A1 | 4/2023 | Goldberg et al. |
| 2023/0104800 | A1 | 4/2023 | Li et al. |
| 2023/0113993 | A1 | 4/2023 | Bryant et al. |
| 2023/0115871 | A1 | 4/2023 | Zhao et al. |
| 2023/0118774 | A1 | 4/2023 | Blizzard et al. |
| 2023/0126239 | A1 | 4/2023 | Drenser et al. |
| 2023/0126447 | A1 | 4/2023 | Huang et al. |
| 2023/0128124 | A1 | 4/2023 | Yoshida |
| 2023/0130754 | A1 | 4/2023 | Kim et al. |
| 2023/0135092 | A1 | 5/2023 | Eaton et al. |
| 2023/0136844 | A1 | 5/2023 | Lindblad et al. |
| 2023/0149629 | A1 | 5/2023 | Hawson et al. |
| 2023/0157533 | A1 | 5/2023 | Chang et al. |
| 2023/0157869 | A1 | 5/2023 | Andino et al. |
| 2023/0165931 | A1 | 6/2023 | Zhao et al. |
| 2023/0166092 | A1 | 6/2023 | Unger et al. |
| 2023/0167170 | A1 | 6/2023 | Pham et al. |
| 2023/0181357 | A1 | 6/2023 | Pinchuk et al. |
| 2023/0181686 | A1 | 6/2023 | Fu et al. |
| 2023/0201371 | A1 | 6/2023 | Ciulla et al. |
| 2023/0201387 | A1 | 6/2023 | Shieu et al. |
| 2023/0226280 | A1 | 7/2023 | Lerner |
| 2023/0233373 | A1 | 7/2023 | Chang |
| 2023/0233375 | A1 | 7/2023 | Patel et al. |
| 2023/0248806 | A1 | 8/2023 | Sigl |
| 2023/0248855 | A1 | 8/2023 | Ludwig et al. |
| 2023/0248898 | A1 | 8/2023 | Cook et al. |
| 2023/0256107 | A1 | 8/2023 | Kelley, Jr. et al. |
| 2023/0263957 | A1 | 8/2023 | Taha et al. |
| 2023/0265199 | A1 | 8/2023 | Sapieha et al. |
| 2023/0270670 | A1 | 8/2023 | Yoon et al. |
| 2023/0271871 | A1 | 8/2023 | Chillon et al. |
| 2023/0271999 | A1 | 8/2023 | Iyer et al. |
| 2023/0277375 | A1 | 9/2023 | Egloff et al. |
| 2023/0279090 | A1 | 9/2023 | Dengl et al. |
| 2023/0285282 | A1 | 9/2023 | Blizzard et al. |
| 2023/0285678 | A1 | 9/2023 | Sakhrani et al. |
| 2023/0293731 | A1 | 9/2023 | Fotin-Mleczek et al. |
| 2023/0295266 | A1 | 9/2023 | Vitti et al. |
| 2023/0302085 | A1 | 9/2023 | Vitti et al. |
| 2023/0302156 | A1 | 9/2023 | Jiang et al. |
| 2023/0303305 | A1 | 9/2023 | Abrams et al. |
| 2023/0310734 | A1 | 10/2023 | Tono et al. |
| 2023/0312697 | A1 | 10/2023 | Sikorski et al. |
| 2023/0317288 | A1 | 10/2023 | Li et al. |
| 2023/0322911 | A1 | 10/2023 | Blumenkranz et al. |
| 2023/0330323 | A1 | 10/2023 | Dominguez et al. |
| 2023/0338483 | A1 | 10/2023 | Schraermeyer |
| 2023/0338599 | A1 | 10/2023 | Olson et al. |
| 2023/0355544 | A1 | 11/2023 | Gong et al. |
| 2023/0355885 | A1 | 11/2023 | Shetty et al. |
| 2023/0363941 | A1 | 11/2023 | Andino et al. |
| 2023/0364086 | A1 | 11/2023 | Campbell et al. |
| 2023/0364349 | A1 | 11/2023 | Huang et al. |
| 2023/0372538 | A1 | 11/2023 | Bee et al. |
| 2023/0381183 | A1 | 11/2023 | Zhan et al. |
| 2023/0398233 | A1 | 12/2023 | Ni et al. |
| 2023/0414602 | A1 | 12/2023 | Park |
| 2023/0414677 | A1 | 12/2023 | Nagy et al. |
| 2023/0414770 | A1 | 12/2023 | Stark et al. |
| 2023/0414788 | A1 | 12/2023 | Bee et al. |
| 2023/0414800 | A1 | 12/2023 | Shieu et al. |
| 2023/0414859 | A1 | 12/2023 | Cook et al. |
| 2023/0416351 | A1 | 12/2023 | Clemens et al. |
| 2023/0416353 | A1 | 12/2023 | Osborne et al. |
| 2024/0000889 | A1 | 1/2024 | Rezaei |
| 2024/0002489 | A1 | 1/2024 | Ziegelaar et al. |
| 2024/0058461 | A1 | 2/2024 | Iyer |

FOREIGN PATENT DOCUMENTS

| | | | |
|---|---|---|---|
| AU | 2006251769 | B2 | 7/2009 |
| AU | 2010320885 | A1 | 5/2012 |
| AU | 2010320885 | B2 | 3/2013 |
| AU | 201616239 | | 12/2016 |
| BE | 853718 | A | 10/1977 |
| CA | 87137 | | 7/1999 |
| CA | 2680335 | A1 | 9/2008 |
| CA | 2773015 | A1 | 4/2011 |
| CA | 2781483 | A1 | 5/2011 |
| CA | 167018 | | 2/2017 |
| CA | 170630 | | 2/2017 |
| CA | 175995 | | 9/2018 |
| CA | 180221 | A | 4/2019 |
| CA | 3096847 | A1 | 10/2019 |
| CL | 199501972 | | 12/1995 |
| CL | 20003263 | | 11/2000 |
| CL | 200003263 | | 11/2000 |
| CL | 20022008 | | 9/2002 |
| CL | 20022009 | | 9/2002 |
| CL | 20022010 | | 9/2002 |
| CL | 20022012 | | 9/2002 |
| CL | 20022013 | | 9/2002 |
| CL | 200400771 | | 4/2004 |
| CL | 200403345 | | 12/2004 |
| CL | 50273 | B1 | 1/2005 |
| CL | 47361 | B1 | 7/2005 |
| CL | 200703300 | | 6/2008 |
| CL | 200703301 | | 6/2008 |
| CL | 201000322 | | 4/2010 |
| CL | 201102772 | | 2/2012 |
| CL | 201300288 | | 1/2013 |
| CL | 201300289 | | 1/2013 |
| CL | 201800652 | | 3/2018 |
| CL | 202103018 | | 4/2020 |
| CL | 202001590 | | 8/2020 |
| CL | 202002325 | | 8/2020 |
| CL | 202002869 | | 11/2020 |
| CL | 202003174 | | 12/2020 |
| CL | 202103017 | | 12/2020 |
| CL | 202103019 | | 11/2021 |
| CL | 202103227 | | 12/2021 |
| CL | 202401553 | | 11/2022 |
| CL | 202401555 | | 11/2022 |
| CL | 202301422 | | 5/2023 |
| CL | 202302511 | | 2/2024 |
| CL | 202302512 | | 2/2024 |
| CL | 202302513 | | 2/2024 |
| CL | 202302514 | | 2/2024 |
| CL | 202302515 | | 2/2024 |
| CL | 202302516 | | 2/2024 |
| CL | 202302517 | | 2/2024 |
| CN | 1186699 | A | 7/1998 |
| CN | 1197398 | A | 10/1998 |
| CN | 1649638 | A | 8/2005 |
| CN | 2748094 | Y | 12/2005 |
| CN | 100540077 | C | 9/2009 |
| CN | 201356870 | Y | 12/2009 |
| CN | 202113444 | U | 1/2012 |
| CN | 102481418 | A | 5/2012 |
| CN | 102946930 | A | 2/2013 |
| CN | 203227124 | U | 10/2013 |
| CN | 204501944 | U | 7/2015 |

(56) References Cited

FOREIGN PATENT DOCUMENTS

CN 204972542 U 1/2016
CN 105381520 A 3/2016
CN 105709308 A 6/2016
CN 205434581 U 8/2016
CN 106215286 A 12/2016
CN 106975125 A 7/2017
CN 107205843 A 9/2017
CN 108025137 A 5/2018
CN 304679488 6/2018
CN 109172952 A 1/2019
CN 109310821 A 2/2019
CN 109641107 A 4/2019
CN 110115657 8/2019
CN 110913926 A 3/2020
CN 111249062 6/2020
CN 213099452 5/2021
CN 112972828 6/2021
CN 306672665 S 7/2021
CN 306732751 S 8/2021
CN 306748066 S 8/2021
CN 215350708 12/2021
CN 215350709 12/2021
CN 215350710 12/2021
CN 109310815 6/2022
CN 110913926 7/2022
CN 115054777 9/2022
CN 109172952 9/2023
CN 116710137 9/2023
CO 11784-0001 12/2020
DE 68509572 9/1985
DE 19856167 C1 5/2000
DE 10110126 A1 9/2002
DE 202005020468 U1 2/2006
DE 102005008065 A1 8/2006
DK 172984 B1 11/1999
DM 212509 4/2020
EP 0208975 A2 1/1987
EP 0901380 A1 3/1999
EP 0904792 A2 3/1999
EP 1019120 A1 7/2000
EP 1061974 A1 12/2000
EP 0846072 B1 5/2001
EP 1061975 B1 2/2004
EP 0971749 B1 7/2004
EP 000221551-0001 9/2004
EP 0937477 B1 11/2004
EP 1409046 B1 3/2005
EP 0976415 B1 5/2005
EP 1559443 A1 8/2005
EP 1568389 A1 8/2005
EP 000494356-0001 3/2006
EP 000494356-0002 3/2006
EP 000494356-0003 3/2006
EP 000508049-0001 3/2006
EP 1702636 A1 9/2006
EP 1675632 B1 9/2007
EP 1829577 A2 9/2007
EP 1525015 B1 10/2007
EP 1855742 A1 11/2007
EP 1885414 A1 2/2008
EP 1071487 B1 3/2008
EP 1924309 A1 5/2008
EP 1728529 B1 7/2008
EP 1818069 B1 9/2008
EP 1704887 B1 10/2008
EP 1973592 A2 10/2008
EP 1730999 12/2008
EP 1855742 B1 12/2008
EP 1605847 B1 9/2009
EP 2121085 A1 11/2009
EP 2134391 A2 12/2009
EP 1488818 B1 3/2010
EP 1735014 B1 8/2010
EP 2253548 A1 11/2010
EP 2253549 A1 11/2010
EP 2292286 A1 3/2011
EP 2371406 10/2011
EP 2397174 A2 12/2011
EP 1885414 A4 4/2012
EP 2453928 A1 5/2012
EP 1885414 B1 11/2012
EP 2524693 A1 11/2012
EP 2552349 A1 2/2013
EP 2593369 A1 5/2013
EP 2627377 A1 8/2013
EP 1647285 11/2013
EP 002416487-0001 3/2014
EP 2482890 B1 12/2014
EP 2253549 B1 3/2015
EP 2555820 B1 3/2015
EP 2846754 A1 3/2015
EP 2854762 A1 4/2015
EP 2862587 A1 4/2015
EP 1940476 B1 5/2015
EP 2869813 A1 5/2015
EP 2436407 B1 6/2015
EP 2436408 B1 6/2015
EP 1433705 B1 7/2015
EP 2445552 10/2015
EP 2939649 A1 11/2015
EP 2488232 B1 1/2016
EP 2601979 5/2016
EP 3021900 A1 5/2016
EP 1728529 B2 7/2016
EP 1019120 B1 8/2016
EP 3056223 8/2016
EP 3057633 A1 8/2016
EP 2925392 B1 4/2017
EP 3160471 A1 5/2017
EP 3162401 A2 5/2017
EP 1973592 B1 6/2017
EP 3192549 A1 7/2017
EP 2944583 B1 8/2017
EP 3199189 A1 8/2017
EP 3202389 A1 8/2017
EP 3202447 A1 8/2017
EP 3213786 A1 9/2017
EP 2550043 B1 10/2017
EP 2666510 B1 10/2017
EP 2134391 B1 12/2017
EP 3108902 7/2018
EP 2968729 8/2018
EP 3377040 9/2018
EP 2869813 B1 11/2018
EP 3056224 11/2018
EP 2451511 B1 1/2019
EP 3424547 1/2019
EP 2701773 B1 2/2019
EP 3437678 2/2019
EP 3452103 A1 3/2019
EP 3470058 4/2019
EP 2627377 B1 8/2019
EP 3539597 A1 9/2019
EP 3124005 12/2019
EP 3581185 A1 12/2019
EP 3065761 B1 1/2020
EP 3600442 A1 2/2020
EP 3630043 4/2020
EP 3630062 A2 4/2020
EP 3057633 B1 5/2020
EP 3403622 B1 5/2020
EP 3656373 A1 5/2020
EP 2701778 B1 7/2020
EP 3226895 7/2020
EP 3687464 A1 8/2020
EP 3687599 8/2020
EP 3471780 B1 10/2020
EP 3738580 A1 11/2020
EP 3763384 1/2021
EP 3452013 B1 2/2021
EP 3536310 4/2021
EP 3381444 5/2021
EP 2991706 B1 6/2021
EP 3782807 6/2021

(56) References Cited

FOREIGN PATENT DOCUMENTS

| | | | |
|---|---|---|---|
| EP | 3679922 | | 7/2021 |
| EP | 3291812 | B1 | 9/2021 |
| EP | 3484531 | | 11/2021 |
| EP | 3685826 | | 11/2021 |
| EP | 3193829 | B1 | 12/2021 |
| EP | 3656373 | | 2/2022 |
| EP | 3777834 | | 2/2022 |
| EP | 3472317 | B1 | 3/2022 |
| EP | 4025272 | | 7/2022 |
| EP | 4028128 | A1 | 7/2022 |
| EP | 4031208 | | 7/2022 |
| EP | 2604295 | | 9/2022 |
| EP | 3116553 | | 9/2022 |
| EP | 4065150 | A1 | 10/2022 |
| EP | 2887982 | B1 | 11/2022 |
| EP | 3897595 | B1 | 3/2023 |
| EP | 4153494 | | 3/2023 |
| EP | 2760509 | | 4/2023 |
| EP | 3380040 | B1 | 4/2023 |
| EP | 3685828 | B1 | 4/2023 |
| EP | 3858405 | | 4/2023 |
| EP | 4159220 | A1 | 4/2023 |
| EP | 4201441 | | 6/2023 |
| EP | 3384049 | B1 | 8/2023 |
| EP | 4218862 | | 8/2023 |
| EP | 4225235 | A1 | 8/2023 |
| EP | 4245312 | A1 | 9/2023 |
| EP | 4245336 | A1 | 9/2023 |
| EP | 4251204 | A1 | 10/2023 |
| EP | 4255530 | A1 | 10/2023 |
| EP | 4257509 | | 10/2023 |
| EP | 4262894 | | 10/2023 |
| EP | 3233056 | B1 | 11/2023 |
| EP | 3681448 | B1 | 11/2023 |
| EP | 3634543 | | 6/2024 |
| FR | 711644 | A | 9/1931 |
| FR | 1216753 | A | 4/1960 |
| FR | 1412547 | A | 10/1965 |
| FR | 2536285 | A1 | 5/1984 |
| FR | 2561925 | A3 | 10/1985 |
| FR | D053933-0001 | | 10/2000 |
| GB | 1230522 | A | 5/1971 |
| GB | 1550308 | A | 8/1979 |
| IL | 70802 | | 6/2023 |
| IN | 342357001 | | 4/2021 |
| IN | 342359001 | | 4/2021 |
| IN | 356808001 | | 1/2022 |
| IN | 365804001 | | 1/2022 |
| IN | 342358001 | | 4/2022 |
| IT | MI20102322 | A1 | 6/2012 |
| JP | S4824842 | U | 3/1973 |
| JP | S54-117736 | A | 9/1978 |
| JP | 55-107113 | A | 8/1980 |
| JP | 60-175249 | A | 9/1985 |
| JP | 7-7650 | | 2/1995 |
| JP | H07244442 | A | 9/1995 |
| JP | 8-164206 | A | 6/1996 |
| JP | H11151301 | A | 6/1999 |
| JP | 2000-197700 | A | 7/2000 |
| JP | 2000202027 | A | 7/2000 |
| JP | 2001-218843 | A | 8/2001 |
| JP | 2001-526097 | | 12/2001 |
| JP | 2003-199828 | A | 7/2003 |
| JP | 2004-500201 | A | 1/2004 |
| JP | 2004-49726 | A | 2/2004 |
| JP | 2005-312699 | A | 11/2005 |
| JP | 2006-26280 | A | 2/2006 |
| JP | 4191409 | B2 | 12/2008 |
| JP | 2008307237 | A | 12/2008 |
| JP | 2009011481 | A | 1/2009 |
| JP | 2012-85813 | A | 5/2012 |
| JP | 2012179240 | A | 9/2012 |
| JP | 2012528642 | A | 11/2012 |
| JP | 2012-245180 | A | 12/2012 |
| JP | 5163882 | | 3/2013 |
| JP | 2013511309 | A | 4/2013 |
| JP | 2014-4041 | A | 1/2014 |
| JP | 2014515683 | A | 7/2014 |
| JP | 5718157 | B2 | 5/2015 |
| JP | 2015-123296 | A | 7/2015 |
| JP | 5744927 | | 7/2015 |
| JP | 2015-523867 | A | 8/2015 |
| JP | D1531421 | S | 8/2015 |
| JP | 2015-171514 | | 10/2015 |
| JP | 5801314 | B2 | 10/2015 |
| JP | 5907874 | B2 | 4/2016 |
| JP | D1552403 | S | 6/2016 |
| JP | 2016124594 | A | 7/2016 |
| JP | 5978742 | B2 | 8/2016 |
| JP | 2016-538960 | A | 12/2016 |
| JP | 2017-60837 | | 3/2017 |
| JP | 6144264 | | 6/2017 |
| JP | 6313038 | | 4/2018 |
| JP | D1646523 | S | 11/2019 |
| JP | 2020522351 | A | 7/2020 |
| JP | 6781546 | | 11/2020 |
| JP | 6920269 | | 8/2021 |
| JP | D1700933 | S | 11/2021 |
| JP | D1701001 | S | 11/2021 |
| JP | 2023506180 | | 2/2023 |
| JP | 7244442 | | 3/2023 |
| JP | 2023071962 | | 5/2023 |
| JP | 2023550458 | | 12/2023 |
| KR | 20050004800 | A | 1/2005 |
| KR | 100721549 | B1 | 5/2007 |
| KR | 1020110022607 | A | 2/2014 |
| KR | 10-1510680 | B1 | 4/2015 |
| KR | 20150119092 | A | 10/2015 |
| KR | 101774823 | | 9/2017 |
| KR | 102232708 | | 3/2021 |
| KR | 102288287 | | 8/2021 |
| KR | 102299177 | | 9/2021 |
| KR | 102341670 | | 12/2021 |
| KR | 20220085906 | | 6/2022 |
| MX | 03007940 | A | 10/2004 |
| RU | 2488410 | C2 | 7/2013 |
| RU | 2012125349 | A | 12/2013 |
| SE | D060555-0002 | | 1/2002 |
| SG | 30202008659 | T | 12/2020 |
| SG | 30202008662 | P | 12/2020 |
| SG | 30202008663 | | 12/2020 |
| TW | M261222 | U | 4/2005 |
| TW | 201215424 | A | 4/2012 |
| TW | 201600133 | A | 1/2016 |
| TW | D187080 | S | 12/2017 |
| TW | 1632920 | | 8/2018 |
| TW | 201831212 | A | 9/2018 |
| TW | 201900234 | A | 1/2019 |
| TW | 1720632 | | 3/2021 |
| TW | D215156 | S | 11/2021 |
| TW | 202144033 | A | 12/2021 |
| TW | D215855 | S | 12/2021 |
| TW | D216479 | S | 1/2022 |
| TW | D216480 | S | 1/2022 |
| TW | 202237181 | | 10/2022 |
| VN | 3-0028936-000 | | 12/2017 |
| VN | 3-0028632-000 | | 7/2018 |
| WO | 8601728 | A2 | 3/1986 |
| WO | WO-9320784 | A1 | 10/1993 |
| WO | 9504563 | A1 | 2/1995 |
| WO | 9512418 | A1 | 5/1995 |
| WO | 9530444 | | 11/1995 |
| WO | 9626754 | A2 | 9/1996 |
| WO | WO-9630046 | A1 | 10/1996 |
| WO | 9701362 | A2 | 1/1997 |
| WO | 9708054 | A1 | 3/1997 |
| WO | 9709080 | A1 | 3/1997 |
| WO | 9744068 | A1 | 11/1997 |
| WO | 9805366 | | 2/1998 |
| WO | 9819715 | A1 | 5/1998 |
| WO | 9856438 | A1 | 12/1998 |
| WO | 9856439 | A1 | 12/1998 |
| WO | 9915215 | A1 | 4/1999 |
| WO | 9927971 | A2 | 6/1999 |

(56) References Cited

FOREIGN PATENT DOCUMENTS

| | | | |
|---|---|---|---|
| WO | 9945984 | A1 | 9/1999 |
| WO | 9945985 | A1 | 9/1999 |
| WO | 0154756 | | 8/2001 |
| WO | 0178812 | A1 | 10/2001 |
| WO | 0195959 | A1 | 12/2001 |
| WO | 02072157 | A1 | 9/2002 |
| WO | 03004080 | A1 | 1/2003 |
| WO | 03057285 | A2 | 7/2003 |
| WO | 03077976 | A1 | 9/2003 |
| WO | 03080160 | A1 | 10/2003 |
| WO | 03097133 | A1 | 11/2003 |
| WO | 03057285 | A3 | 12/2003 |
| WO | 2004032996 | A2 | 4/2004 |
| WO | 2004035113 | A2 | 4/2004 |
| WO | 2004032996 | A3 | 7/2004 |
| WO | 2005032627 | A1 | 4/2005 |
| WO | 2005067984 | A1 | 7/2005 |
| WO | 2006047325 | A1 | 5/2006 |
| WO | 2006089734 | A1 | 8/2006 |
| WO | 2006130098 | A1 | 12/2006 |
| WO | 2006130100 | A1 | 12/2006 |
| WO | 2007002052 | A2 | 1/2007 |
| WO | WO-2007011873 | A2 | 1/2007 |
| WO | 2007024957 | A1 | 3/2007 |
| WO | 2007035621 | A1 | 3/2007 |
| WO | 2007083034 | A2 | 7/2007 |
| WO | WO-2007084765 | A2 | 7/2007 |
| WO | WO-2007087457 | A2 | 8/2007 |
| WO | WO-2007112675 | A1 | 10/2007 |
| WO | 2008051561 | A2 | 5/2008 |
| WO | 2008058666 | A1 | 5/2008 |
| WO | 2008058668 | A1 | 5/2008 |
| WO | WO-2008063932 | A2 | 5/2008 |
| WO | 2008083875 | A1 | 7/2008 |
| WO | WO-2008101985 | A2 | 8/2008 |
| WO | 2008110890 | A1 | 9/2008 |
| WO | 2008112472 | A2 | 9/2008 |
| WO | 2008112472 | A3 | 11/2008 |
| WO | 2009007997 | A2 | 1/2009 |
| WO | 2009092430 | A1 | 7/2009 |
| WO | WO-2009086112 | A2 | 7/2009 |
| WO | WO-2009089409 | A2 | 7/2009 |
| WO | WO-2009155724 | A2 | 12/2009 |
| WO | WO-2010081838 | A2 | 7/2010 |
| WO | WO-2010085542 | A2 | 7/2010 |
| WO | WO-2010088548 | A1 | 8/2010 |
| WO | 2010127449 | A1 | 11/2010 |
| WO | WO-2010127029 | A1 | 11/2010 |
| WO | 2010149466 | A2 | 12/2010 |
| WO | 2011006877 | A1 | 1/2011 |
| WO | 2011032513 | A1 | 3/2011 |
| WO | 2011037437 | A2 | 3/2011 |
| WO | 2011038487 | A1 | 4/2011 |
| WO | 2011039211 | A1 | 4/2011 |
| WO | 2011057335 | | 5/2011 |
| WO | 2011061313 | A1 | 5/2011 |
| WO | 2011073174 | A1 | 6/2011 |
| WO | 2011073176 | A1 | 6/2011 |
| WO | 2011081867 | A2 | 7/2011 |
| WO | WO-2011085288 | A2 | 7/2011 |
| WO | 2011115428 | A2 | 9/2011 |
| WO | 2011117878 | A1 | 9/2011 |
| WO | 2011125133 | A1 | 10/2011 |
| WO | 2011133097 | A1 | 10/2011 |
| WO | 2011137437 | A2 | 11/2011 |
| WO | 2012007056 | A1 | 1/2012 |
| WO | WO-2012003437 | A1 | 1/2012 |
| WO | WO-2012019176 | A2 | 2/2012 |
| WO | 2012049141 | A1 | 4/2012 |
| WO | WO-2012055884 | A1 | 5/2012 |
| WO | WO-2012097019 | A1 | 7/2012 |
| WO | 2012118687 | A1 | 9/2012 |
| WO | 2012125132 | A1 | 9/2012 |
| WO | 2012148717 | A1 | 11/2012 |
| WO | 2012158095 | A1 | 11/2012 |
| WO | WO-2012149040 | A2 | 11/2012 |
| WO | 2012/166287 | A1 | 12/2012 |
| WO | 2013028537 | A2 | 2/2013 |
| WO | 2013034986 | A2 | 3/2013 |
| WO | WO-2012019139 | A9 | 3/2013 |
| WO | 2013048310 | A1 | 4/2013 |
| WO | WO-2013126799 | A1 | 8/2013 |
| WO | WO-2013151904 | A1 | 10/2013 |
| WO | 2013178771 | A1 | 12/2013 |
| WO | 2013184270 | A1 | 12/2013 |
| WO | 2014005728 | A1 | 1/2014 |
| WO | 2014/033184 | | 3/2014 |
| WO | WO-2014033184 | A1 | 3/2014 |
| WO | WO-2014036009 | A1 | 3/2014 |
| WO | 2014049712 | A1 | 4/2014 |
| WO | 2014049714 | A1 | 4/2014 |
| WO | 2014068283 | A2 | 5/2014 |
| WO | 2014073618 | A1 | 5/2014 |
| WO | WO-2014074823 | A1 | 5/2014 |
| WO | 2014102987 | A1 | 7/2014 |
| WO | WO-2014105978 | A1 | 7/2014 |
| WO | 2014162551 | A1 | 10/2014 |
| WO | 2014187779 | A1 | 11/2014 |
| WO | WO-2014179698 | A2 | 11/2014 |
| WO | 2014/023181 | A1 | 12/2014 |
| WO | WO-2014203182 | A1 | 12/2014 |
| WO | WO-2014203183 | A1 | 12/2014 |
| WO | 2015007808 | A1 | 1/2015 |
| WO | 2015007811 | A1 | 1/2015 |
| WO | WO-2015006734 | A1 | 1/2015 |
| WO | 2015/032800 | A2 | 3/2015 |
| WO | 2015033280 | A1 | 3/2015 |
| WO | 2015045180 | A1 | 4/2015 |
| WO | 2015047758 | A2 | 4/2015 |
| WO | 2015055608 | A1 | 4/2015 |
| WO | WO-2015069668 | A1 | 5/2015 |
| WO | WO-2015073895 | A1 | 5/2015 |
| WO | 2015047758 | A3 | 7/2015 |
| WO | 2015157484 | A1 | 10/2015 |
| WO | 2015164413 | A1 | 10/2015 |
| WO | WO-2015164626 | A2 | 10/2015 |
| WO | WO-2015168619 | A1 | 11/2015 |
| WO | WO-2015195842 | A1 | 12/2015 |
| WO | WO-2015196085 | A2 | 12/2015 |
| WO | 2016033701 | A1 | 3/2016 |
| WO | WO-2016042162 | A1 | 3/2016 |
| WO | 2016052037 | A1 | 4/2016 |
| WO | 2016068333 | A1 | 5/2016 |
| WO | WO-2016073918 | A1 | 5/2016 |
| WO | 2016094387 | A2 | 6/2016 |
| WO | 2016169718 | A1 | 10/2016 |
| WO | 2016191535 | A2 | 12/2016 |
| WO | 2016193620 | A1 | 12/2016 |
| WO | 2016193624 | A1 | 12/2016 |
| WO | 2016199133 | A1 | 12/2016 |
| WO | 2017012789 | A1 | 1/2017 |
| WO | WO-2017014630 | A1 | 1/2017 |
| WO | 2017027876 | A1 | 2/2017 |
| WO | 2017030195 | A1 | 2/2017 |
| WO | WO-2017025928 | A2 | 2/2017 |
| WO | WO-2017046358 | A1 | 3/2017 |
| WO | 2017055462 | A1 | 4/2017 |
| WO | 2017057477 | A1 | 4/2017 |
| WO | 2017062304 | A1 | 4/2017 |
| WO | 2017062407 | A1 | 4/2017 |
| WO | 2017062930 | A1 | 4/2017 |
| WO | 2017062931 | A1 | 4/2017 |
| WO | 2017062933 | A1 | 4/2017 |
| WO | 2017087798 | A1 | 5/2017 |
| WO | 2017087871 | A1 | 5/2017 |
| WO | 2017103954 | A1 | 6/2017 |
| WO | 2017126550 | A1 | 7/2017 |
| WO | WO-2017120601 | A1 | 7/2017 |
| WO | 2017129685 | A1 | 8/2017 |
| WO | 2017139375 | A1 | 8/2017 |
| WO | 2017139573 | A1 | 8/2017 |
| WO | 2017158805 | A1 | 9/2017 |
| WO | WO-2017158366 | A2 | 9/2017 |
| WO | 2017180480 | A1 | 10/2017 |

(56) References Cited

FOREIGN PATENT DOCUMENTS

| | | | |
|---|---|---|---|
| WO | 2017191306 | A1 | 11/2017 |
| WO | 2017204787 | A1 | 11/2017 |
| WO | WO-2018031913 | A1 | 2/2018 |
| WO | 2018085759 | A1 | 5/2018 |
| WO | 2018085768 | A2 | 5/2018 |
| WO | WO-2018111862 | A1 | 6/2018 |
| WO | 2018141634 | A1 | 8/2018 |
| WO | 2018204140 | A1 | 11/2018 |
| WO | 2018215580 | A1 | 11/2018 |
| WO | 2018217995 | A1 | 11/2018 |
| WO | 2018218013 | A2 | 11/2018 |
| WO | 2018224640 | A1 | 12/2018 |
| WO | 2018224644 | A1 | 12/2018 |
| WO | 2018232408 | A1 | 12/2018 |
| WO | WO-2019040397 | A1 | 2/2019 |
| WO | WO-2019108770 | A1 | 6/2019 |
| WO | WO-2019175727 | A1 | 9/2019 |
| WO | 2019197361 | A1 | 10/2019 |
| WO | WO-2019217927 | A1 | 11/2019 |
| WO | WO-2020160256 | A1 | 8/2020 |
| WO | WO-2020180951 | A1 | 9/2020 |
| WO | 2020247686 | | 12/2020 |
| WO | WO-2021046070 | A1 | 3/2021 |
| WO | WO-2021048779 | A2 | 3/2021 |
| WO | WO-2021050649 | A1 | 3/2021 |
| WO | WO-2021072265 | A1 | 4/2021 |
| WO | WO-2021108255 | A1 | 6/2021 |
| WO | WO-2021119544 | A1 | 6/2021 |
| WO | WO-2021168218 | A1 | 8/2021 |
| WO | WO-2021178899 | A1 | 9/2021 |
| WO | WO-2021183555 | A1 | 9/2021 |
| WO | WO-2021195163 | A1 | 9/2021 |
| WO | WO-2021240488 | A1 | 12/2021 |
| WO | WO-2021252647 | A1 | 12/2021 |
| WO | WO-2021252962 | A1 | 12/2021 |
| WO | WO-2022005100 | A1 | 1/2022 |
| WO | WO-2022011323 | A1 | 1/2022 |
| WO | WO-2022013172 | A1 | 1/2022 |
| WO | WO-2022056326 | A1 | 3/2022 |
| WO | WO-2022066788 | A1 | 3/2022 |
| WO | WO-2022067330 | A1 | 3/2022 |
| WO | WO-2022076549 | A1 | 4/2022 |
| WO | WO-2022076591 | A1 | 4/2022 |
| WO | WO-2022076938 | A1 | 4/2022 |
| WO | WO-2022093818 | A1 | 5/2022 |
| WO | WO-2022094340 | A1 | 5/2022 |
| WO | WO-2022111379 | A1 | 6/2022 |
| WO | WO-2022112957 | A1 | 6/2022 |
| WO | WO-2022131789 | A1 | 6/2022 |
| WO | WO-2022175601 | A1 | 8/2022 |
| WO | WO-2022183418 | A1 | 9/2022 |
| WO | WO-2022201084 | A1 | 9/2022 |
| WO | WO-2022204374 | A1 | 9/2022 |
| WO | WO-2022212360 | A1 | 10/2022 |
| WO | WO-2022217110 | A1 | 10/2022 |
| WO | WO-2022220602 | A1 | 10/2022 |
| WO | WO-2022221315 | A1 | 10/2022 |
| WO | WO-2022221395 | A1 | 10/2022 |
| WO | WO-2022221537 | A1 | 10/2022 |
| WO | WO-2022223140 | A1 | 10/2022 |
| WO | WO-2022226347 | A1 | 10/2022 |
| WO | WO-2022229932 | A1 | 11/2022 |
| WO | WO-2022232790 | A1 | 11/2022 |
| WO | WO-2022246476 | A1 | 11/2022 |
| WO | 2022272257 | | 12/2022 |
| WO | WO-2022251710 | A2 | 12/2022 |
| WO | WO-2022268048 | A1 | 12/2022 |
| WO | WO-2023014892 | A1 | 2/2023 |
| WO | WO-2023039458 | A1 | 3/2023 |
| WO | WO-2023041697 | A1 | 3/2023 |
| WO | WO-2023047375 | A2 | 3/2023 |
| WO | WO-2023054503 | A1 | 4/2023 |
| WO | WO-2023081528 | A1 | 5/2023 |
| WO | WO-2023091955 | A1 | 5/2023 |
| WO | 2023114123 | | 6/2023 |
| WO | WO-2023130081 | A1 | 7/2023 |
| WO | WO-2023133058 | A2 | 7/2023 |
| WO | WO-2023150566 | A1 | 8/2023 |
| WO | WO-2023153535 | A1 | 8/2023 |
| WO | WO-2023158990 | A1 | 8/2023 |
| WO | WO-2023171360 | A1 | 9/2023 |
| WO | WO-2023172585 | A1 | 9/2023 |
| WO | WO-2023173055 | A2 | 9/2023 |
| WO | WO-2023173088 | A1 | 9/2023 |
| WO | WO-2023173093 | A1 | 9/2023 |
| WO | WO-2023175549 | A1 | 9/2023 |
| WO | WO-2023177691 | A1 | 9/2023 |
| WO | WO-2023180450 | A1 | 9/2023 |
| WO | WO-2022260939 | A9 | 10/2023 |
| WO | WO-2023212273 | A1 | 11/2023 |

OTHER PUBLICATIONS

International Search Report in International Patent Application No. PCT/USUS2022/076090, dated Dec. 6, 2022, 3 pages.

Sassalos et al., "Prefilled syringes for intravitreal drug delivery", Clinical Ophthalmology, vol. 13, pp. 701-706, doi: 10.2147/OPTH. S169044, Apr. 23, 2019.

Schargus et al., "Comparison of Syringes With Intravitreal Anti-VEGF Drugs: Particle Burden and Protein Aggregates in Brolucizumab, Aflibercept and Bevacizumab", Translational Vision Science Technoloy, vol. 10, No. 9, p. 21, doi: 10.1167/tvst.10.9.21, Aug. 18, 2021.

Subhi et al., "Prefilled syringes for intravitreal injection reduce preparation time", Danish Medical Journal, PMID: 27034182, Apr. 1, 2016.

Parenky et al., "Container Closure and Delivery Considerations for Intravitreal Drug Administration", AAPS PharmSciTech. vol. 22, No. 3, doi: 10.1208/s12249-021-01949-4, Mar. 11, 2021.

Colucciello, Michael, "Prefilled Syringe Delivery of Intravitreal Anti-VEGF Medications", 9th paragraph, XP002808066, retrieved from the Internet: URL:https://www.retinalphysician.com/issue s/2019/march-2019/prefilled-syringe-delive ry-of-intravitreal-anti-veretinalphysician.com, Mar. 1, 2019.

"Regeneron 2019 Annual Report", regenron.com, 2019, Slides 14 and 14, XP002808067, retrieved from the Internet: URL:https://investor.regeneron.com/static•files/d2933d3d-f409-47e4-a637-c5ca52cf3b87, Published 2019, Retrieved Nov. 23, 2022.

Philip et al., "The Impact of Prefilled Syringes on Endophthalmitis Following Intravitreal Injection of Ranibizumab", American Journal of Ophthalmology United States, vol. 199, First Paragraph, DOI: 10.1016/J.AJO.2018.11.023, Feb. 28, 2019.

Search Report in Eurasian Patent Application No. 202391326, dated Sep. 15, 2023, 6 pages (in Russian with English translation).

Chinese Office Action dated Jun. 24, 2022, in counterpart Chinese Patent Application No. 201880080564.7 (9 pages, in Chinese).

Taiwanese Search Report for Application No. 112302459, dated Oct. 26, 2023, 4 pages.

Office Action in Colombian Application No. NC2020/0007231, dated Apr. 13, 2023, 38 pages (in Spanish with English.

Office Action in Colombian Application No. NC2023/0001752, dated Apr. 18, 2023, 33 pages (in Spanish with English translation).

Office Action in Colombian Application No. NC/2023/0001925, dated Apr. 18, 2023, 17 pages (in Spanish with English translation).

Office Action in Colombian Application No. NC2020/0001926, dated Jun. 23, 2023, 11 pages (in Spanish with English translation).

U.S. Appl. No. 62/467,065, filed Mar. 3, 2017 (9 pages).

International Preliminary Report on Patentability dated May 6, 2021, in International Patent Application No. PCT/US2020/036200 (12 pages, in English).

Accura Xtreme White, Xtreme Class, 3D Systems, Manufacturing the future, 2015, 1 page.

Chilean Office Action dated Jan. 26, 2022, in counterpart Chilean Patent Application No. 01590-2020 (16 pages, in Spanish).

Chinese Office Action dated Nov. 26, 2021, in counterpart Chinese Patent Application No. 201880080564.7 (8 pages, in Chinese).

Columbian Office Action dated Apr. 13, 2022, in counterpart Columbian Patent Application No. NC2020/0007231 (30 pages, in Spanish with English translation).

(56) References Cited

OTHER PUBLICATIONS

Dilution Table 3Dose Unit Dose Injector, Instructions for Use, www.tsklab.com, retrieved 2019, 1 page.
Gattex (teduglutide) for Injection, Instructions for Use, 2019, 2 pages.
Indian Office Action dated May 18, 2022, in counterpart Indian Patent Application No. 202047023695 (7 pages, in English).
International Search Report and Written Opinion for Application No. PCT/US2018/065192, dated Jun. 4, 2019, 22 pages.
International Search Report and Written Opinion for Application No. PCT/US2020/36200, dated Oct. 26, 2020, 19 pages.
Japanese Notice of Allowance dated Oct. 25, 2021, in counterpart Japanese Patent Application No. 2020-026268 (4 pages, in Japanese with partial English translation).
Krader, Cheryl Guttman. "Pearls for Selecting a Syringe for Intravitreal Injection," Ophthamology Times, Jan. 2021, pp. 1 & 25, 52 pages.
Lucentis Dosage, Generic name: Ranibizumab 10mg in 1mL, Dosage form: injection, solution, Lucentis Dosage Guide—Drugs.com, [retrieved on May 28, 2020]. Retrieved from the Internet: (URL: https://www.drugs.com/dosage/lucentis.html), 7 pages.
Lucentis Ranibizumab Injection, Prefilled Syringe Administration Preparation, Genentech, 2018, 30 pages.
New, Novel Prefillable Microfilter Injection Device for Intraocular Therapeutics, Congruence Medical Solutions Inc, Gautam Shetty, phD, 2018, 19 Pages.
Proven and innovative injection systems delivering your product's potential, Vetter—Packaging systems and technologies for pharmaceutical products, Retrieved from Internet: (https://www.vetter-pharma.com/en/clinical-manufacturing/packaging/systems), retrieved 2019, 7 pages.
Taiwanese Search Report dated Sep. 8, 2021, in counterpart Taiwanese Patent Application No. 109306859 (1 page, in English).
Baudin F., et al., "Association of Acute Endophthalmitis With Intravitreal Injections of Corticosteroids or Anti-Vascular Growth Factor Agents in a Nationwide Study in France," JAMA Ophthalmology, 2018, vol. 136(12), pp. 1352-1358.
Dhoot D.S., "Rates of Suspected Endophthalmitis Following Intravitreal Injections in Clinical Practices in the United States," Ophthalmic Surgery, Lasers Imaging Retina, 2021, vol. 52(6), pp. 312-318.
Pancholy M., "Endophthalmitis Following Intravitreal Anti-Vascular Endothelial Growth Factor Therapy: Changes in Incidence and Outcomes over a 9-Year Period," Current Eye Research, 2021, vol. 46(9), pp. 1370-1377.
Reyes-Capo D.P., et al., "Trends in Endophthalmitis Associated With Intravitreal Injection of Anti-VEGF Agentsat a Tertiary Referral Center," Ophthalmic Surgery, Lasers Imaging Retina, 2021, vol. 52(6), pp. 319-326.
Storey P.P., et al., "The Impact of Prefilled Syringes on Endophthalmitis Following Intravitreal Injection of Ranibizumab," American Journal of Ophthalmology, 2019, vol. 199, pp. 200-208.
U.S. Department of Health and Human Services, Food and Drug Administration, Center for Drug Evaluation and Research (CDER), Center for Biologics Evaluation and Research (CBER), "Guidance for Industry Container Closure Systems for Packaging Human Drugs and Biologics", Chemistry, Manufacturing, and Controls Documentation, May 1999, 56 pages.
Regeneron Pharmaceuticals, Inc.; Instructions, Date of Publication Oct. 2022; www.regeneron.com/downloads/dupixent_ifu-100-spanish.pdf (3 pages).
Bayer AG Jeringa Precargada dated Nov. 26, 2012; https://nomenclator.org/med/eylea-40-mg-ml-solucion (4 pages).
Kocabora M.S., et al., "Intravitreal Silicone Oil Droplets Following Pegaptanib Injection," Acta Ophthalmologica, 88 (2):e44-e45, Mar. 2010.
Kunjukunju N., et al., "Bilateral Avastin Injections," ARVO Annual Meeting Abstract, Investigative Ophthalmology & Visual Science Apr. 2009, vol. 50, 1876, 02 pages.
"Assessing the Impact on Drug Dose Delivery of Passive Safety Devices," Copyright © 2016 Frederick Furness Publishing Ltd., 4 pages.
"Special Feature—Injection Devices: Manufactures Focus in 21st Century Technology While Still Tackling Traditional Challenges" (URL: https://drug-dev.com/special-feature-injection-devices-manufactures-focus-on-21st-century-technology-while-still-tackling-traditional-challenges/); Contract Services, Drug Delivery, Featured Articles, Injection Devices, Sep. 2015, 24 pages.
Japanese Notice of Allowance issued in Japanese Patent Application No. 20239084253 on Feb. 28, 2025 (3 pages; 3 pages English translation).
Regeneron prefilled syringe, posted on market-scope.com, postinh date Dec. 13, 2019, retrieved Apr. 4, 2025, online, URL: https://www.market-scope.com/pages/news/4010/regeneron-s-eylea-injection-prefilled-syringe-now-available(Year: 2019).

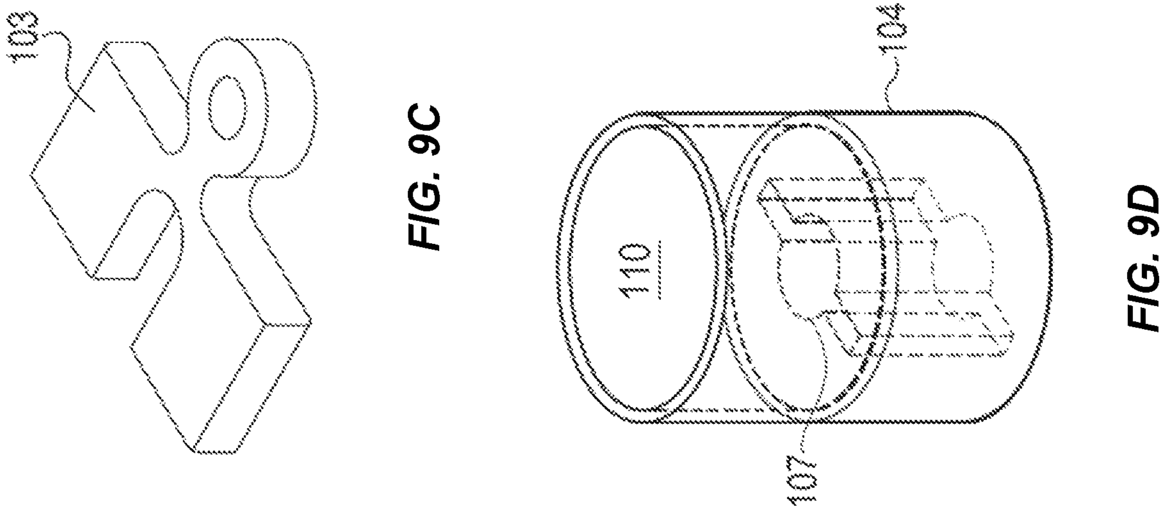
FIG. 9C
FIG. 9D
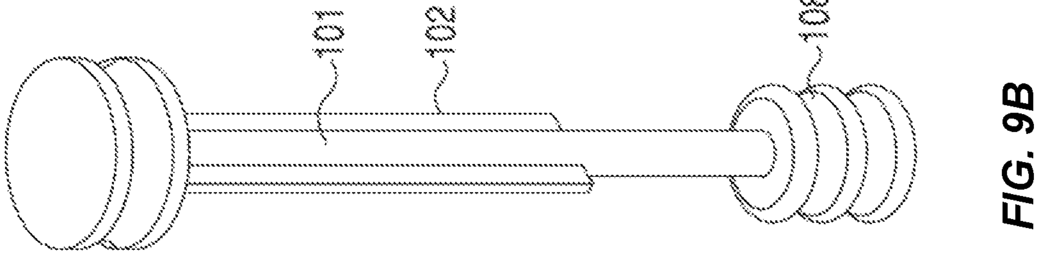
FIG. 9B 500
504
510
508
506
503
512
502
514
516

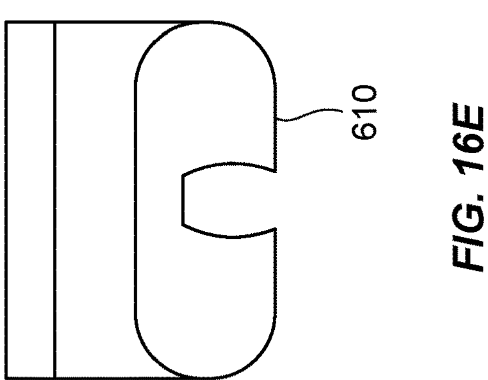
FIG. 16E
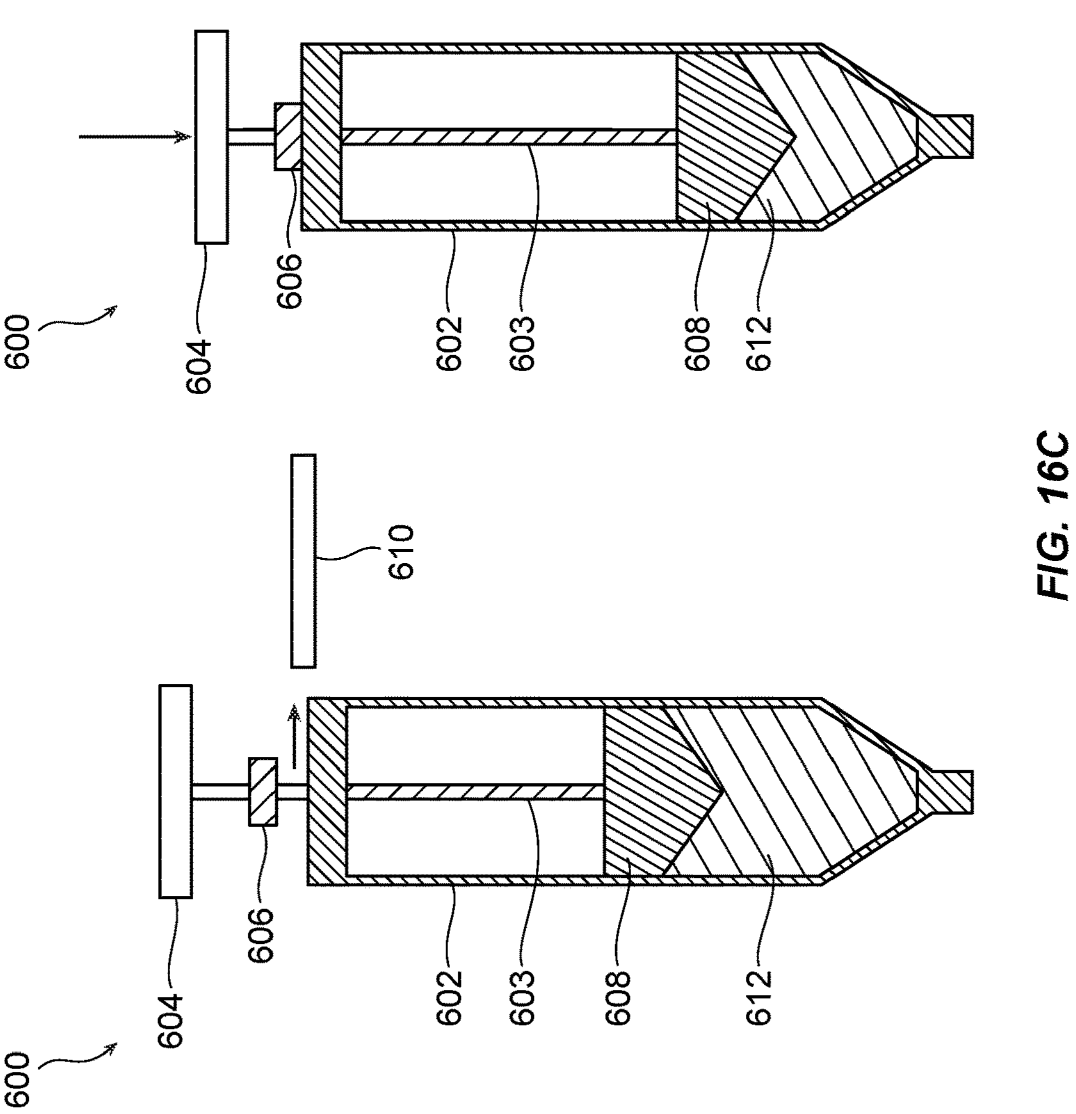
FIG. 16D
FIG. 16C 820
826
822
828
824

800
804
806
801

800
804
802
806
801

822
830
801
828
824
834
832

800
820
802
801
806
832
826
824
830

800
820
801
802
806
832
826
824
830

DEVICES AND METHODS FOR PRECISION DOSE DELIVERY

CROSS-REFERENCE TO RELATED APPLICATIONS

This application is a continuation of U.S. patent application Ser. No. 17/218,875, filed on Mar. 31, 2021, which is a continuation of U.S. patent application Ser. No. 16/900,747, filed on Jun. 12, 2020, which is a continuation application under 35 U.S.C. § 111(a) of International Application No. PCT/US2018/065192, filed Dec. 12, 2018, which claims priority to U.S. Application No. 62/598,212, filed Dec. 13, 2017; U.S. Application No. 62/676,047, filed May 24, 2018; and U.S. Application No. 62/722,252, filed Aug. 24, 2018, all of which are incorporated by reference herein in their entireties. This application is also a continuation of U.S. patent application Ser. No. 17/517,464, filed on Nov. 2, 2021, which is a continuation of U.S. patent application Ser. No. 16/900,747, all of which are incorporated by reference herein in their entireties.

FIELD OF DISCLOSURE

Aspects of the present disclosure relate to devices and methods for priming or otherwise configuring a dose delivery device, e.g., a syringe, to promote precision dose delivery. More specifically, embodiments of the present disclosure relate to devices and methods for loading, storing, transporting, and/or delivering precise doses of a drug product, placebo product, or other product including a fluid.

INTRODUCTION

Liquid drug products may be deliverable to patients in a variety of ways, including via injection. In many cases, the precision and accuracy of a liquid drug product's volume is crucial. For example, medical professionals may have an interest in ensuring that an approved or prescribed volume of a drug product is consistently delivered to each patient requiring the drug. Additionally, over- or under-dosing a patient with a drug product, even slightly, may have an undesired (or even negative) clinical impact on the patient. Moreover, some drug products are prescribed at low volumes (e.g., under 100 μL). At low volumes, human error in preparing and delivering an accurate dose of a drug product for injection may impact the drug's efficacy in a patient and the subsequent clinical effect on the patient.

Additional aspects of liquid drug product delivery can complicate the goal of accurate dose delivery via injection. For example, for a correct dose of a drug product to be dispensed from a device (e.g., a syringe), a corresponding accurate volume of the drug product must be loaded into the device. Furthermore, handling, storage, packaging, and/or transportation of loaded devices must not result in inadvertent expulsion of drug product from the devices. Additionally, prior to administration of a drug product from a device, the device may need to be primed to remove air bubbles from within the device's needle and barrel. Incorrectly priming a device may result in expulsion of too much or too little drug product from the device, which likewise may result in a decreased dose being delivered to a patient, or air bubbles being injected from the device into the patient.

SUMMARY

Disclosed herein are fluid delivery devices. In an aspect of the present disclosure, the devices may include a barrel having a longitudinal axis, a proximal end region, and a distal end region. The proximal end region may include an opening, and the barrel may be configured to receive a drug therein. A plunger rod (having a piston coupled thereto) may be disposed at least partially inside the barrel and protruding from the opening. The plunger rod may include a rack having a plurality of teeth. The device may further include a pinion having a plurality of teeth configured to engage with the plurality of teeth of the rack, and rotation of the pinion against the rack may move at least a part of the plunger rod along the longitudinal axis of the barrel.

Various aspects of the device may include one or more of the features below. The device may also include a shaft affixed to the pinion, wherein rotation of the shaft rotates the pinion against the rack. In one embodiment, a knob may be affixed to the shaft. In another embodiment, a visualization device (e.g., a magnifier) may be disposed on the distal end region of the barrel. In a further embodiment, the device may include a stopper inside the barrel, and the stopper may be affixed to a distal end of the plunger rod. In an exemplary embodiment, the device may further include a circular ratchet disposed coaxially with the pinion, wherein the circular ratchet has a diameter smaller than a diameter of the pinion, a spring-loaded pawl disposed on an internal circumference of the pinion, wherein the pawl is configured to engage the ratchet, and a shaft affixed to the ratchet, wherein rotation of the shaft in one direction causes rotation of the pinion, and rotation of the shaft in a second direction does not cause rotation of the pinion. In some embodiments, the ratchet may be disposed inside the pinion. In some embodiments, the pinion may include a plurality of teeth having a first height, and a stopper tooth having a second height greater than the first height. In further embodiments, the second height of the stopper tooth may prevent the pinion from engaging the plurality of teeth of the rack. In still further embodiments, the second height of the stopper tooth may be configured to contact one of the plunger rod and the rack to stop rotation of the pinion. In still other embodiments, the plunger rod may include an inner column and an outer lumen, and the rack may be disposed on the inner column. In some embodiments, rotation of the pinion against the rack may move the inner column of the plunger rod independently of the outer lumen. In some embodiments, the device may also include a shaft removably affixed to the pinion, wherein the shaft prevents movement of the outer lumen of the plunger rod relative to the barrel, and wherein removal of the shaft allows for movement of the outer lumen of the plunger rod relative to the barrel.

In some embodiments, the plunger rod may further include a body and a flange, the flange extending partially along a longitudinal length of the body and having a width greater than a width of the body, and the barrel may further include a plunger lock, the plunger lock including a through hole configured to allow the flange to pass through the second plunger lock in a specific orientation.

In another aspect of the present disclosure, a drug delivery device may include a barrel having a longitudinal axis, a proximal end region, a distal end region, and an interior, the proximal end region including an opening and the interior including a threaded region. The device may further include a plunger rod disposed at least partially inside the barrel and protruding from the opening, the plunger rod having a threaded region configured to engage the threaded region of the barrel interior. Rotation of the plunger rod about the longitudinal axis of the drug delivery device may move the plunger rod along the longitudinal axis.

Various aspects of the device may include one or more of the features below. The plunger rod may further include a tab protruding from the plunger rod in a first direction and located proximally from the threaded region of the plunger rod, and the threaded region in the interior of the barrel may further include a slot sized and configured to allow for the tab to pass through the threaded region in the interior of the barrel. In some embodiments, the slot may include a first segment parallel to the longitudinal axis of the drug delivery device and a second segment perpendicular to the longitudinal axis of the drug delivery device. In some embodiments the slot may include a third segment parallel to the longitudinal axis of the drug delivery device, wherein the second segment is in between the first segment and the third segment. In other embodiments, the tab is a first tab, and the plunger rod may further include a second tab protruding from the plunger rod in a second direction opposite to the first direction, and the threaded region in the interior of the barrel may further include a second slot sized and configured to allow for the second tab to pass through the threaded region in the interior of the barrel.

In another aspect of the present disclosure, a drug delivery device may include a barrel having a proximal end region, a distal end region, an opening in the proximal end region, an interior, and a threaded region in the interior. The device may further include a sleeve disposed partly inside the barrel and protruding from the opening in the proximal end region of the barrel, the sleeve including a threaded region engaged with the threaded region of the barrel interior. The device may also include a plunger rod disposed at least partially inside the sleeve, and a stopper inside the barrel and located distally from the sleeve, the stopper connected to a distal end of the plunger rod. Rotation of the sleeve in a first direction around a longitudinal axis of the drug delivery device may move the sleeve towards the distal end region of the barrel.

Various aspects of the device may include one or more of the features below. Rotation of the sleeve in the first direction may move the stopper towards the distal end region of the barrel. In some embodiments, the sleeve may include an inner passage, and the stopper may have a diameter larger than a diameter of the inner passage. In some embodiments, the sleeve may include a tab disposed on an exterior of the sleeve, the tab may be located proximally from the threaded region of the barrel interior, and the tab may stop movement of the sleeve towards the distal end region of the barrel. In further embodiments, the tab may be configured to stop movement of the sleeve towards the distal end region of the barrel after the drug delivery device has been primed. In additional embodiments, the tab may be a first tab, the sleeve may further include a second tab disposed on an exterior of the sleeve, the second tab may be located distally from the threaded region of the barrel interior, and the second tab may stop movement of the sleeve towards the proximal end region of the barrel.

In a further aspect of the present disclosure, a drug delivery device may include a barrel having a proximal end region and a distal end region, and the proximal end region may include an opening. The device may also include a plunger rod having a body and a flange, the flange extending partially along a longitudinal length of the body and having a width greater than a width of the body, the plunger rod being disposed at least partially inside the barrel and protruding from the opening. The device may also include a first plunger lock disposed on the barrel, the first plunger lock being configured to block the flange from entering the barrel, and a second plunger lock disposed in the barrel, the second plunger lock including a through hole configured to allow the flange to pass through the second plunger lock in a specific orientation.

Various aspects of the device may include one or more of the features below. In some embodiments, the first plunger lock may be removable. In some embodiments, the first plunger lock may be frangible. In still other embodiments, a distance between the first plunger lock and the second plunger lock may be equivalent to the distance that the stopper must travel to prime the drug delivery device. In other embodiments, the plunger rod may be rotatable around a longitudinal axis of the drug delivery device.

In a further aspect of the present disclosure, a method of dispensing a substance from a drug delivery device having a plunger rod and a barrel may include advancing the plunger rod by a predetermined distance into the barrel until advancement of the plunger rod is resisted by a stop, deactivating the stop, and actuating the plunger rod to deliver the substance.

Various aspects of the device may include one or more of the features below. In some embodiments, advancing the plunger rod may comprise rotating a pinion against a rack disposed on the plunger rod. In some embodiments, the stop may comprise a shaft removably affixed to the pinion, and deactivating the stop may comprise removing the shaft from the pinion. In still other embodiments, deactivating the stop may comprise rotating the plunger rod. In some embodiments, the plunger rod may comprise a flange, and the stop may comprise a lock that prevents the flange from entering the barrel. In other embodiments, deactivating the stop may comprise removing the lock. In some embodiments, deactivating the stop may comprise breaking the lock.

BRIEF DESCRIPTION OF THE DRAWINGS

The accompanying drawings, which are incorporated into and constitute a part of this specification, illustrate various exemplary embodiments and, together with the description, serve to explain principles of the disclosed embodiments. The drawings show different aspects of the present disclosure and, where appropriate, reference numerals illustrating like structures, components, materials, and/or elements in different figures are labeled similarly. It is understood that various combinations of the structures, components, and/or elements in various embodiments, other than those specifically shown, are contemplated and are within the scope of the present disclosure.

There are many embodiments described and illustrated herein. The described devices and methods are neither limited to any single aspect nor embodiment thereof, nor to any combinations and/or permutations of such aspects and/or embodiments. Moreover, each of the aspects of the described inventions, and/or embodiments thereof, may be employed alone or in combination with one or more of the other aspects of the described inventions and/or embodiments thereof. For the sake of brevity, certain permutations and combinations are not discussed and/or illustrated separately herein.

FIGS. 9B-9D depict locking components of the delivery device of FIG. 9A.

FIGS. 16A-16E depict another exemplary delivery device and lock mechanism, according to additional embodiments of the present disclosure.

Figure 1:
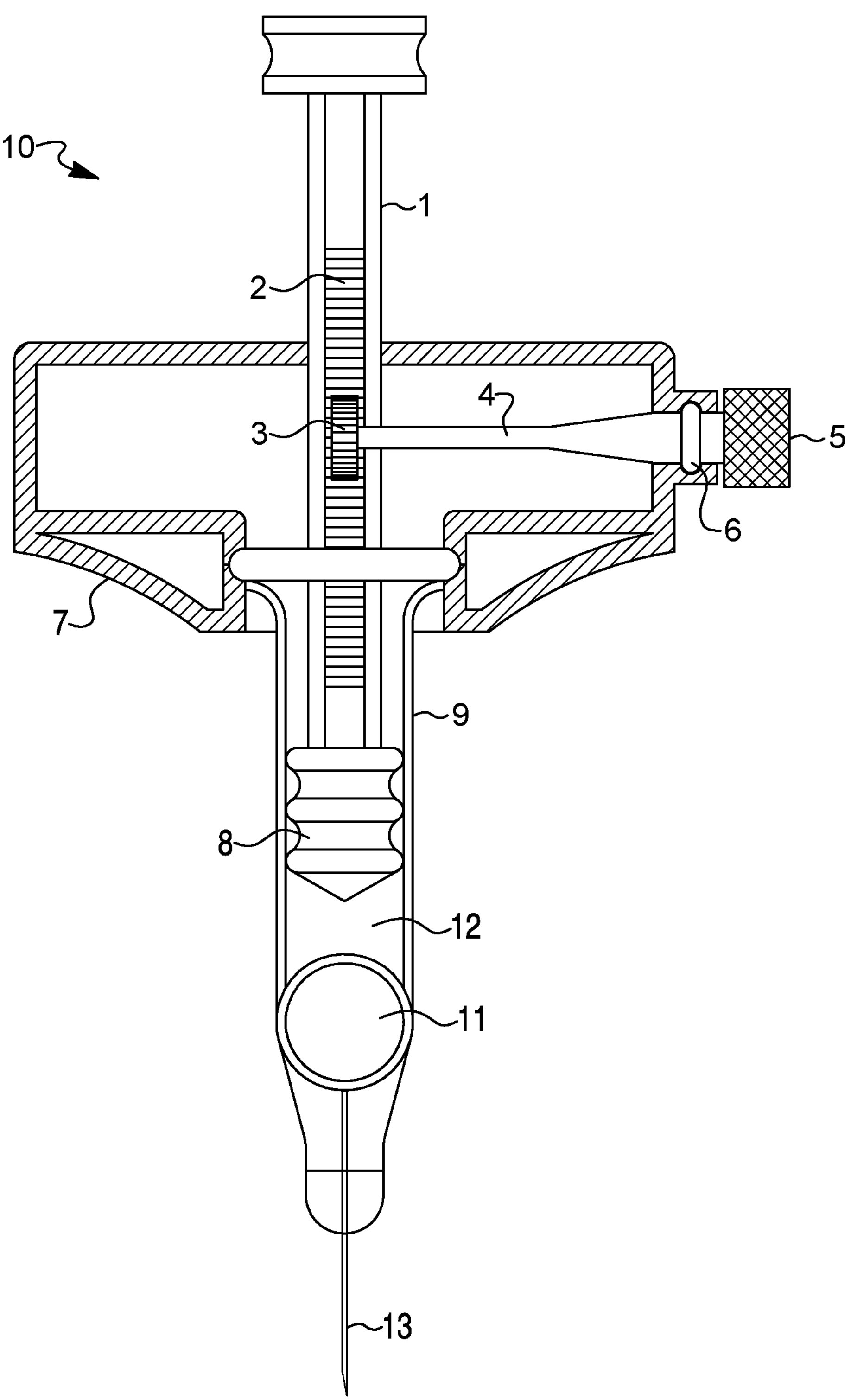
FIG. 1 depicts an exemplary delivery device (e.g., a syringe), according to one embodiment of the present disclosure.

As used herein, the terms "comprises," "comprising," "includes," "including," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." Notably, an embodiment or implementation described herein as an "example" or "exemplary" is not to be construed as preferred or advantageous, for example, over other embodiments or implementations; rather, it is intended reflect or indicate the embodiment(s) is/are one "example," rather than "ideal." In addition, the terms "first," "second," and the like, herein do not denote any order, quantity, or importance, but rather are used to distinguish an element, a structure, a step or a process from another. Moreover, the terms "a" and "an" herein do not denote a limitation of quantity, but rather denote the presence of one or more of the referenced items.

DETAILED DESCRIPTION

Embodiments of the present disclosure may be used in addition to and/or in combination with aspects of U.S. provisional application No. 62/598,212, which in incorporated by reference in its entirety herein.

Embodiments of the present disclosure may be used with any type of fluid-containing products, such as liquid drug products, liquid placebos, or other liquids that may be dispensed in a dose form. In some embodiments, drug products may include one or more active ingredients, including, e.g., small or large molecules or biologics, such as pain medications, steroids, or biologics. As used herein, the term "biologic" may refer to a large molecule (e.g., having a size greater than 15 kDa, greater than 30 kDa, greater than 50 kDa, greater than 75 kDa, or greater than 100 kDa) created in a living system such as a cell. Biologics may include proteins (e.g., antibodies), nucleic acids, large sugars, etc. Unlike small molecules that may have well-defined chemical structures, biologics may have highly complex structures that cannot be easily quantified by laboratory methods. As used herein, the term "drug product" may refer to a volume of a formulated drug substance apportioned into a primary packaging component for packaging, transportation, delivery, and/or administration to a patient.

The term "primary packaging component" refers to a packaging component for a drug product, such as a drug container, that is designed and manufactured to be in direct physical contact with the formulated drug substance. (See, for example, Guidance for Industry on Container Closure Systems for Packaging Human Drugs and Biologics, U.S. Department of Health and Human Services, Food and Drug Administration, Center for Drug Evaluation and Research, and Center for Biologics Evaluation and Research (May 1999), which is incorporated by reference herein.) Examples of primary packaging components include prefillable syringes, Luer syringes, cartridges, and vials made of glass, plastic, and/or other materials.

Embodiments of the present disclosure may be used with products typically having small dose volumes, such as, e.g., ophthalmic drug products. In some embodiments, devices of the present disclosure may be used with drug products including an antigen-binding molecule. In some aspects, the antigen-binding molecule may be an antibody or antigen-binding fragment. In some embodiments, devices of the present disclosure may be suitable for use with drug products including ingredients such as, e.g., aflibercept, alirocumab, abicipar pegol, bevacizumab, brolucizumab, conbercept, dupilumab, evolocumab, tocilizumab, certolizumab, abatacept, rituximab, infliximab, ranibizumab, sarilumab, adalimumab, anakinra, trastuzumab, pegfilgrastim, interferon beta-la, insulin glargine [rDNA origin], epoetin alpha, darbepoetin, filigrastim, golimumab, etanercept, antigen-binding fragments of any of the above, or combinations of such binding domains, such as a bispecific antibody to VEGF or angiopoietin-2, among others.

For some products in particular, e.g., ophthalmic or other drug products, dose accuracy may be particularly important.

However, it is also contemplated that embodiments of the present disclosure may be applicable to any other liquid products or any other context for which precise methods for setting and administering a reliably accurate dose or delivery volume are beneficial.

In some embodiments, devices according to the present disclosure may be manufactured, packaged, filled, and/or otherwise prepared according to processes relevant to the products (e.g., drug products) they may be used with. For example, in some embodiments, devices according to the present disclosure may be sterilized, either before or after being filled and/or packaged. For example, in some embodiments, devices according to the present disclosure may be filled and packaged in, e.g., blister packaging, and/or may be terminally sterilized using any suitable method in the art. For example, devices according to the present disclosure may be terminally sterilized using a chemical sterilization method, such as a method including ethylene oxide or hydrogen peroxide (e.g., vaporized hydrogen peroxide). In some embodiments, devices according to the present disclosure may be terminally sterilized using methods described in, e.g., International Application No. PCT/US2018/021013, filed Mar. 6, 2018, which is incorporated by reference herein in its entirety.

Dose delivery devices available on the market, such as prefilled syringes or syringes for use with vials, may not necessarily assist with accurately loading a desired volume of a product, priming the devices, expelling excessive drug product from the devices, and/or removing air bubbles from the devices. In dose delivery devices containing a small volume of a drug product in particular (e.g., about 500 μL or less, about 300 μL or less, about 250 μL or less, about 200 μL or less, about 150 μL or less, about 100 μL or less, about 50 μL or less, or about 25 μL or less, such as between about 25 μL and about 50 μL, between about 50 μL and about 100 μL, between about 25 μL and about 100 μL, between about 50 μL and about 150 μL, between about 100 μL and about 250 μL, between about 100 μL and about 150 μL, between about 150 μL and about 250 μL, between about 200 μL and about 250 μL, between about 200 μL and about 500 μL, or between about 250 μL and about 500 μL), it may also be difficult to confirm the presence of the correct dose of a drug product in the device with the naked eye. Currently in the dose delivery device market, and specifically in the syringe market, there is a need for mechanisms that allow a user to set precisely for delivery a small volume of a product in a syringe (e.g., a prefilled or fillable/refillable syringe), prime the syringe, remove air bubbles from the syringe, and/or confirm or be assured that the dose volume in the syringe is correct. Embodiments of the present disclosure may assist manufacturers, drug product providers, medical professionals, and/or patients with accurately filling or otherwise preparing a dose administration device, priming the device, removing bubbles from the device, confirming the dose, and/or administering a dose from the device to a patient. Moreover, embodiments of the present disclosure may assist in preventing or mitigating errors or variation in device manufacture or use, such as errors or variation in placement of dose lines on devices, variation in device geometry (e.g., variation in syringe neck geometry), and/or variation or errors in setting a dose line prior to delivery of a product.

In some instances, embodiments of the present disclosure may be of particular assistance to individuals who may have difficulty setting doses with precision and accuracy. For example, embodiments of the present disclosure may assist elderly individuals, young children, or persons with physical or mental disabilities in setting accurate doses.

Described herein are various embodiments for dose delivery devices, and in particular, for syringes. In some instances, embodiments disclosed herein may be used in conjunction with existing syringe body parts to modify off-the-shelf products, which may reduce the development and manufacturing time for the dose delivery devices. In other instances, embodiments disclosed herein may be included in devices during their manufacture. The syringes described herein may be prefilled or may be fillable/refillable.

Embodiments of the present disclosure may include syringes having rotating parts, threaded parts, springs, gears, and the like, that may allow a user to precisely control the movement of dosage setting and delivery elements such as, e.g., plungers and/or stoppers. In some embodiments, for example, screw and gear mechanisms may be used to transfer rotary motion (e.g., on a knob or dial) to linear motion of a plunger, and thus to set the plunger rod of a syringe to a predefined position with reduced human effort and/or relatively greater accuracy. By reducing human effort and/or increasing accuracy, it is contemplated that embodiments of the present disclosure may reduce human error as well.

In some embodiments, visualization devices, such as magnifiers, may be provided with, attached to, or otherwise disposed on, delivery devices, in order to help enhance visibility of dose measurement markers on the devices. It is contemplated that aspects of one embodiment (such as magnifiers, sleeves, guiding pins, channels, screw and gear mechanisms, rotating parts, threaded parts, grips, springs, etc.) may be combined with aspects of one or more other embodiments, to create various combinations and permutations of features in a single device.

In some embodiments, devices according to the present disclosure may be depicted as including one type of plunger rod and plunger, or as including a general schematic representation of a plunger rod and plunger. For example, some devices according to the present disclosure may be depicted or described as including, e.g., a plunger rod having a threaded end, which engages with threads on an interior of a plunger such that the plunger rod and the plunger may be screwed together. It is contemplated that multiple and/or different configurations of plunger rods and plungers may be appropriate for each of the embodiments disclosed herein. For example, in some cases, the aforementioned threaded plunger rod and plunger may be used with embodiments disclosed herein. In some embodiments, a plunger rod may not be affixed to a plunger, and instead may be disposed near, next to, or flush against a plunger such that pressure from the plunger rod towards the plunger may push the plunger, but withdrawal, twisting, or other movement of the plunger rod may not cause the plunger to likewise be withdrawn, twisted, or otherwise moved. As another example, in some embodiments, a plunger rod may be affixed to a plunger by an adhesive, or may be of a single piece with a plunger (e.g., may have been manufactured in a single mold with a plunger).

In some embodiments, devices according to the present disclosure may include various cosmetic features relevant to intended users of the devices. For example, devices according to the present disclosure may be manufactured and sold for use by pediatric patients. In such cases, devices according to the present disclosure may include child-friendly coloring, cartoon images, or other cosmetic features to appeal to children. In some cases, devices according to the present disclosure may include lettering, labeling, or other features designed to be easily recognized by the intended users. For example, lettering on a pediatric device or a device for use by a disabled person or an elderly person may have larger, more accessible labeling so that it may be more easily recognized and read by the user(s) of the device.

FIG. 1 depicts a syringe 10 containing a volume of drug product 12 and having a dose expel control mechanism. The dose expel control mechanism may include a rack 2 and a pinion 3. Rack 2 may be formed on an inner surface of a plunger rod 1 of syringe 10 or may be otherwise attached to an inner surface of plunger rod 1. In some embodiments, rack 2 may, e.g., be engraved, machined, or molded onto plunger rod 1. Rack 2 may include a plurality of teeth extending along its length.

Pinion 3 may also include a plurality of teeth that are configured to engage with the teeth of rack 2. Pinion 3 may be operably connected to an actuator (e.g., a dial or a knob) located external to plunger rod 1 via a pinion rod 4. For example, as shown in FIG. 1, rotation of a dial 5 may cause rotation of pinion rod 4 and thus rotation of pinion 3. Thus, pinion rod 4 may extend from an interior region of syringe 10 (where it connects to pinion 3) to an exterior region of syringe 10 (where it connects to dial 5). In the embodiment of FIG. 1, pinion rod 4 may extend partially or fully through a finger flange 7 (e.g., on, integral to, or affixed to syringe 10). In other embodiments, pinion rod 4 may extend through a body wall of plunger rod 1 and/or syringe barrel 9 of syringe 10. Pinion rod 4 may be supported by a gasket or seal, such as an O-ring 6, where it exits finger flange 7 (or, if appropriate, syringe barrel 9). O-ring 6 may provide physical support to pinion rod 4 and/or pinion 3 while pinion 3 is in motion and/or at rest. While O-ring 6 is described as providing structural support to pinion rod 4 and/or pinion 3, it is also contemplated that O-ring 6 may simply seal the internal region of plunger rod 1 from an external region, or both. Additionally, other seals or gaskets, or combinations thereof, may be used instead of, or in addition to, O-ring 6, and these seals or gaskets may or may not provide structural support and/or sealing. For example, such seals or gaskets may simply provide a barrier protecting the interior region of syringe from an exterior region or may provide structural support and may also act as a barrier.

Teeth of pinion 3 may engage with teeth of rack 2 such that, upon rotation of pinion 3 via dial 5, the rotational motion of pinion 3 may cause translational motion of plunger rod 1. Thus, rotating pinion 3 may cause plunger rod 1 to move distally and/or proximally in syringe barrel 9, which may also move piston 8 (e.g., a stopper) within syringe barrel 9. By rotation of dial 5, piston 8 (which may also act as a stopper) within syringe barrel 9 may be gradually moved towards the needle end of syringe 10, so that air and excess drug may be pushed out through needle 13, priming needle 13 for injection of an appropriate dose of drug product 12.

Pinion 3 and rack 2 may be sized and configured such that rotation of pinion 3 in a given direction or by a given amount (e.g., one clockwise rotation) may cause rack 2 and pinion 3 to disengage from one another, which may cease the ability of dial 5 to advance piston 8. In some embodiments, once dial 5 has been rotated a predetermined amount in a clockwise or counterclockwise direction, rack 2 and/or pinion 3 may cease to move. For example, pinion 3 may be prevented from moving further as a result of reaching a proximal end of rack 2, as a result of disengaging with rack 2, as a result of disengaging with pinion rod 4, as a result of abutting against a stopper, or dial 5 may only be rotatable for a given amount. Accordingly, rotation of dial 5 and pinion 3 a given amount in a given direction may serve to complete priming of the syringe needle.

In some embodiments, when plunger rod 1 has been moved a desired amount (at which point rotation of dial 5 and/or pinion 3 may or may not be stopped), a user may pull dial 5 outwards away from plunger rod 1. Outwards movement of dial 5 may disengage dial 5 from pinion rod 4 and/or may disengage pinion rod 4 from pinion 3. In some embodiments, pinion rod 4 may extend through an opening in a sidewall of plunger rod 1, and pulling dial 5 outwards may retract pinion rod 4 out of the opening so that pinion rod 4 no longer prohibits movement of plunger rod 1. In some embodiments, pulling out dial 5 may lock it in place, thereby preventing further movement of plunger rod 1 via use of dial 5. In some embodiments, pulling dial 5 outwards may unlock the outer plunger rod, allowing it to move freely, whether or not movement of dial 5 is locked. In some embodiments, pulling dial 5 and/or pinion rod 4 outward may disengage pinion 3 from rack 2. In some embodiments, a user may not be able to depress plunger rod 1 until pinion 3 reaches its terminal position and/or until dial 5 is pulled outwards.

Dial 5 may be the only mechanism capable of moving plunger rod 1 until syringe 10 has been primed. For example, the complementary teeth of rack 2 and pinion 3 may prevent a user from depressing plunger rod 1 (and/or pulling plunger rod 1 proximally) until pinion 3 has disengaged from rack 2. This may prohibit drug product 12 from being dispensed until syringe 10 has been primed and may inhibit under- or over-priming of syringe 10 and promote accurate dispensation of drug product 12.

As shown in the embodiment of FIG. 1, syringe 10 may optionally include a magnifier 11 attached to or embedded on syringe barrel 9. Magnifier 11 may aid in reading measurement indicators on syringe barrel 9, may aid in observing the presence or absence of air bubbles in syringe barrel 9, and/or may aid in determining whether a complete dose of drug product 12 has been dispensed from syringe 10. Magnifier 11 may be included in a distal region of syringe 10 and may be any suitable shape or size. For example, magnifier 11 may have a circular or rectangular shape or may wrap around all of or a portion of the circumference of syringe barrel 9. In other embodiments, no magnifier 11 may be included.

The embodiment depicted in FIG. 1 may be operated in the following manner. Dial 5 may be rotated a given amount in a given direction until rotation of pinion 3 stops. A user may detect whether pinion 3 has stopped when dial 5 is unable to rotate further and/or when movement of plunger rod 1 ceases. As discussed above, pinion 3 may stop moving, e.g., as a result of reaching an end region of rack 2, as a result of disengaging with rack 2, as a result of disengaging with pinion rod 4, as a result of abutting against a stopper, or because dial 5 may only be rotatable for a given amount. Alternatively or additionally, in some embodiments, dial 5 may be pulled outwards by a user to prevent further movement of plunger rod 1 via dial 5.

Once movement of plunger rod 1 via dial 5 is complete, a user may optionally confirm the dose level of drug product in syringe barrel 9 and/or may optionally confirm whether any air is trapped within syringe barrel 9. A proximal end of plunger rod 1 may then be pushed to inject a dose of drug product.

Figure 2:
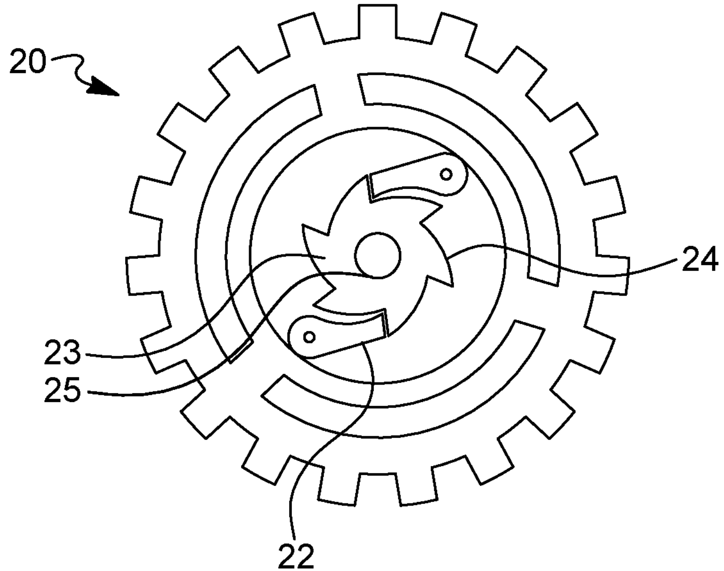
FIG. 2 depicts an exemplary pawl and ratchet mechanism for a delivery device, according to one embodiment of the present disclosure.

FIG. 2 depicts an exemplary variation on the pinion 3 depicted in FIG. 1. Pinion 20 of FIG. 2 may include an internal ratchet and pawl mechanism to allow rotation of pinion 20 in a first direction and to prevent rotation of pinion 20 in a second direction, opposite the first direction. For example, only clockwise rotation may be allowed and counterclockwise rotation may be blocked, or vice versa. In some embodiments, pinion 20 may be prevented from rotating in a direction that would cause plunger rod 1 to move proximally away from the needle end of syringe 10, while rotation in a direction that would cause plunger rod 1 to move distally towards the needle end of syringe 10 is allowed.

As shown in FIG. 2, ratchet 23 may be coaxial with pinion 20, and dial 5 (FIG. 1) may be connected to ratchet 23, for example, via a pinion rod (such as pinion rod 4 depicted in FIG. 1) through a center 25 of ratchet 23. Ratchet 23 may include angled teeth 24. An interior region of pinion 20 may include a spring-loaded pawl 22 operably coupled to the interior region. Pawl 22 may be positioned at an angle complementary to the angles of ratchet teeth 24 and close enough so that a free end of pawl 22 engages ratchet teeth 24. Each ratchet tooth 24 may include a rounded surface, over which the free end of each pawl 22 can slide, and a projecting face against which the free end of each pawl 22 may engage and be stopped. Rotation of dial 5 of FIG. 1 in one direction (e.g., a direction that would cause plunger rod 1 to move away from the needle end of syringe 10) may cause rotation of ratchet 23 such that ratchet teeth 24 do not engage pawls 22, and ratchet 23 may rotate independently of pinion 20. Rotation of dial 5 in the opposite direction, however, may cause ratchet 23 to engage with pawls 22 and to rotate pinion 20 such that plunger rod 1 and piston 8 may move distally towards the needle end of the device, allowing for priming of needle 13 and expulsion of air.

Figure 3A:
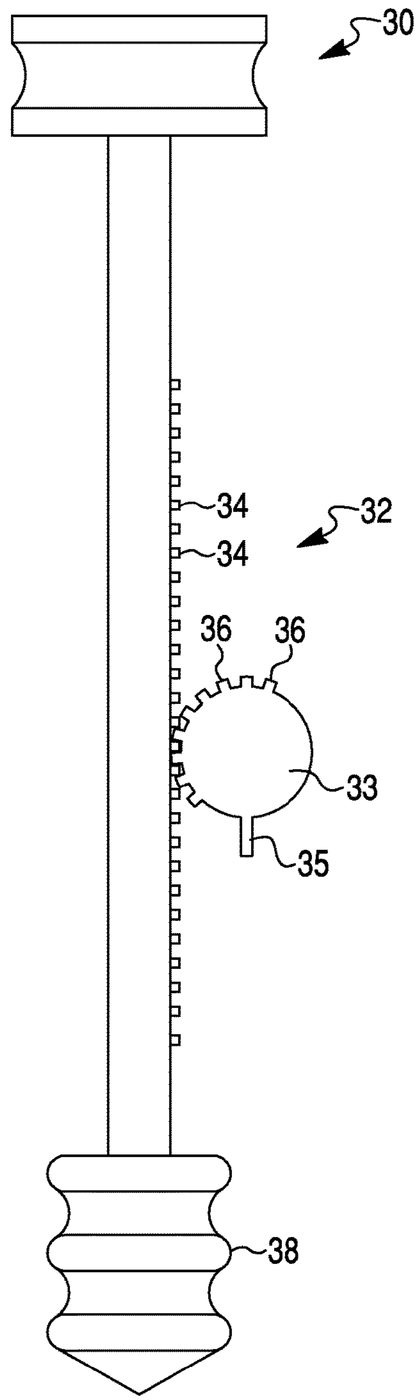
FIGS. 3A and 3B depict an exemplary lock mechanism for a delivery device, according to one embodiment of the present disclosure.
Figure 3B:
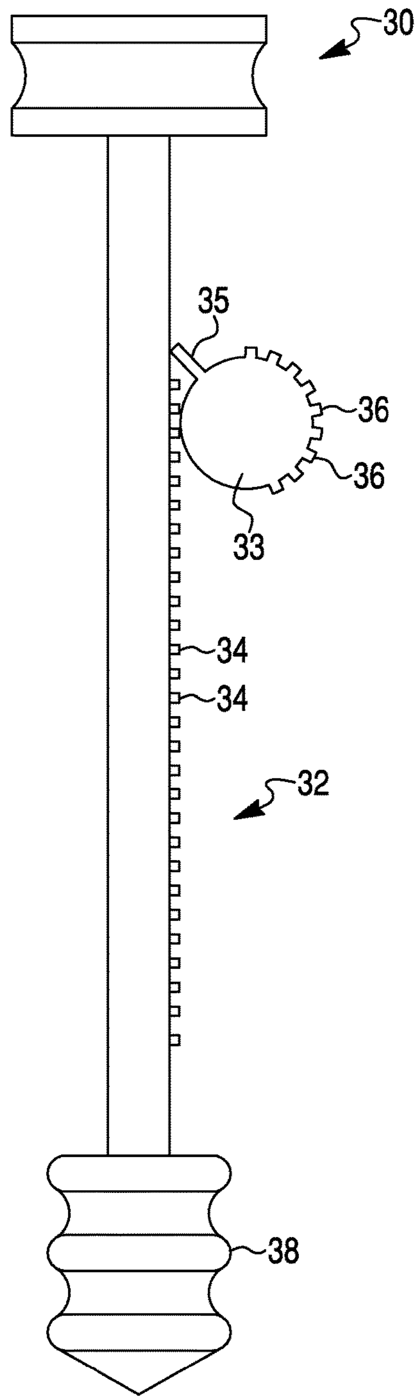

FIGS. 3A and 3B depict another variation of the pinion 3 depicted in FIG. 1. In this embodiment, plunger rod 30 may include a rack 32 extending along at least a portion of its length. Rack 32 may include a plurality of teeth 34 configured to engage with teeth 36 on pinion 33. In addition to teeth 36, pinion 33 may include a stopper tooth in the form of protrusion 35. Protrusion 35 may extend radially further out from pinion 33 than teeth 36 and may have a height that is greater than a height of teeth 36. Pinion 33 may rotate along rack 32 (FIG. 3A) until protrusion 35 on pinion 33 contacts rack 32 or plunger rod 30 (FIG. 3B), halting rotation of pinion 33. In this way, protrusion 35 may prevent more than one rotation of pinion 33. Halting rotation of pinion 33 may consequently halt advancement of plunger rod 30 and piston 38 beyond a predetermined point. The predetermined point may correspond to, e.g., a point at which excess air and dosage of a drug product may be expelled from syringe 10 (see FIG. 1), resulting in accurate priming of syringe 10. In some embodiments, when protrusion 35 contacts plunger rod 30 and pinion 33 assumes the position shown in FIG. 3B, protrusion 35 may be free of rack 32, and plunger rod 30 may slide freely against it. Accordingly, in the embodiment of FIGS. 3A and 3B, instead of the rack length controlling the amount of movement of plunger rod 30 is allotted to prime the syringe, the circumference of pinion 33 may control this movement.

The physical cessation of further pinion movement caused by protrusion 35 on pinion 33 may also provide tactile feedback to a user to indicate that a proper dose has been set and that syringe 10 has been primed. Inclusion of protrusion 35 on pinion 33 may additionally prevent over- or under-rotation of pinion 33 in an undesirable direction (e.g., that would allow movement of plunger rod in a proximal direction). Protrusion 35 may be useful to prevent overfilling of syringe 10 or intake of air into syringe 10 during handling, packaging, storage, and/or transport. In further embodiments, a protrusion 35 may be located on rack 32 instead of, or in addition to, pinion 33 to control movement of pinion 33.

Figure 3C:
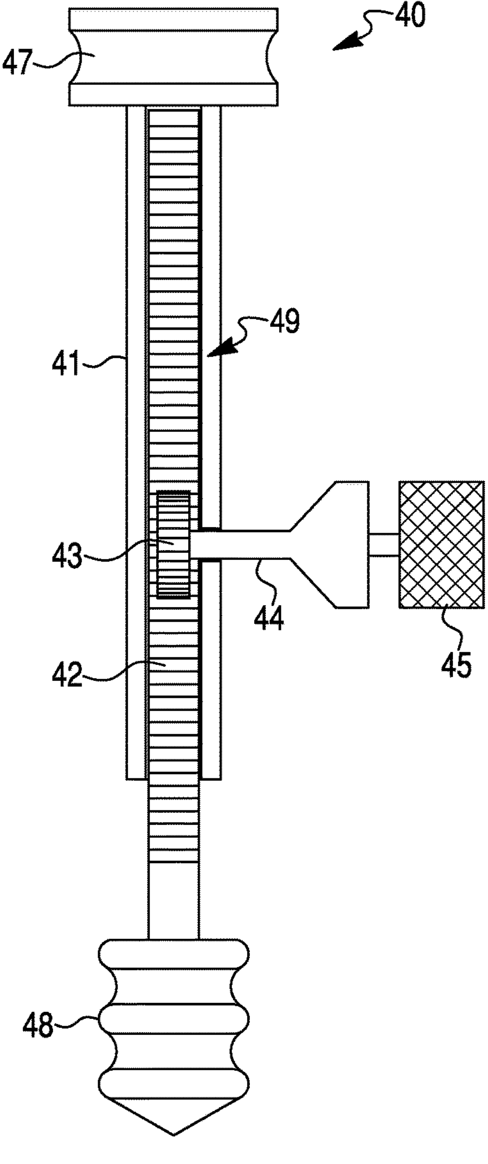
FIGS. 3C and 3D depict an exemplary telescoping mechanism for a delivery device, according to one embodiment of the present disclosure.
Figure 3D:
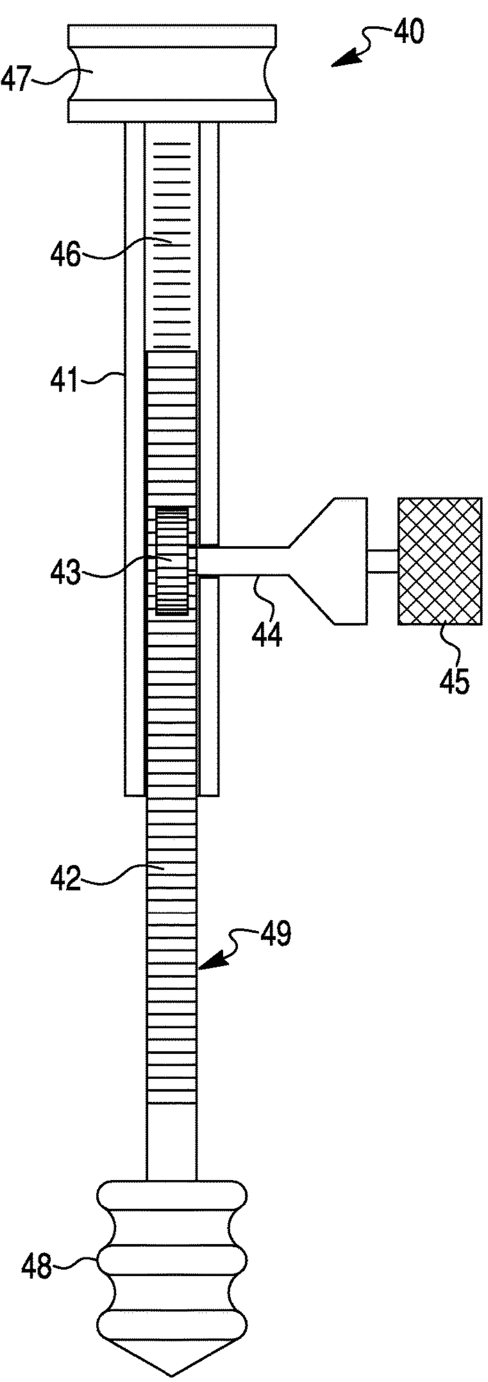

FIGS. 3C and 3D depict another variation of plunger rod 1 depicted in FIG. 1. Plunger rod 40 of FIGS. 3C and 3D may include a locking mechanism configured to prevent accidental depression of piston 48, e.g., when the syringe is being packaged, stored, handled, and/or filled. In some embodiments, plunger rod 40 may include a telescoping inner portion 49 (e.g., an inner tubular portion or a column) having a rack 42. Inner portion 49 of plunger rod 40 may include piston 48 connected to a distal end thereof. Inner portion 49 may move relative to a stationary outer portion 41 (e.g., an outer lumen). Rotation of dial 45 may extend inner portion 49 distally out from outer portion 41 so that inner portion 49 moves independently from outer portion 41.

Dial 45 may be operably connected to the telescoping inner portion 49 by pinion rod 44 (e.g., a shaft) and pinion 43. Rotation of dial 45 may in turn rotate piston rod 44 and pinion 43. Teeth on pinion 43 may engage with teeth on rack 42 of inner portion 49, moving inner portion 49 distally out from outer portion 41. FIG. 3C depicts inner portion 49 of telescoping plunger rod 40 retracted within outer portion 41, and FIG. 3D depicts inner portion 49 of telescoping plunger rod 40 extending out from outer portion 41. Turning dial 45 may thus move piston 48 distally towards the needle end of the syringe to prime the needle and remove air bubbles.

While inner portion 49 of plunger rod 40 may extend from outer portion 41 during priming of the needle, outer portion 41 may not move during dose preparation. In such an exemplary embodiment, dial 45 and/or pinion rod 44 may optionally interfere with outer portion 41 of plunger rod 40 so that plunger rod 40 can't move relative to the syringe barrel and can't be depressed by pressing on thumbpad 47 of plunger rod 40 during dose preparation. For example, to connect pinion 43 to dial 45, pinion rod 44 may extend through an opening of telescoping outer portion 41 of plunger rod 40. Thus, when pinion rod 44 is connected to pinion 43, extension of pinion rod 44 through a sidewall of outer portion 41 may prevent movement of outer portion 41. Because outer portion 41 cannot be moved, plunger rod may not be able to be depressed. Pulling out dial 45 may disengage pinion rod 44 from pinion 43, so that pinion rod 44 no longer extends through outer portion 41. As a result, once dial 45 is pulled out, pinion rod 44 may be removed from engagement with the telescoping portions and may no longer extend through the telescoping portions, allowing plunger rod 40 may to move freely within the syringe barrel. Movement of plunger rod 40 in a distal direction by pressing thumbpad 47 may allow for administration of the dose.

In the embodiment of FIGS. 3C and 3D, when thumbpad 47 is depressed, telescoping inner portion 49 of plunger rod 40 may be fixed in place relative to outer portion 41 so that depressing thumbpad 47 and moving plunger rod 40 does not cause telescoping inner portion 49 to collapse back within outer portion 41. Outer portion 41 and inner portion 49 of plunger rod 40 may, for example, be coupled to each other with positive locking teeth (e.g., teeth 46 of outer portion 41), which may allow inner portion 49 to extend distally from outer portion 41 but may prohibit backwards movement of inner portion 49 into outer portion 41. This may prevent the two telescoping portions from collapsing one into the other when thumbpad 47 is depressed and plunger rod 40 moves distally to expel the dose. This may also prevent proximal movement of inner portion 49 during priming.

In use, dial 45 may be rotated to prime a syringe as depicted in FIGS. 3C and 3D and may allow for finer and/or more controlled movements of plunger rod 40 for such priming. As described above, the inclusion of dial 45 may prevent discharge of any product volume intended for dosage until priming is complete and, e.g., dial 45 has been pulled outwards to unlock movement of plunger rod 40. Although one type of locking mechanism associated with dial 45 is described, it is contemplated that any suitable type of locking mechanism may be incorporated, and that such a locking mechanism may be activated and/or deactivated by pulling, depressing, sliding, or otherwise manipulating dial 45.

Figure 4A:
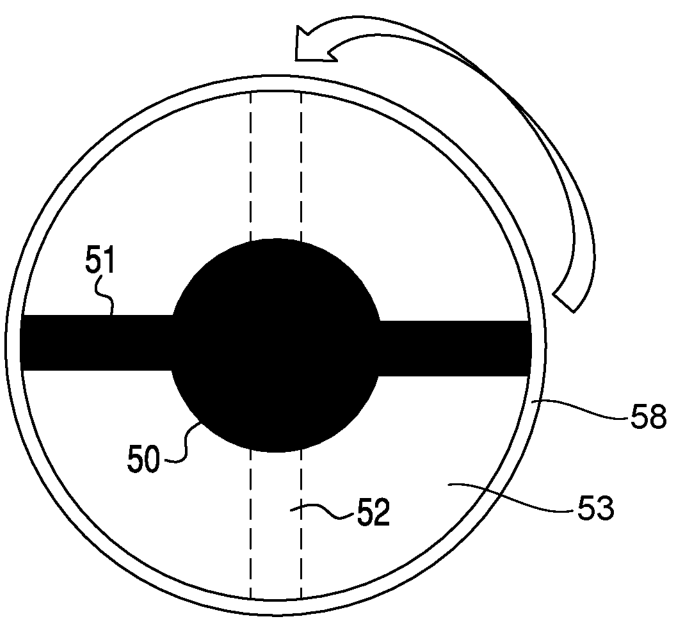
FIGS. 4A and 4B depict exemplary rotational lock mechanisms for a delivery device, according to embodiments of the present disclosure.
Figure 4B:
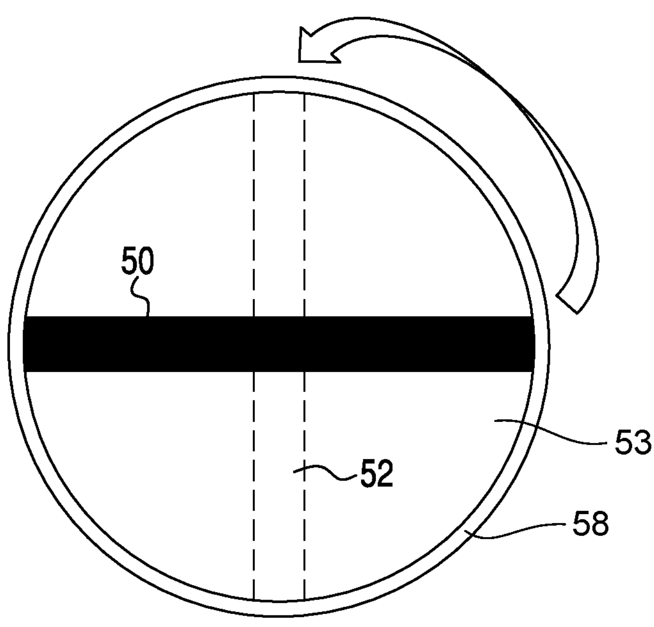

For example, other variations of a locking mechanism are depicted in cross section in FIGS. 4A and 4B. The locking mechanisms of FIGS. 4A and 4B may be used instead of, or in addition to, dial 45 of FIGS. 3C and 3D. In the embodiment of FIG. 4A, the entirety of plunger rod 50 or a proximal region of plunger rod 50 (e.g., a telescoping outer portion of the plunger rod) may include a physical stop (e.g., an interfering bump or projection) to prevent depression of plunger rod 50 during dose preparation and priming—or to allow only enough depression to prepare and prime the dose. In the embodiment of FIG. 4A, an interfering projection 51 (shown in top-down cross-section) may prevent plunger rod 50 from moving distally until plunger rod 50 and/or the portion of plunger rod 50 having projection 51 is rotated relative to other portions of the syringe, e.g., a finger flange (not shown), a stopper 53 located at a mouth of a syringe barrel 58, and/or syringe barrel 58. In the embodiment of FIG. 4B, plunger rod 50 as a whole may have a cross-sectional shape that is not radially symmetrical, such that the shape of plunger rod 50 may prevent it from moving distally until plunger rod 50 is rotated relative to other portions of the syringe, e.g., a finger flange, stopper 53, and/or syringe barrel 58. In order to depress plunger rod 50, plunger rod 50, stopper 53, and/or barrel 58 may be rotated relative to other portions of the syringe in order to be able to depress plunger rod 50 enough to fully dispense the drug dose.

In some embodiments, plunger rod 50 may not be capable of moving past, e.g., a finger flange or stopper 53 in the syringe barrel until plunger rod 50 is rotated a certain number of degrees (e.g., 90 degrees) in relation to the finger flange or the stopper. In some embodiments, the finger flange or stopper 53 may be rotated (e.g., 90 degrees) in relation to plunger rod 50. For example, plunger rod 50 may have a particular cross-sectional shape (e.g., a generally rectangular shape and/or projections 51), and syringe barrel 58 and/or stopper 53 may include a blocking component and/or may be sized and shaped so that projections 51 of plunger rod 50 cannot fit through until the relevant parts have been rotated sufficiently so that the complementary shapes align and plunger rod 50 can pass through.

In some embodiments, an opening 52 in stopper 53 and/or syringe barrel 58 (and/or a finger flange, not shown), and a cross-section of plunger rod 50 may have complementary shapes but may be offset from each other unless one or the other is rotated until the shapes align. In FIGS. 4A and 4B, projections 51, or the general shape of plunger rod 50, do not align with opening 52 until the finger flange or plunger rod 50 is rotated sufficiently. While two projections 51 from plunger rod 50 and a corresponding shape of opening 52 are depicted in FIG. 4A, and while a given cross-sectional shape of plunger rod 50 is depicted in FIG. 4B, it is contemplated that any suitable number, size, and shaped openings and projections and/or cross-sectional shapes may be used. Additionally, while the exemplary embodiments show the required rotation as being 90 degrees, it is contemplated that any suitable amount of rotation (less than or greater than) 90 degrees may be needed.

Figure 4E:
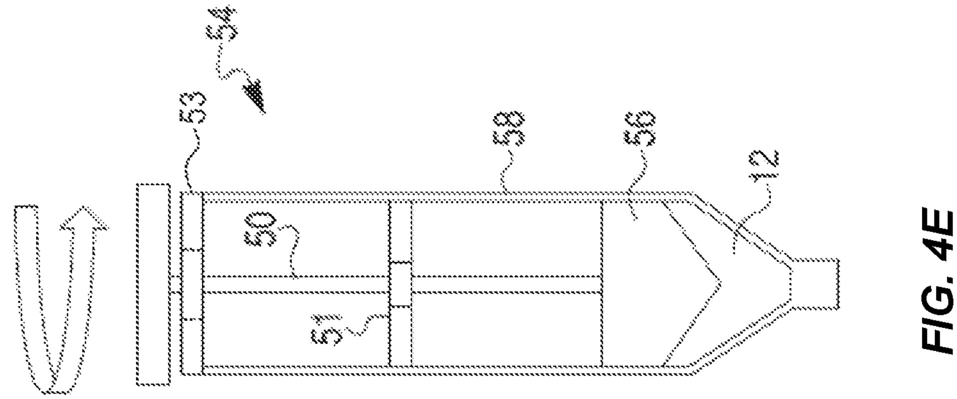
FIGS. 4C-4E depict an exemplary delivery device with an exemplary rotational lock mechanism in various positions, according to an embodiment of the present disclosure.
Figure 4D:
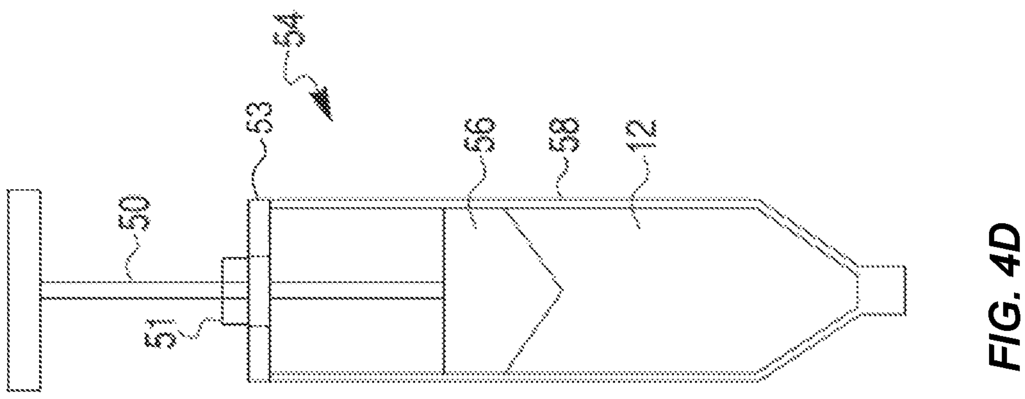
Figure 4C:
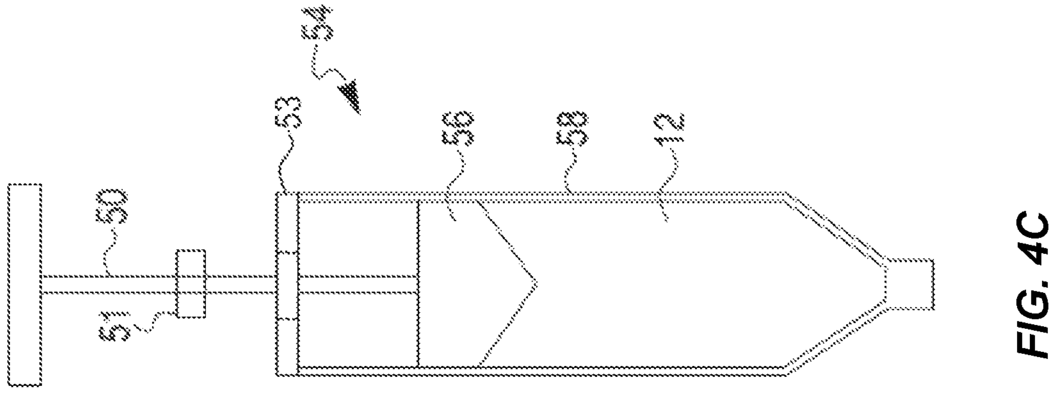

FIGS. 4C-4E depict a side view of a syringe 54 having plunger rod 50, with projections 51, in three different positions. Syringe 54 may include stopper 53, through which projections 51 cannot fit until projections 51 and stopper 53 have been rotated relative to one another such that the shape of projections 51 fits a complementary opening in stopper 53 (see, e.g., dotted lines in FIG. 4A). Plunger rod 50 may be coupled to a plunger 56, which may be configured to fit snugly within a barrel 58 of syringe 54. Syringe 54 may include a volume of a drug product 12 suitable for dispensing from syringe 54. In FIG. 4C, syringe 54 is depicted in a first, un-actuated position. Projections 51 are positioned about plunger rod 50 in a first orientation. In FIG. 4D, syringe 54 is depicted in a second, partially actuated position. Projections 51 in the first orientation are blocked from passing through stopper 53, and thus the further depression of plunger rod 50 is also blocked. In FIG. 4E, syringe 54 is depicted in a fully actuated position. Upon rotation of plunger rod 50 (e.g., in the manner indicated by the curved arrow, or alternately in the opposite direction), projections 51 may be moved into a second orientation about plunger rod 50. In the second orientation, projections 51 may pass through stopper 53, allowing for further depression of plunger rod 50 and plunger 56.

In some embodiments, projections 51 may be positioned on plunger rod 50 such that they do not protrude from the general profile of syringe 54. For example, projections 51 may be located inside, e.g., barrel 58 before syringe 54 is actuated (e.g., in FIG. 4C). In such embodiments, projections 51 may be located, e.g., inside a portion of stopper 53 before syringe 54 is actuated. In some such embodiments, stopper 53 may have a greater thickness so as to accommodate projections 51, and may have a proximal cavity sized and configured to house projections 51 in a first orientation, and a more distal cavity configured to accommodate projections 51 in a second orientation, such that rotation of plunger rod 50 and/or projections 51 may allow for movement of plunger rod 50 in a distal direction.

In some embodiments, a second set of projections may be incorporated in plunger rod 50 either proximally or distally from projections 51. The second set of projections may have similar geometry to projections 51, but may be radially offset from projections 51, such that additional rotation of plunger rod 50 is required for the second set of projections to pass through an opening in, e.g., stopper 53 (e.g., opening 52). Alternately, a second set of projections may have a geometry that cannot fit through an opening, such that plunger rod 50 is inhibited from moving in a given direction by their geometry. Such a second set of projections may be useful in, e.g., limiting movement of plunger rod 50 either before or after projections 51 have passed through the opening. In some embodiments, limiting of movement in this manner may be used in controlling an amount of movement of plunger rod 50 allowed for priming syringe 10, prior to further rotation of plunger rod 50 to allow for dispensing a dosage amount from syringe 10. In further embodiments, limiting of movement in this manner may be used to control a dosage volume that may be dispensed from syringe 50. See, for example, FIGS. 15A-E described further below. As is the case with all embodiments depicted and described herein, this embodiment may be combined with aspects of other embodiments described herein.

In some embodiments, the syringe may be configured to provide feedback to the user to indicate when rotation of plunger rod 50 and projections 51 and/or the finger flange is complete and plunger rod 50 is aligned with openings 52 (see FIGS. 4A-4B). For example, a "clicking" noise or other audio or tactile feedback mechanism may be incorporated into the syringe.

Figure 5:
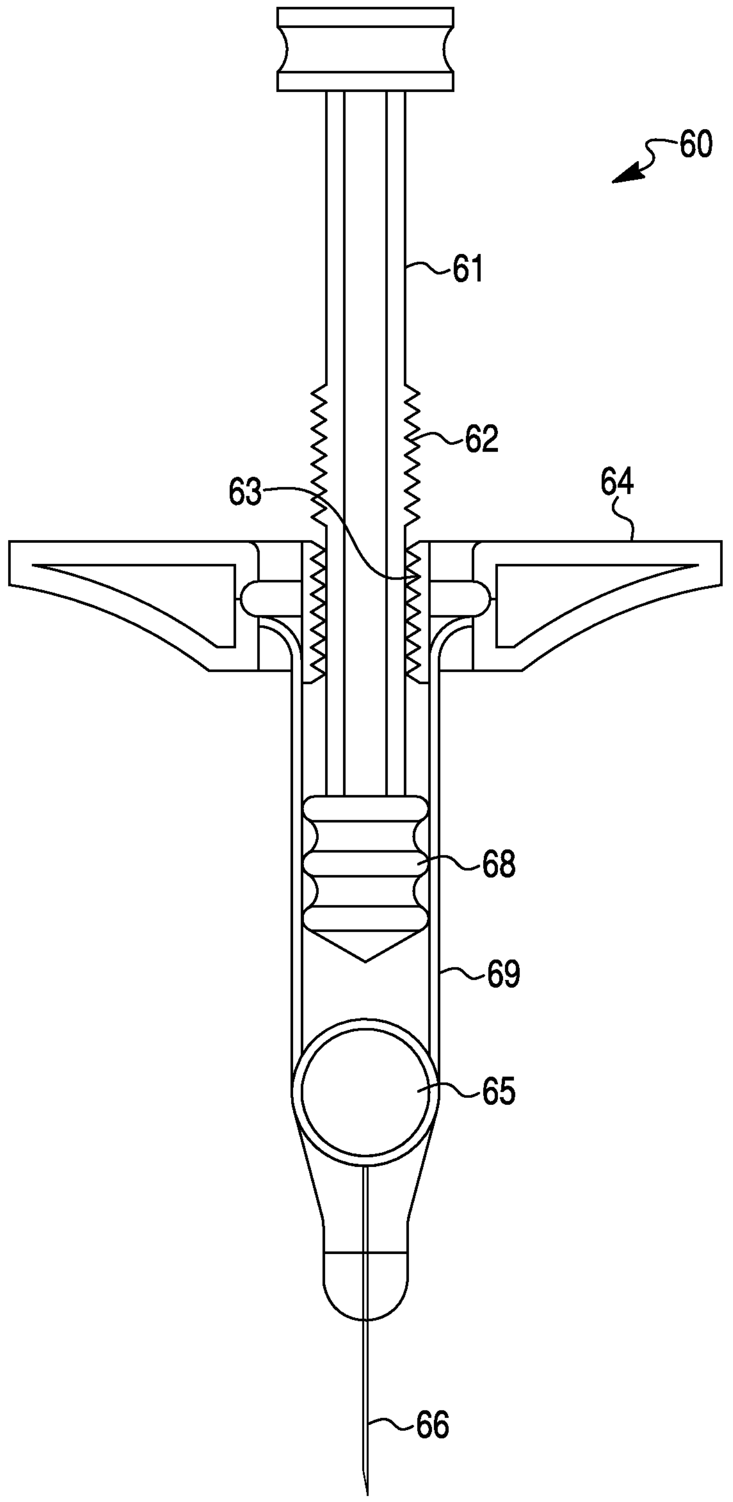
FIG. 5 depicts an exemplary delivery device, according to one embodiment of the present disclosure.
Figure 6B:
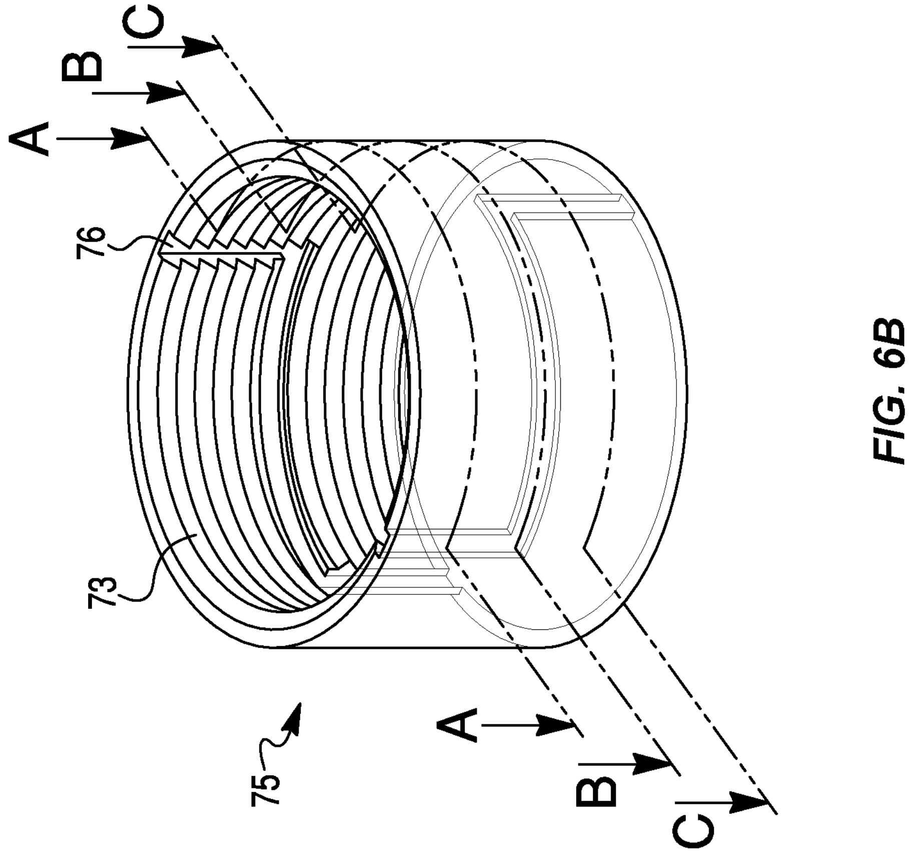
FIGS. 6A-6E depict an exemplary delivery device and locking mechanism, according to one embodiment of the present disclosure.
Figure 6A:
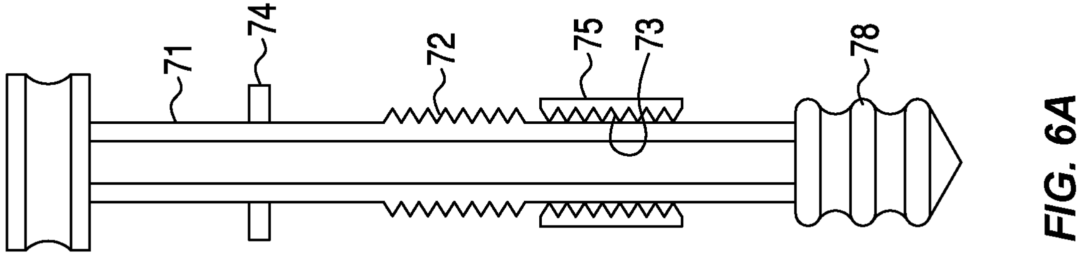
Figures 6C, 6D, 6E:
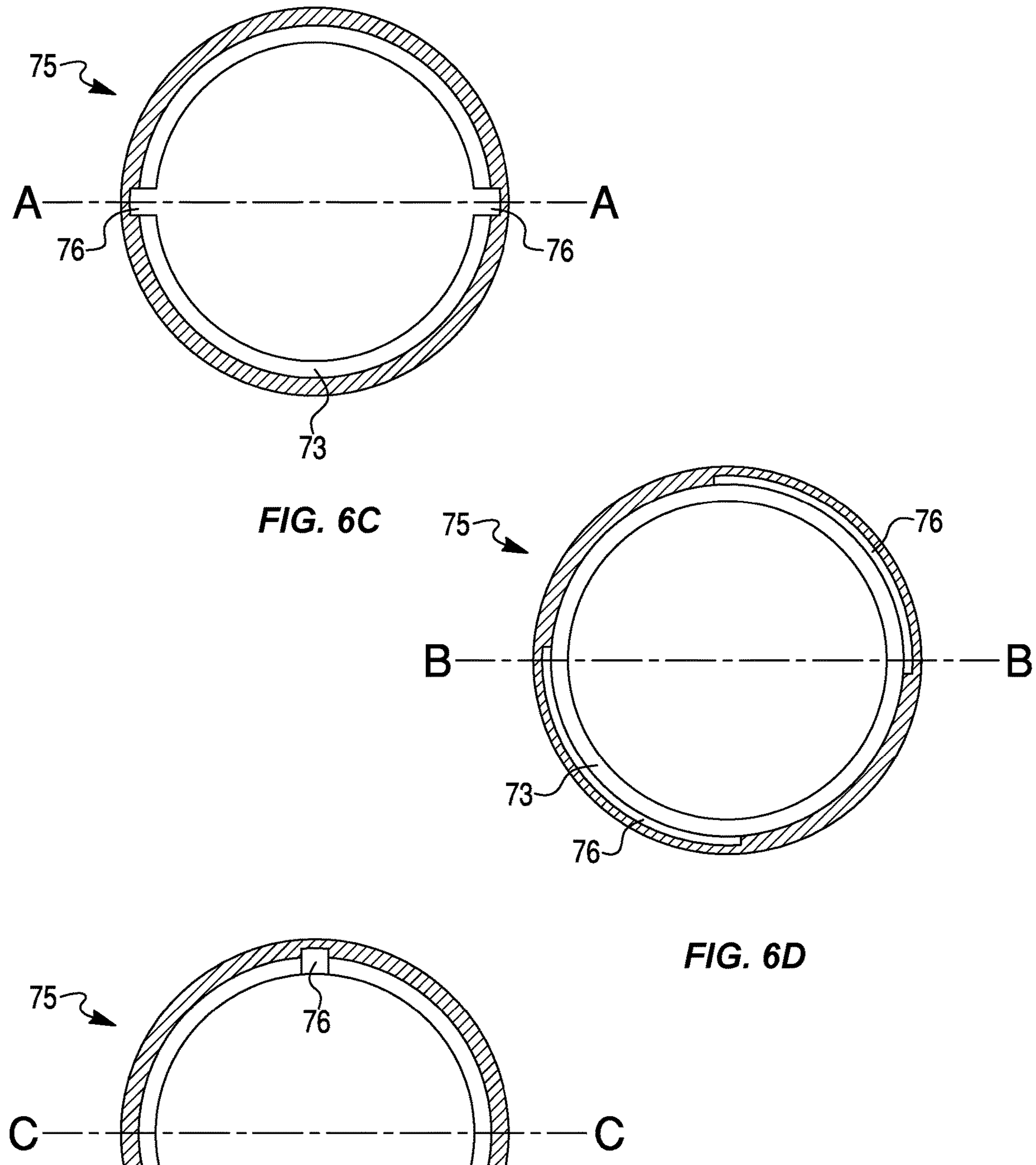

Referring now to FIG. 5, another exemplary syringe 60 is pictured having a dose expel control mechanism. In the embodiment of FIG. 5, the dose expel control mechanism includes two sets of angled helical threads. A first set of helical threads 62 is included on an exterior surface of plunger rod 61. Threads 62 may extend around the entire circumference of plunger rod 61 or around a portion of the circumference. A second set of helical threads 63, complementary to external helical threads 62 of plunger rod 61, are included on an internal circumference of syringe barrel 69 and/or finger flange 64 through which plunger rod 61 passes. Threads 62 may extend around the entire circumference of syringe barrel 69 and/or finger flange 64 or around a portion of the circumference. Threads 62, 63 may be engraved, molded, machined, attached, or otherwise included to the surfaces of plunger rod 61 and syringe barrel 69 or finger flange 64, respectively.

Plunger rod 61 may be rotated to move threads 62 of plunger rod 61 through threads 63, converting the twisting motion of plunger rod 61 into translational (or linear) motion of plunger rod 61 (and thus, piston 68) in syringe barrel 69. The linear motion of piston 68 may push air bubbles and excess drug out through syringe needle 66. Thus, needle 66 may be primed and readied for injection by twisting of plunger rod 61. Both threads 62, 63 may be sized and configured such that, once threads 62 are moved entirely through threads 63, air is removed from within syringe barrel 69, and a predetermined volume of drug product is expelled from syringe needle 66 to prime needle 66.

Threads 62, 63 may also prevent plunger rod 61 from being depressed before priming of needle 66 occurs. For example, in order to depress plunger rod 61 to dispense the drug product, plunger rod 61 must first be twisted—i.e., needle 66 must first be primed. Once threads 62 are rotated through threads 63 and priming is complete, a user may be able to depress plunger rod 61 to deliver the dosage.

As discussed above in relation to FIG. 1, the embodiment of FIG. 5 may also optionally include a magnifier 65. Magnifier 65 may aid in reading magnified volume measurements of the drug product in syringe barrel 69, may aid in observing the presence or absence of air bubbles in syringe barrel 69, and/or may aid in determining whether a complete dose of drug product has been dispensed from syringe 60. Magnifier 65 may be included in a distal region of syringe 60 and may be any suitable shape or size. For example, magnifier 65 may have a circular or rectangular shape or may wrap around all of or a portion of the circumference of syringe barrel 69. In other embodiments, no magnifier 65 may be included.

To operate syringe 60, a user may first rotate plunger rod 61. Plunger rod 61 may need to be rotated a partial rotation, one complete rotation, or more than one complete rotation in order to pass threads 62 through threads 63 and disengage threads 62 from threads 63. At this time, a user may optionally confirm the dose level in syringe barrel 69. The user may use magnifier 65 to perform this step, if magnifier 65 is included. The user may then push plunger rod 61 to dispense the dose of drug product.

In some embodiments, syringe 60 may provide feedback to the user to indicate when rotation of plunger rod 61 is complete and the dose is ready for injection. For example, a "clicking" noise or other audio or tactile feedback mechanism may be incorporated into syringe 60.

The embodiment of FIGS. 6A-6E may operate in a similar manner to the embodiment of FIG. 5, but may further include a locking mechanism to prevent accidental depression of plunger rod 71 when priming of the needle is complete. For example, like FIG. 5, the embodiment of FIGS. 6A-6E includes threads 72 on plunger rod 71, which must be twisted through corresponding threads 73 of syringe barrel 75. However, plunger rod 71 may also include a stop 74 located on an outer surface of plunger rod 71, proximal to threads 72.

Stop 74 may be sized and shaped to fit within a slot 76 extending through threads 73. For example, stop 74 may enter a vertical portion of slot 76 passing through some of internal threads 73 of syringe barrel 75 (depicted in, e.g., section A-A in FIGS. 6B and 6C). Slot 76 may also include a horizontal section (e.g., along section B-B depicted in FIGS. 6B and 6D). Once stop 74 slides fully into the vertical section of slot 76, the user must rotate plunger rod 71 in the direction opposite the direction of threads 72 of plunger rod 71 in order to slide stop 74 through the horizontal portion of slot 76 and to advance plunger rod 71 further distally. Because of the need for an opposing direction of rotation, the risk of accidental advancement of plunger rod 71 may be reduced. Finally, the plunger may be depressed downwards to move stop 74 through a second vertical section of slot 76 (e.g., section C-C depicted in FIGS. 6B and 6E), to expel a volume of the drug product.

Slot 76 may be shaped to require clockwise or counterclockwise rotation, depending on the relative locations of the horizontal and vertical sections. Additionally, although slot 76 is shown and described as including one horizontal portion requiring rotation of rod 71, it is contemplated that multiple horizontal portions may be included, requiring rod 71 to be rotated addition times in the same direction or in multiple directions. Further, although stop 74 is depicted as including two projections on plunger rod 71, it is contemplated that one projection or more than two projections may be included as part of stop 74, and slot 76 may be shaped and sized to accommodate the different configurations of stop 74.

Although threads 73 are described as being on an internal surface of syringe barrel 75, it is contemplated that threads 73 and slot 76 may be located on an internal surface of a finger flange instead of, or in addition to, syringe barrel 75. Moreover, as is the case with all embodiments depicted and described herein, the above-described embodiment may be combined with aspects of other embodiments described herein. For example, rod 71 may include additional projections and/or geometries, such as those shown in FIGS. 4A-4E and FIGS. 15A-15E, to provide a hard stop to the movement of rod 71.

Figure 7A:
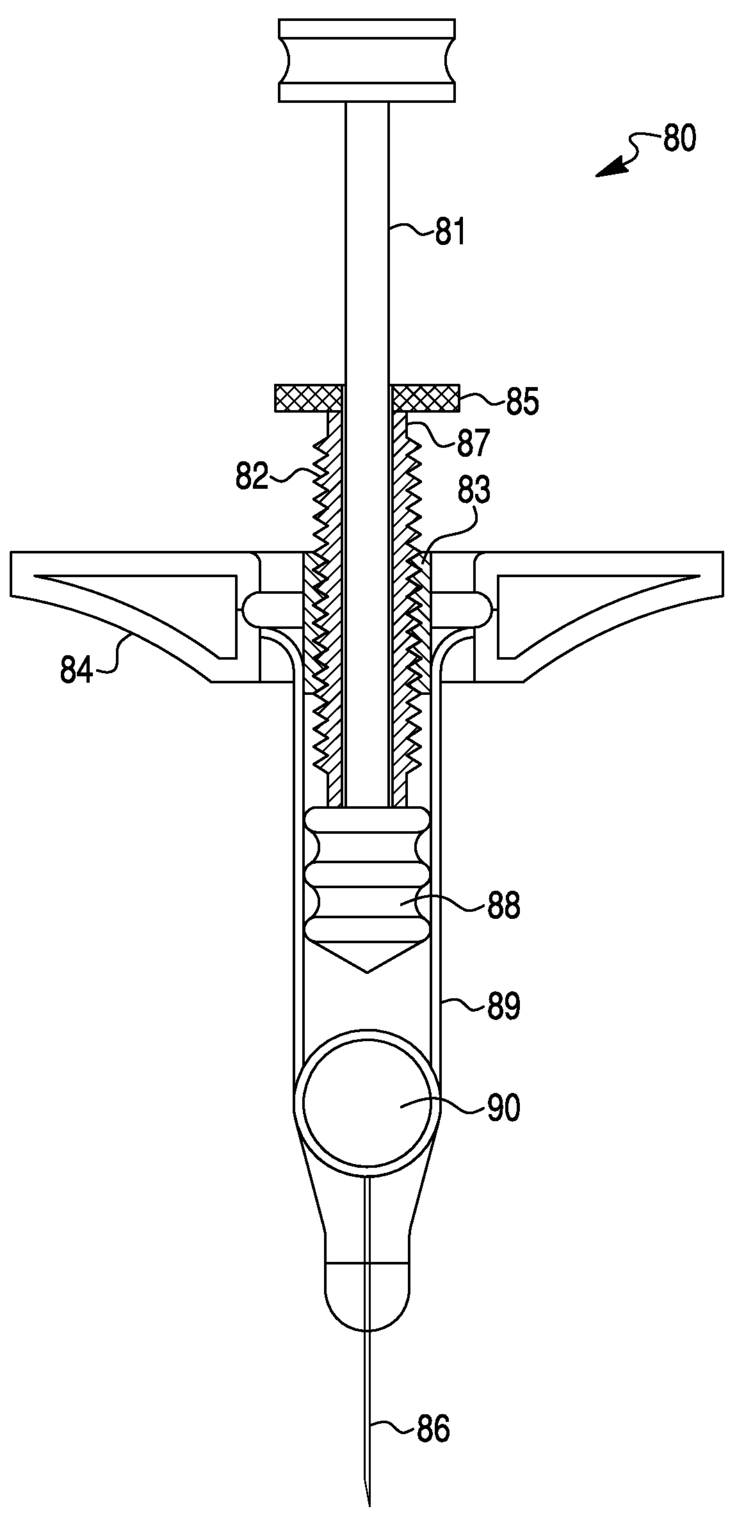
FIG. 7A depicts an exemplary delivery device, according to one embodiment of the present disclosure.
Figure 7B:
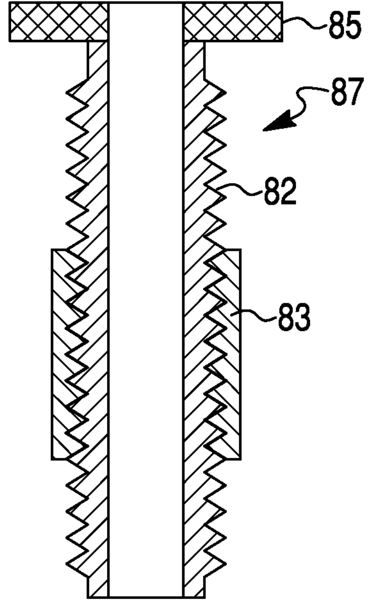
FIG. 7B depicts a threaded portion of the delivery device of FIG. 7A.

Referring now to FIGS. 7A and 7B, another embodiment of a dose expel control mechanism is depicted. In FIG. 7A, syringe 80 includes complementary helical threads 82 and 83. External threads 82 in this embodiment are located on a sleeve 87 surrounding plunger rod 81 instead of directly on plunger rod 81. A close-up of the threaded portions of syringe 80 is depicted in FIG. 7B. Sleeve 87 may allow for free distal movement of plunger rod 81 (towards the needle end of syringe 80), but may block undesirable proximal movement of piston 88. Before depression of plunger rod 81, rotation of sleeve 87 (e.g., via twisting of dial rod 85 located at a proximal end of sleeve 87) may be transformed into a controlled sliding movement of sleeve 87 into syringe barrel 89 via threads 82 on sleeve 87 and corresponding threads on finger flange 84 and/or syringe barrel 89. The controlled sliding movement of sleeve 87 may gradually push plunger rod 81 and stopper 88 towards the distal needle end of the device. Movement of plunger rod 81 through the threaded region may allow for controlled expulsion of air and priming of needle 86.

As in previous embodiments, the embodiment of FIG. 7A may also optionally include a magnifier 90. Magnifier 90 may magnify volume measurements of the drug product in syringe barrel 89, may aid in observing the presence or absence of air bubbles in syringe barrel 89, and/or may aid in determining whether a complete dose of drug product has been dispensed from syringe 80. Magnifier 90 may be included in a distal region of syringe 80 and may be any suitable shape or size. For example, magnifier 90 may have a circular or rectangular shape or may wrap around all of or a portion of the circumference of syringe barrel 89. In other embodiments, no magnifier 90 may be included.

To operate syringe 80, dial rod 85 may be rotated a partial rotation, one complete rotation, or more than one complete rotation in order to pass threads 82 of sleeve 87 through threads 83 until threads 82 are disengaged from threads 63. At this time, a user may optionally confirm the dose level in syringe barrel 89. The user may use magnifier 90 to perform this step, if magnifier 90 is included. The user may then push plunger rod 81 to dispense the dose of drug product.

In some embodiments, syringe 80 may provide feedback to the user to indicate when rotation of plunger rod 81 is complete and the dose is ready for injection. For example, a "clicking" noise or other audio or tactile feedback mechanism may be incorporated into syringe 80. In some embodiments, a user may know that priming is complete because dial rod 85 may not rotate any further, plunger rod 81 may not move any further when twisting, and/or dial rod 85 may abut a portion of finger flange 84 and/or syringe barrel 89, preventing further distal movement of dial rod 85.

In some embodiments, a locking mechanism like the one discussed above in reference to FIGS. 6A-6E may be incorporated into plunger rod 81. By requiring that plunger rod 81 be turned (e.g., 90 degrees, although turning plunger rod 81 more or less is than 90 degrees is also contemplated) prior to administration to allow plunger rod 81 to move freely, plunger rod 81 may be prevented from being pressed in a distal direction during needle priming.

Figure 8:
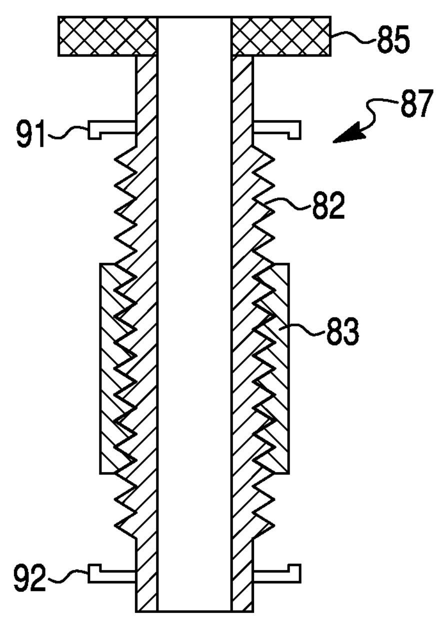
FIG. 8 depicts an alternative embodiment of the threaded portion of FIG. 7B.

In further embodiments, a locking or stopping mechanism may be incorporated into sleeve 87 of FIGS. 7A and 7B. Such a mechanism is depicted in FIG. 8. By incorporating stops 91 and/or 92 (e.g., tabs or projections) onto sleeve 87 (e.g., at positions above and/or below threads 82 on sleeve 87 and threads 83 in the syringe barrel), over-rotation of the sleeve in either direction (and thus over-priming or unwanted removal of sleeve 87) may be prevented. Stop 91 may be located proximal of threads 82 and may be configured to stop movement of sleeve 87 towards the distal end region of the syringe barrel. Stop 92 may be located distally from threads 82 and may be configured to stop movement of sleeve 87 towards the proximal end region of the syringe barrel.

Referring now to FIGS. 9A-9D, another syringe 100 is pictured with a further embodiment of a dose expel control mechanism. This embodiment may include, for example, a key 103 to act as a removable stop at a junction between syringe barrel 109 and plunger rod 101. Key 103 may obstruct movement of plunger rod 101 when it is in place between syringe barrel 109 and a proximal region of plunger rod 101. Key 103 may be placed between plunger rod 101 and syringe barrel 109, e.g., during packaging, filling, or preparation of syringe 100. Key 103 may snap-fit, friction-fit, twist-fit, or otherwise be set in place in any suitable manner. A user may then remove key 103 just prior to use of syringe 101. To remove key 103, a user may pull a tab included on key 103, may snap off a tab, may break a frangible portion, may twist key 103, or may remove key 103 in any suitable manner. Syringe 100 is depicted as having a magnifier 105 disposed at a distal end portion of syringe barrel 109, which may assist in, e.g., visualizing a level of product in barrel 109.

It is contemplated that the key and/or locking mechanisms described above may be useful in the context of fillable syringes as well as pre-filled syringes, which may undergo sterilization, packaging, storage, and/or shipment after being filled. In pre-filled syringes, key 103 may prevent the accidental depression of plunger rod 101 prior to its intended use, thus preserving the sterility, safety, and dose volume of the drug product. Variations of key 103 may include, for example, a frangible stop that may be broken by applying a certain amount of force to plunger rod 101.

Figure 9A:
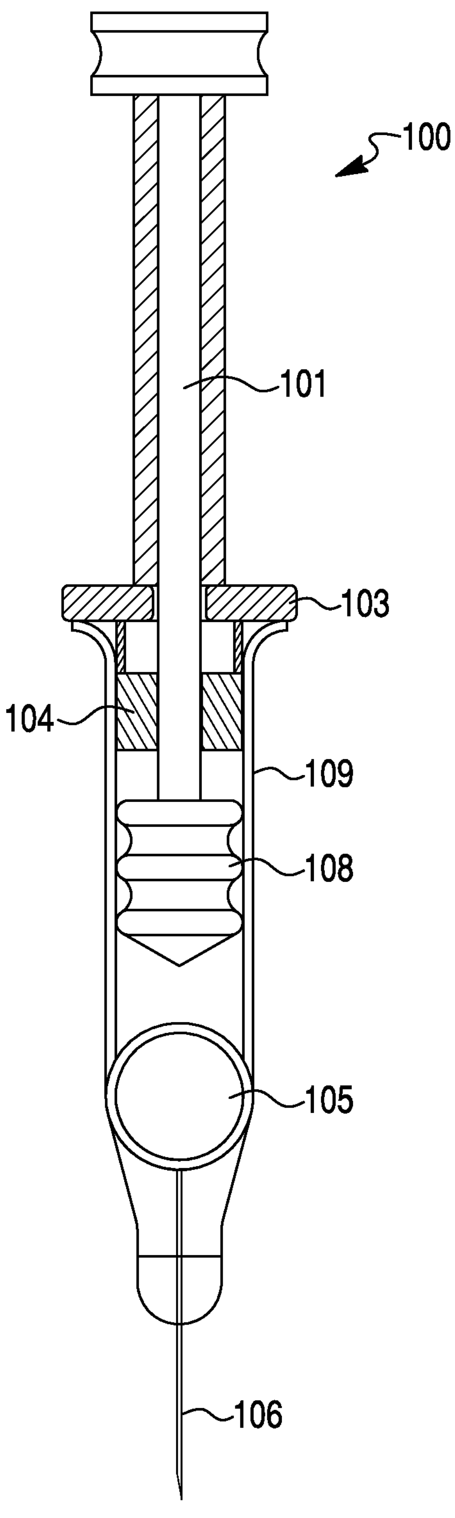
FIG. 9A depicts an exemplary delivery device, according to one embodiment of the present disclosure.

In addition to key 103, the embodiment depicted in FIG. 9A may include a locking mechanism similar to that discussed with respect to, e.g., FIGS. 4A-4E, above, or FIGS. 15A-E, described further herein. For example, as is shown in FIG. 9D, a slot 107 may be included in a stopper 104 of syringe 100. Stopper 104 may have an open portion 110 through which plunger rod 101 may move without being rotated to a set position. The open portion 110 may allow the plunger to move a distance suitable for priming needle 106. Slot 107 may be sized and shaped to fit the cross-sectional area of plunger rod 101 in a particular orientation. For example, plunger rod 101 may include a flange 102 sized and shaped to pass through slot 107 when aligned with slot 107. Stopper 104 may be disposed at a proximal region of syringe barrel 109, such that plunger rod 101 must be rotated to a set position to align flange 102 with slot 107 prior to being depressed through at least part of stopper 104. Although flange 102 and corresponding slot 107 are depicted, slot 107 and plunger rod 101 may have any suitable complementary cross-sectional shapes. Moreover, plunger rod 101 may have multiple cross-sectional geometries along its length, to either provide a hard stop to distal movement of plunger rod 101 or require additional turning of plunger rod 101 relative to stopper 104 to further move plunger rod 101 (see, e.g., FIGS. 15A-15E). As is the case with all embodiments depicted and described herein, this embodiment may be combined with aspects of other embodiments described herein.

Once key 103 is removed, plunger rod 101 may be allowed to move distally from its original position down through open portion 110 of stopper 104. This distal movement of plunger rod 101 may move piston 108 just enough to prime needle 106 and to remove any air bubbles. Stopper 104 may halt additional distal movement of plunger rod 101 when flange 102 hits the inner portion of stopper 104, where slot 107 begins. At that time, plunger rod 101 may need to be rotated to align flange 102 with slot 107 in stopper 104 before rod 101 can be pushed distally through the rest of stopper 104 to move piston 108 and discharge the drug dose.

In some embodiments, syringe 100 may be configured to provide feedback to the user to indicate when plunger rod 101 and flange 102 are aligned with slot 107 and/or when priming of syringe 100 is complete. For example, a "clicking" noise or other audio or tactile feedback mechanism may be incorporated into syringe 100.

Figure 10A:
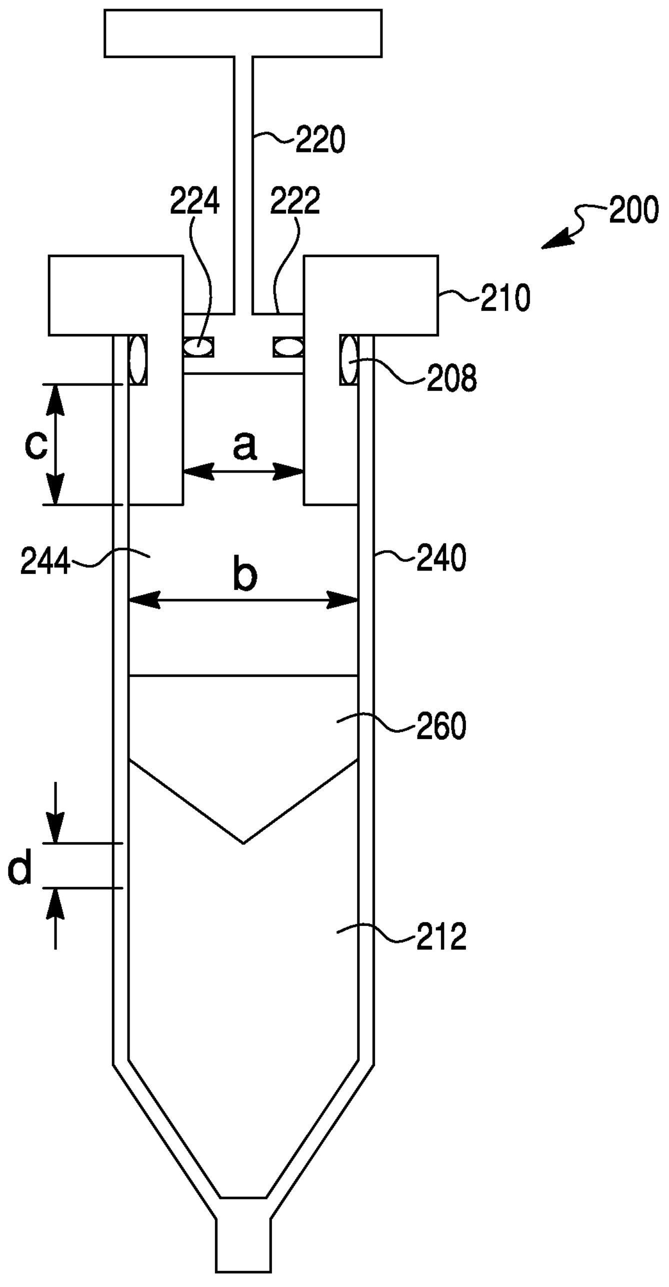
FIGS. 10A-10C depict further exemplary delivery devices according to additional embodiments of the present disclosure.
Figure 10B:
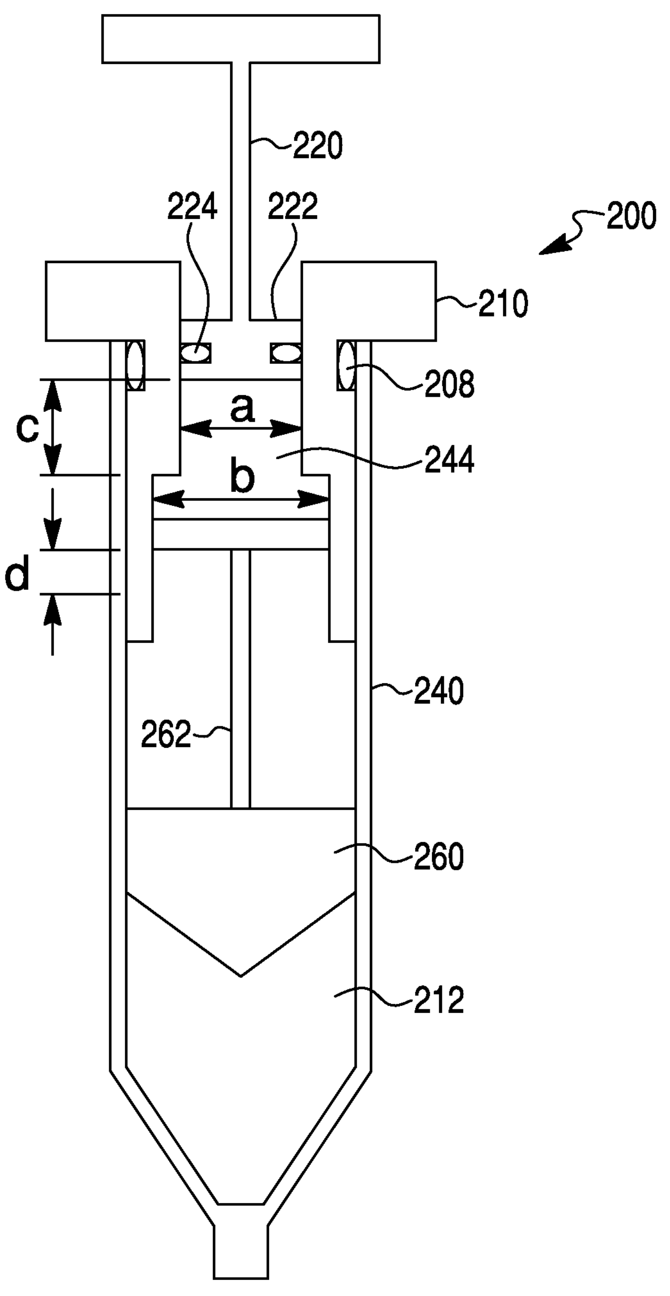
Figure 10C:
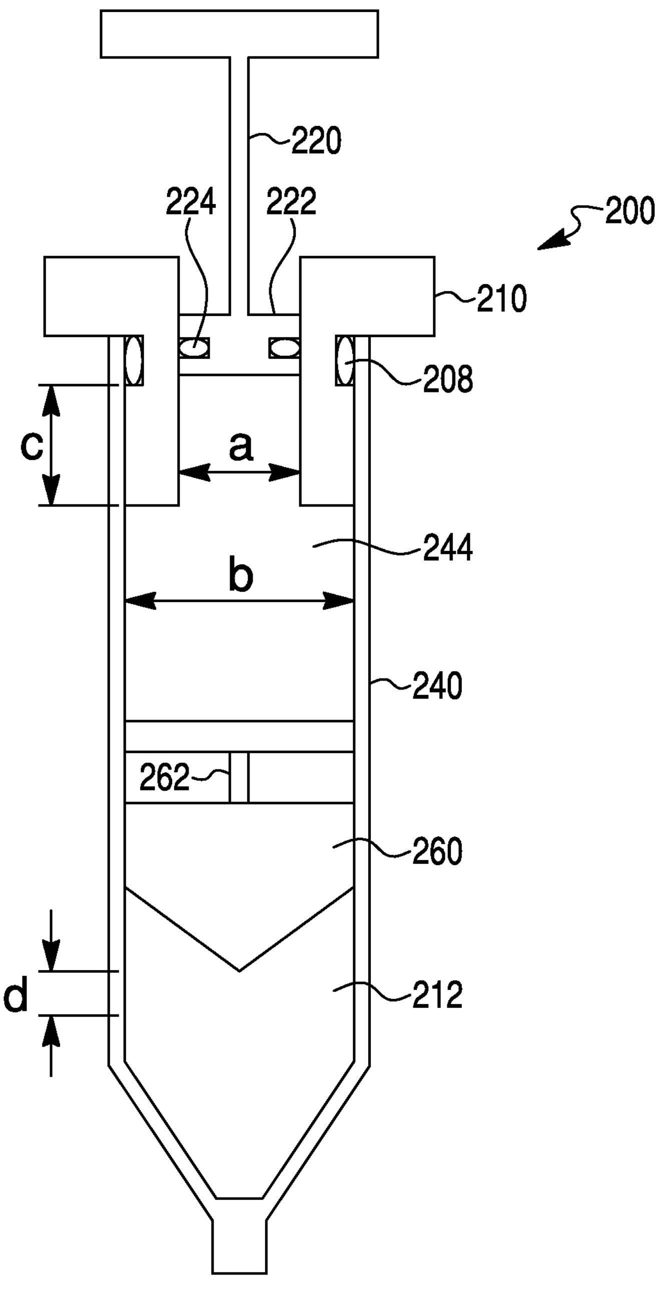

Referring now to FIGS. 10A-10C, a cross-sectional image of a syringe 200 is depicted, with various embodiments of a further dose expel control mechanism. Syringe 200 may include a barrel 240 and a plunger rod 220. Plunger rod 220 may be coupled to a first plunger 222, which may be configured to fit into an opening in a flange 210 positioned at a proximal plunger rod end of barrel 240. Flange 210 may be configured to fit securely within barrel 240, and may be, e.g., sealed against an interior of barrel 240 with an O-ring 208. The interior of barrel 240 may include a second plunger 260 configured to fit snugly within the interior of barrel 240. A first fluid 244 may be disposed inside barrel 240 to a proximal side of plunger 260, and a second fluid, e.g., a drug product 212, may be disposed inside barrel 240 to a distal side of plunger 260. A needle, cannula, tube, or other attachment may be coupled to a distal end of barrel 240, through which a fluid, e.g., drug product 212, may be expelled or withdrawn.

The opening of flange 210 may have a cross-sectional width a into which plunger 222 may be configured to securely fit. In some embodiments, plunger 222 may be configured to form a seal against flange 210, e.g., with the use of an O-ring 224. The portion of flange 210 having width a may also have a depth c. As shown in FIG. 10A, in some embodiments depth c may correspond to a distance between a distal side of plunger 222 and a distal side of flange 210. Distal movement of plunger 222 for, e.g., a distance corresponding to depth c (e.g., caused by depression of plunger rod 220 towards flange 210) may cause a first volume of fluid 244 in the opening of flange 210 to be displaced distally by a distance corresponding to depth c. Displacement of the first volume of fluid 244 may in turn push plunger 260, causing a second volume of drug product 212 to be expelled from syringe 200. Barrel 240 may have a cross-sectional width b located distally from flange 210, where width b is greater than width a. Due to the differences between widths a and b (and thus the differences in fluid volume capacity in the portions of syringe 200 having widths a and b), distal movement of plunger 222 by, e.g., a distance corresponding to depth c may cause plunger 260 to move distally by a smaller distance d. In this manner, a movement of, e.g., plunger rod 220 in the distal (or proximal) direction may be converted into a proportionally smaller, and thus more controllable, movement of plunger 260 and thus a more controllable expulsion (or withdrawal) of a volume of drug product 212.

The embodiments depicted in FIGS. 10B and 10C may differ somewhat from the embodiment of FIG. 10A. Referring to FIG. 10B, cross-sectional widths a and b may both be widths of an opening in flange 210. In such embodiments, a second plunger rod 262 may be disposed within the barrel, such that a portion of plunger rod 262 is disposed within, and extends across an interior of, the portion of flange 210 having width b. Plunger rod 262 may be coupled to, and may extend proximally from, plunger 260. Moreover, plunger rod 262 may have a proximal side that extends across the area of the opening in flange 210 having width b, such that distal movement of fluid 244 may cause distal movement of plunger rod 262, which in turn may push plunger 260 distally. Referring to FIG. 10C, cross-sectional width b may refer to the internal cross-sectional width of barrel 240, as with the embodiment depicted in FIG. 10A, and second plunger rod 262 may be disposed within, and may extend across an interior of, barrel 240. Similarly to the embodiment depicted in FIG. 10B, plunger rod 262 may have a proximal side that extends across the internal area of barrel 240 having width b, such that distal movement of fluid 244 may cause distal movement of plunger rod 262, which in turn may push plunger 260 distally. As with the embodiment of syringe 200 depicted in FIG. 10A, a movement of, e.g., plunger rod 220 in the distal direction may be converted into a proportionally smaller, and thus more controllable, movement of plunger 260 and thus a more controllable expulsion of a volume of drug product 212.

With respect to the embodiments depicted in FIGS. 10B and 10C, plunger rod 262 may form a seal with adjacent parts of syringe 200, such that fluid 244 may not travel distally through/past plunger rod 262. This may result in the need for less fluid 244, and may allow for a region of "empty" space between fluid 244 and drug product 212, which may aid in preventing leakage or mixture of fluid 244 with drug product 212. The "empty" spacy may include a vacuum, or may include, e.g., dry or sterile air. In some embodiments, the "empty" space may include additional fluid 244 (or another fluid) to provide additional structural support to the syringe. In any of the embodiments depicted in FIGS. 10A-10C, fluid 244 may be any suitable liquid or gaseous fluid, such as, e.g., water for injection, dry gas, sterile air, or the like.

Figure 11A:
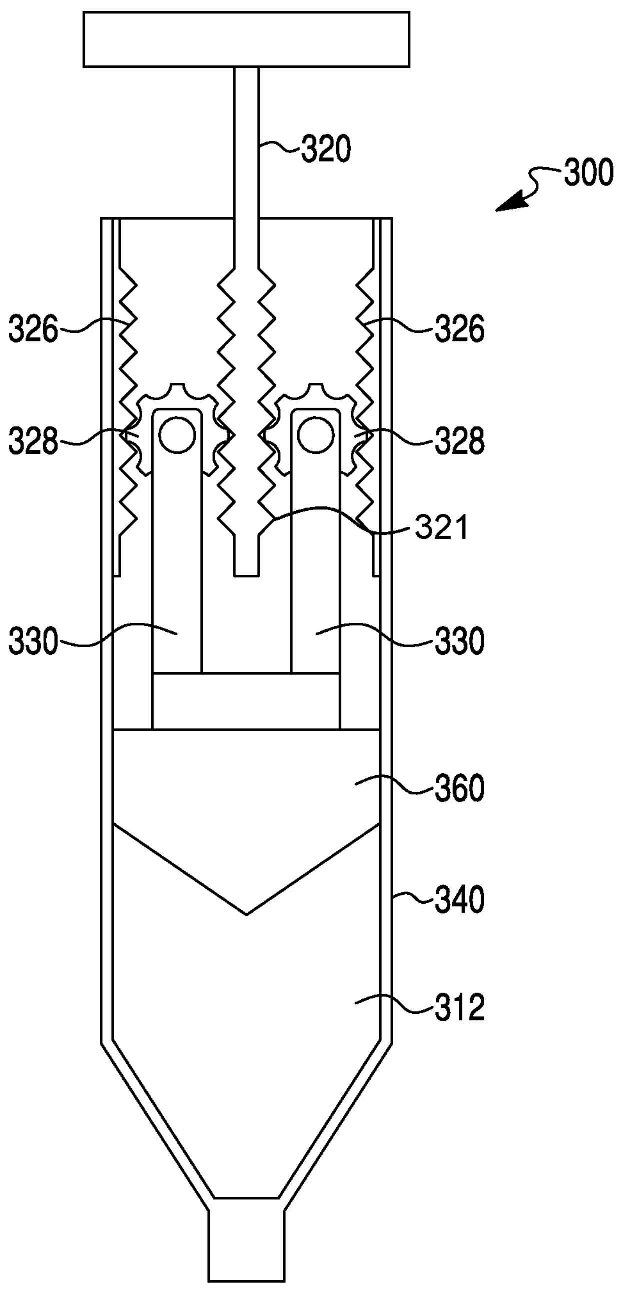
FIGS. 11A and 11B depict still further exemplary delivery devices according to additional embodiments of the present disclosure.

Referring now to FIG. 11A, a cross-section of another syringe 300 is depicted with a further embodiment of a dose expel control mechanism. Syringe 300 may include a barrel 340, a plunger 360, and a drug product 312. A plunger rod 320 may extend into barrel 340, and may include several ratchet-type teeth 321 that may engage with pinions 328, which in turn may engage with ratchet type teeth 326 on an interior of barrel 340. Each of pinions 328 may be coupled to one of rods 330, which may be coupled to plunger 360. A needle, cannula, tube, or other attachment (not pictured) may be coupled to a distal end of barrel 340, through which a fluid (e.g., drug product 312) may be expelled or withdrawn.

Movement of plunger rod 320 in the proximal or distal direction may translate, via pinions 328 and teeth 326, to proportionally smaller movement of plunger 360. In this manner, controlled movement of plunger 360 in the distal direction may, e.g., expel drug product 312 distally at a controlled rate. The sizes and shapes of the teeth, ratchets, and pinions in syringe 300 may be selected so as to create a desired controlled speed of movement of plunger 360.

Figure 11B:
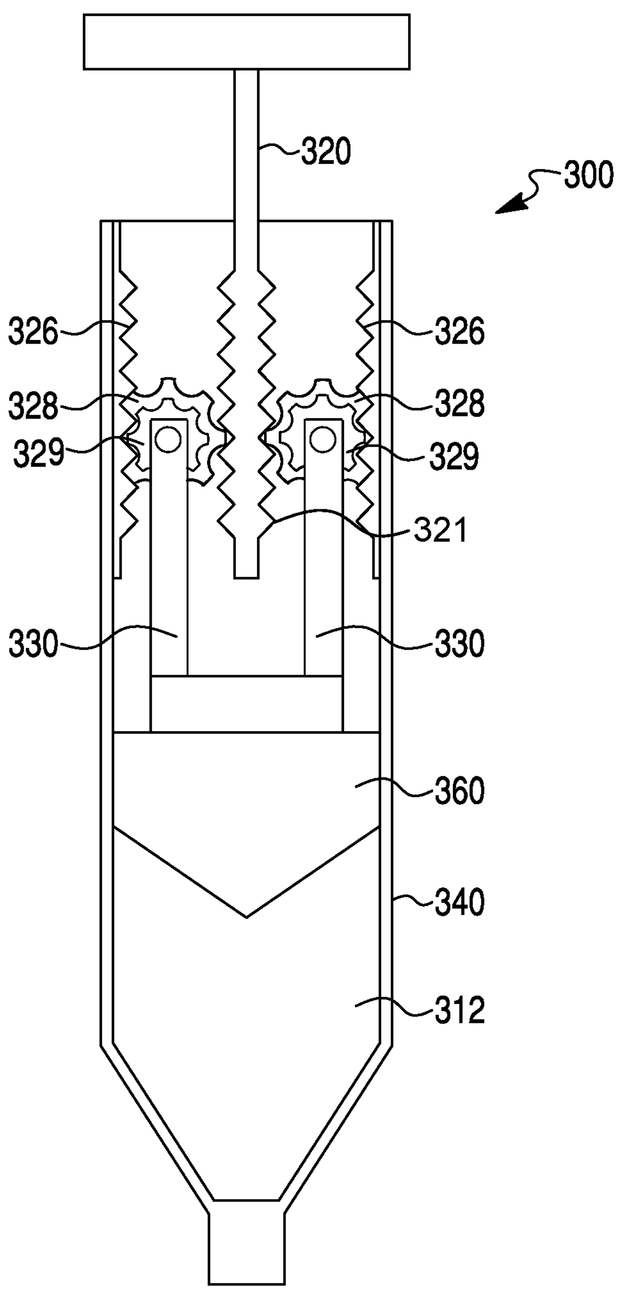

FIG. 11B depicts, in cross-section, a further embodiment of syringe 300, in which teeth 321 of plunger 320 may engage with pinions 328, which may each be coupled with, and may rotate coaxially and in tandem with, relatively smaller pinions 329, which in turn may engage with teeth 326 on the interior of barrel 340. Pinions 328 may pass adjacent to teeth 326, such that only pinions 329 engage with teeth 326. Each of pinions 328, 329 may be coupled to one of rods 330, which may be coupled to plunger 360.

Due to the relatively smaller diameter of pinions 329 as compared to pinions 328, movement of plunger 320 in the proximal or distal direction may translate, via pinions 328, pinions 329, and teeth 326, to proportionally smaller movement of plunger 360. In this manner, controlled movement of plunger 360 in the distal direction may, e.g., translate to relatively smaller movement of plunger 360 and controlled expulsions of drug product 312 distally. As with FIG. 11A, the sizes and shapes of the teeth, ratchets, and pinions in syringe 300 may be selected so as to create a desired controlled speed of movement of plunger 360.

Although the embodiments depicted in FIGS. 11A and 11B each show a symmetrical arrangement including teeth 321 on two sides of plunger rod 321, two of pinions 328, two of pinions 329 (with respect to the embodiment of FIG. 11B), and two of rods 330, a single arrangement, e.g., teeth 321 engaged with one pinion 328, which may be coupled to one pinion 329 (with respect to the embodiment of FIG. 11B), which may be coupled to one rod 330, is also contemplated. One of ordinary skill in the art will understand that more or fewer pinions, and/or rods may be incorporated into embodiments of the present disclosure, to achieve controlled delivery of the contents of syringe 300.

Figure 12:
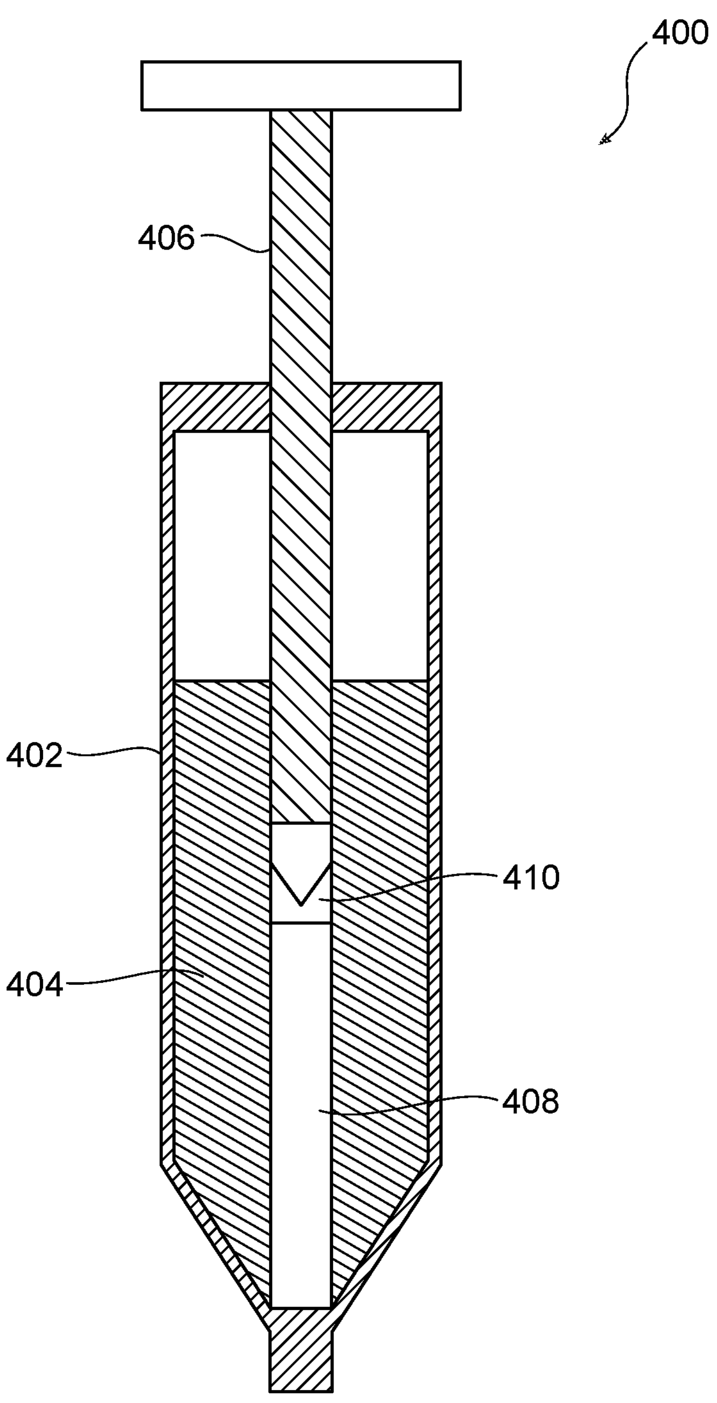
FIG. 12 depicts an exemplary delivery device according to additional embodiments of the present disclosure.

Referring now to FIG. 12, a cross-sectional side view of another syringe 400 is depicted with a further embodiment of a dose expel control mechanism. Syringe 400 may include a barrel 402, an inner sleeve 404, and a plunger rod 406. Plunger rod 406 may extend into barrel 402 and into an opening 410 defined by inner sleeve 404, where opening 410 is narrower than a general inner width of barrel 402. Opening 410 may receive or contain a drug product 408.

Generally, syringe 400 may be configured to provide a relatively narrow channel or path (e.g., in opening 10) through which drug product 408 may be pushed by plunger rod 406, such that distal movement by plunger rod 406 may be translated into relatively gradual and controllable expulsion or delivery of drug product 408 through a distal end of syringe 400 (e.g., via a needle, cannula, tube, or other attachment coupled to syringe 400), as compared to a syringe having a relatively wider channel or path for drug product 408.

As shown, a distal portion of plunger rod 406 may be configured to fit within opening 410 of inner sleeve 404. Inner sleeve 404 may be of a piece with barrel 402 (e.g., may be contiguous with, or may be made in a single mold with, barrel 402), or may be a separate piece inserted into barrel 402. Inner sleeve 404 may extend partly or fully through an interior of barrel 402. In some embodiments, as shown, inner sleeve 404 may be disposed in a distal portion of the interior of barrel 402.

Plunger rod 406 may be fitted with, coupled to, or may otherwise contact a plunger configured to enclose a volume of drug product 408 within opening 410 and/or between plunger rod 406 and a distal end of syringe 400. Plunger rod 406 and/or a plunger coupled to plunger rod 406 may be configured to fit snugly within barrel 402, so as to contain drug product 408 without leakage of drug product 408 into the general interior of barrel 402 (e.g., proximally from inner sleeve 404). Opening 410 and plunger rod 406 may be configured to have relatively narrow widths, thus creating the relatively narrow channel through which drug product 408 may be expelled from syringe 400.

In some embodiments, barrel 402 may be marked with measurement indicators, so as to visually indicate a volume of fluid left in, and/or dispensed from, syringe 400. Moreover, as shown or described with respect to other embodiments, syringe 400 may optionally include a magnifier attached to or embedded on syringe barrel 402, which may aid in reading measurement indicators on syringe barrel 102, may aid in observing the presence or absence of air bubbles in syringe barrel 102, and/or may aid in determining whether a complete dose of drug product 408 has been dispensed from syringe 400. Such a magnifier may be included in a distal region of syringe 10 and may be any suitable shape or size. In other embodiments, no magnifier 11 may be included.

In further embodiments, the narrow channel of syringe 400 may be achieved in a manner that does not require inner sleeve 400. For example, a syringe barrel (e.g., barrel 402) may be manufactured to itself have a relatively narrow interior configured to receive plunger rod 406, such that no narrowing insert need be disposed inside the barrel. The narrow interior of the syringe barrel may be sized and configured to house a volume of a drug product (e.g., drug product 408) that will result in a desired or suitable amount of the drug product being dispensed from syringe 400 upon its use.

Aspects of the embodiment depicted in FIG. 12 may be particularly suited to being combined with aspects of other embodiments discussed herein. For example, any embodiment of the present disclosure may also incorporate a relatively narrow (or narrowed) interior to allow for more gradual and controlled delivery of a drug product.

Figure 13C:
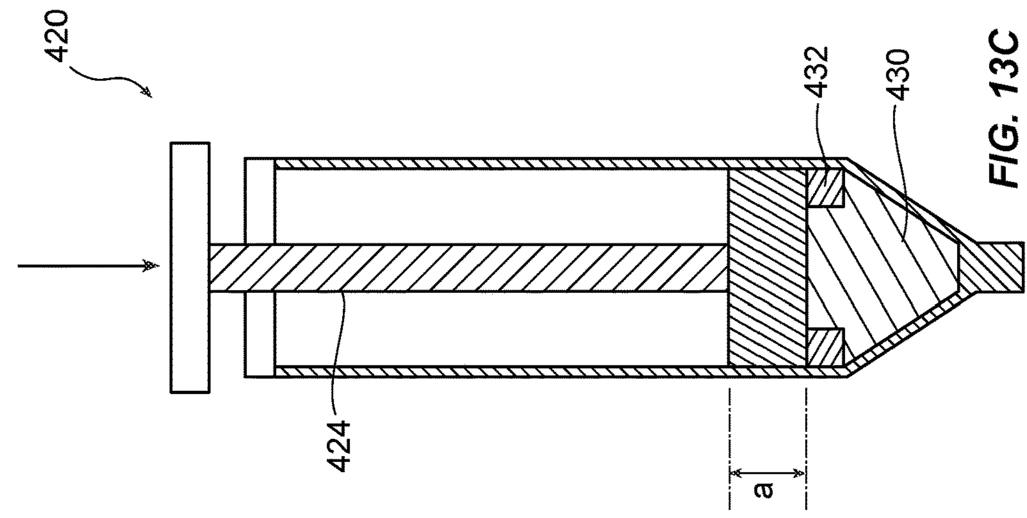
FIGS. 13A-13C depict an exemplary priming and delivery mechanism for a delivery device according to additional embodiments of the present disclosure.
Figure 13B:
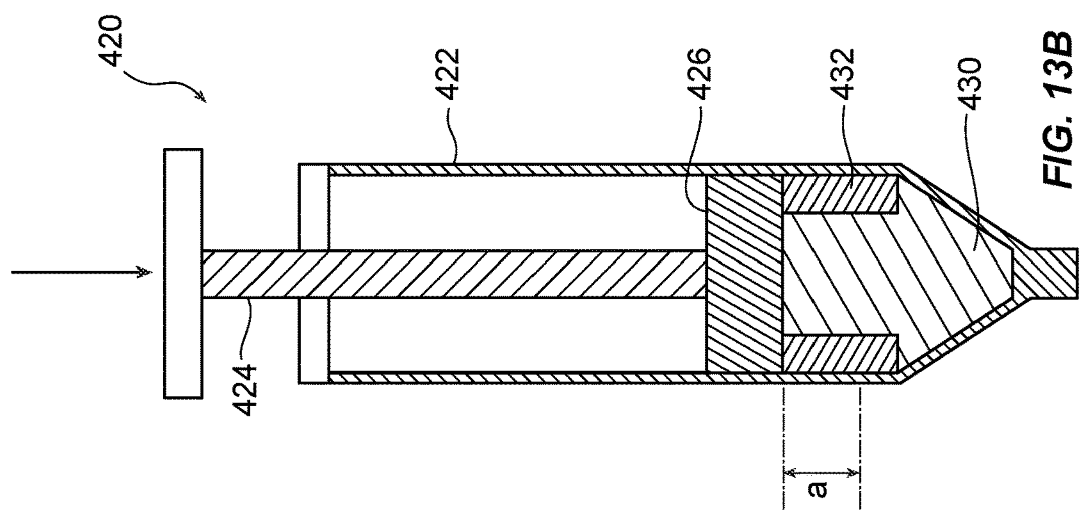
Figure 13A:
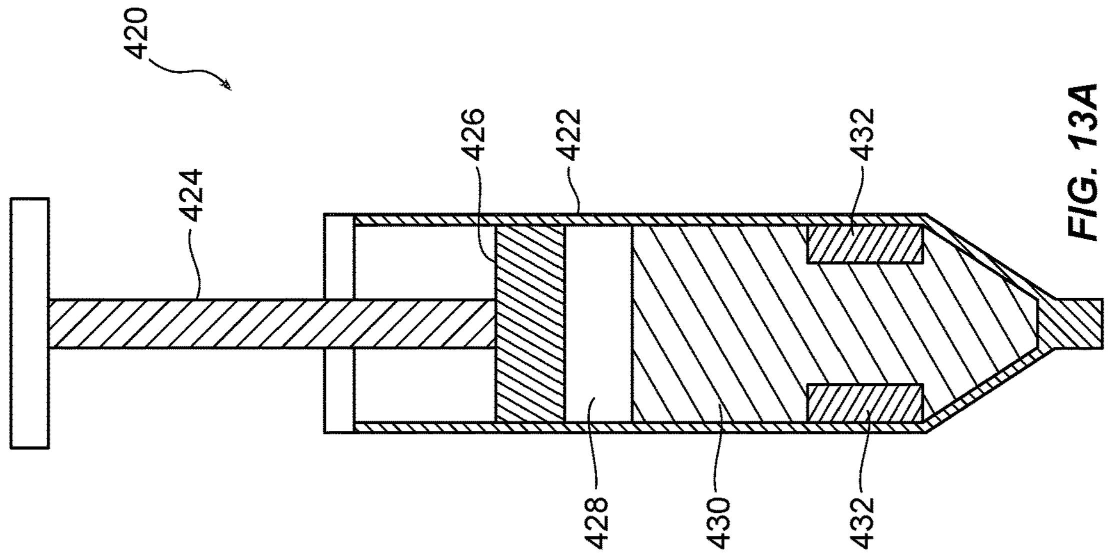

Referring now to FIGS. 13A-13C, cross-sectional side views of another syringe 420 are depicted, with a further embodiment of a dose expel control mechanism. Syringe 420 may include a barrel 422, a plunger rod 424, and a plunger 426. An interior 428 of barrel 422 may house or receive a drug product 430 and an insert 432.

Insert 432 may include a compressible portion, such that insert 432 may be compressed by a predetermined distance or volume. In some embodiments, for example, insert 432 may be a spring, such as a wave spring, a coiled spring, or any other spring known in the art. In further embodiments, for example, insert 432 may be made from a compressible material, such as rubber, silicone, or plastic. In some embodiments, insert 432 may be affixed to, or otherwise held in place within, a particular location/orientation in barrel 422.

An initial configuration of a filled syringe 420 is depicted in FIG. 13A. In this configuration, a quantity of drug product 430 is located between plunger 246 and insert 432, as is an empty space (e.g., an air bubble) in interior 428. As depicted in FIG. 13B, when plunger rod 424 is depressed distally, the quantity of drug product 430 between plunger 426 and insert 432 may be expelled distally from syringe 420, along with the air bubble (e.g., via a needle, cannula, tube, or other attachment coupled to a distal end of syringe 420). Upon contacting plunger 426, insert 432 may offer some resistance against further distal movement of 426. This may provide, e.g., a tactile, auditory, and/or visual feedback to a user of syringe 420 indicating that syringe 420 is primed and the air bubbles have been removed.

A distance a by which insert 432 may be compressed may be proportional to a volume of drug product 430 suitable for a dosage contained within barrel 422. For example, in some embodiments, a volume defined by insert 432 may correspond to a volume of drug product 430 suitable for a dosage contained within barrel 422. Thus, as shown in FIG. 13C, when plunger 426 is moved further distally so as to compress insert 432 by distance a, a quantity of drug product 430 suitable for a dosage may be dispensed from the distal end of syringe 420. For example, plunger 426 may be moved distally so that a volume of drug product 430 corresponding to the volume defined by insert 432 is dispensed. Insert 432 may be configured to prevent its compression or movement beyond distance a, thus ensuring that only a quantity of drug product 430 suitable for dosage is dispensed. A leftover quantity of drug product 430 may remain inside barrel 422 after a dosage amount is dispensed. In some cases, this may allow for increased dosage accuracy, as plunger 426 need not interact with any tapering of the diameter of barrel 422 that may occur near a distal end portion of syringe 420.

Figure 14C:
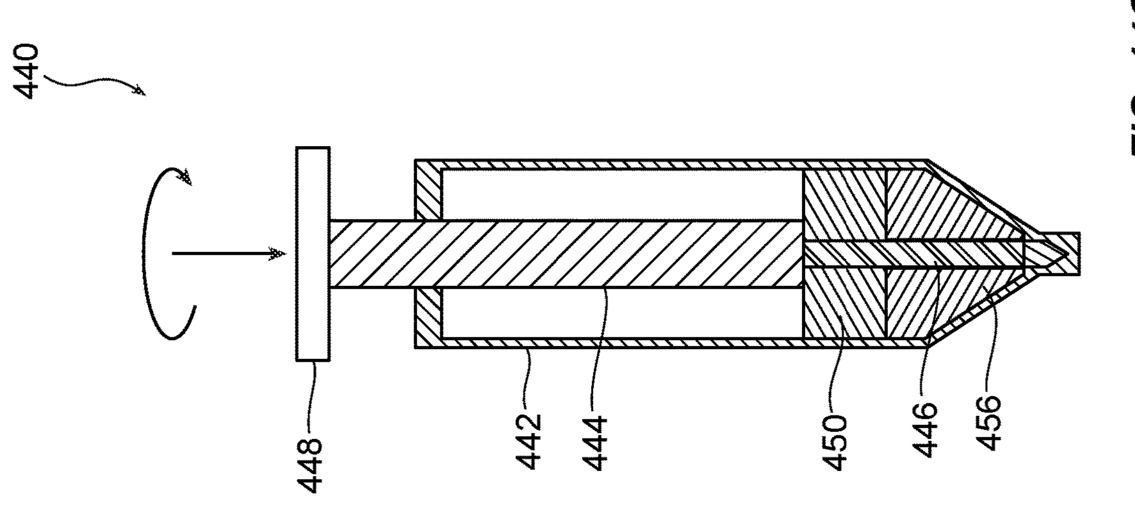
FIGS. 14A-14C depict another exemplary priming and delivery mechanism for a delivery device according to additional embodiments of the present disclosure.
Figure 14B:
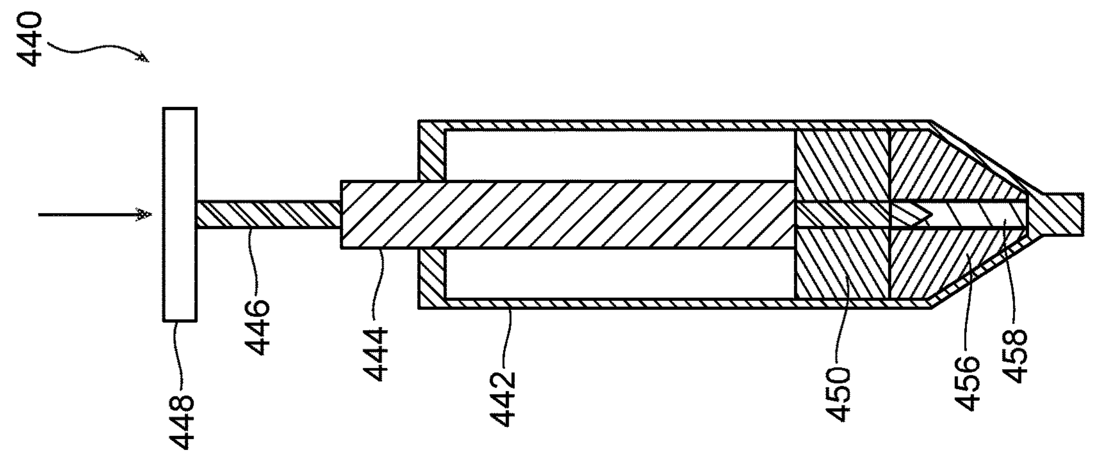
Figure 14A:
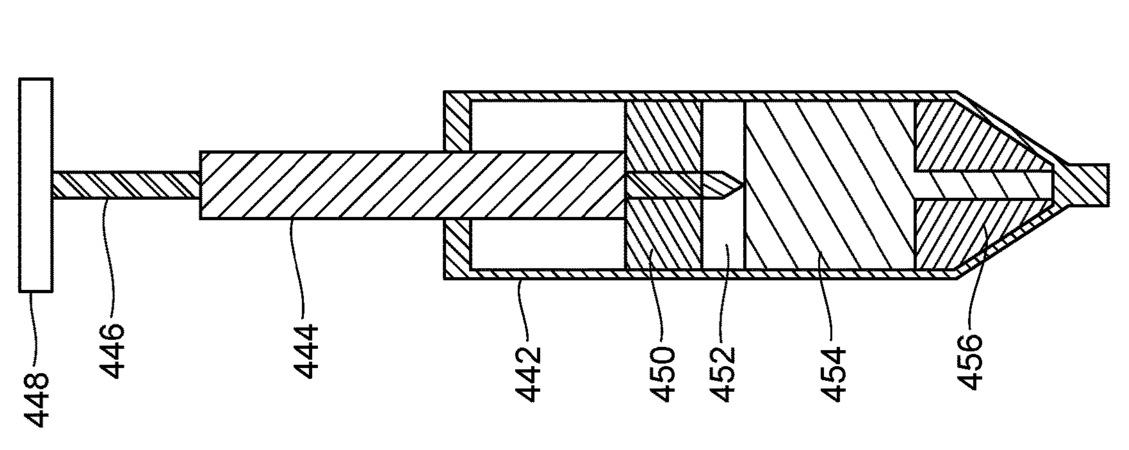

Referring now to FIGS. 14A-14C, cross-sectional side views of another syringe 440 with a further embodiment of a dose expel control mechanism are depicted in three stages. Syringe 440 may include a barrel 442, a plunger having an outer plunger rod 444 and an inner plunger rod 446, both of which may be actuated by a knob or depressor 448. Inner plunger rod 446 may be disposed inside, and coaxially with, outer plunger rod 444. Inner plunger rod may protrude proximally and/or distally from outer plunger rod 444. A plunger 450 may be coupled to either or both of inner plunger rod 446 and outer plunger rod 444. Specifically, plunger 450 may be movably coupled to inner plunger rod 446. A volume of drug product 454 may be received or housed within barrel 442 between plunger 450 and a distal end of syringe 440. An insert 456 may be disposed distally from plunger 450, e.g., at a distal end portion of the interior of barrel 442. Insert 456 may include a channel 458, sized and configured to accommodate inner plunger rod 446 (but not plunger 450 or outer plunger rod 444).

As shown in FIG. 14A, inner plunger rod 446 may protrude both proximally and distally from outer plunger rod 444. A seal (not shown) may exist between inner plunger rod 446 and outer plunger rod 444, to prevent leakage of any fluid between the plunger rods. In some embodiments, inner plunger rod 446 may only protrude distally or may only protrude proximally from outer plunger rod 444. For example, inner plunger rod 446 may be a telescoping plunger rod, which may be configured to extend only distally from outer plunger rod 444. In some embodiments, inner plunger rod 446 may be configured to optionally telescope, slide, or otherwise move through outer plunger rod 444 and plunger 450. In some embodiments, for example, inner plunger rod 446 may include a threaded portion on its exterior (not shown), configured to mate with complementary threads on an interior of outer plunger rod 444 (not shown). When inner plunger rod 446 and outer plunger rod 444 are engaged via these threads or by any other mechanism, inner plunger rod 446 and outer plunger rod 444 may move proximally and distally within barrel 442 in tandem. Upon rotation of inner plunger rod 446 (e.g., by turning knob or depressor 448) relative to outer plunger rod 444, inner plunger rod 446 may be configured or allowed to move proximally or distally independently of outer plunger rod 444, and in particular may be allowed to move distally through outer plunger rod 444 and plunger 450. In some embodiments, plunger 450 may be affixed to a distal end of outer plunger rod 444, so that inner plunger rod 446 may move through both outer plunger rod 444 and plunger 450 without causing separation between outer plunger rod 444 and plunger 450. In further embodiments, a distal end of outer plunger rod 444 may simply contact or press against plunger 450.

An initial configuration of syringe 440 is depicted in FIG. 14A. As shown, inner plunger rod 446, outer plunger rod 444, and plunger 450 are all located proximally from a volume of drug product 454 contained within barrel 442. As shown in FIG. 14B, upon depression of depressor or knob 448, both inner plunger rod 446 and outer plunger rod 444 may move distally through barrel 442, consequently pushing plunger 450 through barrel 442. This may serve to prime the syringe, removing air and an excess quantity of drug product 454 from barrel 442 by expelling it through, e.g., a distal end of barrel 442 (via, e.g., a needle, cannula, tube, or other attachment at the distal end of barrel 442). Distal movement of the plunger rods 444, 446 and plunger 450 may eventually be halted by contact between plunger 450 and insert 456. This may provide, e.g., a user with tactile, auditory, and/or visual feedback indicating that priming is complete.

As shown in FIG. 14C, inner plunger rod 446 may then be allowed to move distally independently from outer plunger rod 444, e.g., by rotation of inner plunger rod 446 such that inner plunger rod 446 disengages from outer plunger rod 444. Such rotation may, for example, cause threads on an exterior of inner plunger rod 446 to disengage from threads on an interior of outer plunger rod 444. In some embodiments, such rotation may allow for inner plunger rod 446 to expand (e.g., telescope) distally. Inner plunger rod 446 may then be moved distally through channel 458, which may contain a volume of drug product 454 suitable for a dosage amount. In this manner, inner plunger rod 446 may be configured to expel a desired dosage amount of drug product 454 through the distal end of barrel 442. In some embodiments, a distal end of inner plunger rod 446 may include, be attached to, or be affixed to an inner plunger, which may be sized and configured to move distally through channel 458, and push a volume of drug product 454 suitable for a dosage amount towards and through the distal end of barrel 442.

Referring now to FIGS. 15A-15E, views of another syringe 500 with a further embodiment of a dose expel control mechanism are depicted. Syringe 500 may include a barrel 502 and a plunger rod 503 having a knob or depressor 504 and projections 506, 508 which extend in directions that are offset from one another. Plunger rod 503 also includes a stopper 510. A proximal end of barrel 502 is capped by a keyhole-shaped flange 512 (a top-down view of which is depicted in FIG. 5E). Plunger 514 is disposed in an interior of barrel 502 such that it may be contacted and pushed distally by plunger rod 503. The interior of barrel 502 may also house a volume of a drug product 516 located distally from plunger 514.

Figures 15A, 15B, 15C:
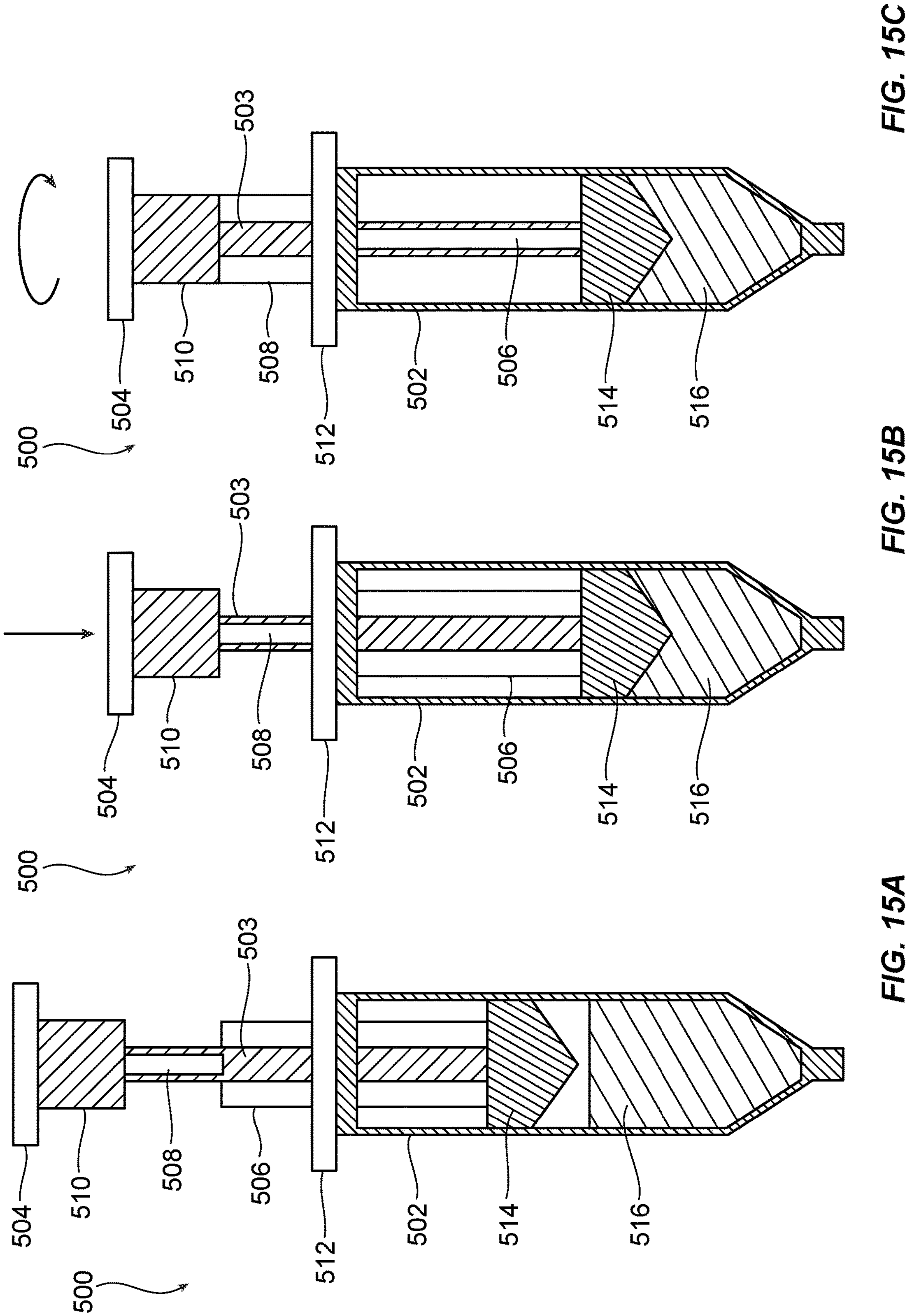
FIGS. 15A-15E depict another rotational lock mechanism for a delivery device according to additional embodiments of the present disclosure.
Figure 15E:
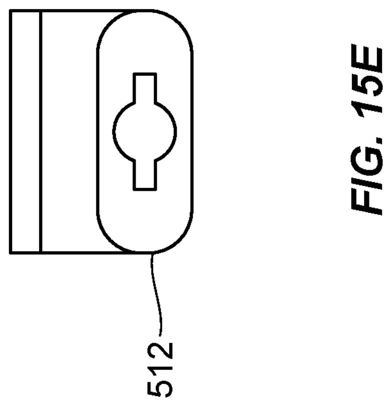

An initial configuration of syringe 500 is depicted in FIG. 15A. As shown, the plunger rod and plunger 514 are located proximally from the volume of drug product 516. Projections 506, which extend to a distal end portion of plunger rod 503, are positioned so as to fit through the keyhole shape in flange 512, allowing plunger rod 503 to move distally until flange 512 contacts projections 508 (FIG. 15B). The extent of the distal movement allowed in this configuration may be sufficient to prime syringe 500 and remove air between plunger 514 and drug product 516. As shown in FIG. 15B, plunger rod 503 may be prevented from moving further by the contact between flange 512 and projections 508, which may be of a similar shape and size to projections 506, but in a different configuration from projections 506 (e.g., a rotationally offset configuration).

Figure 15D:
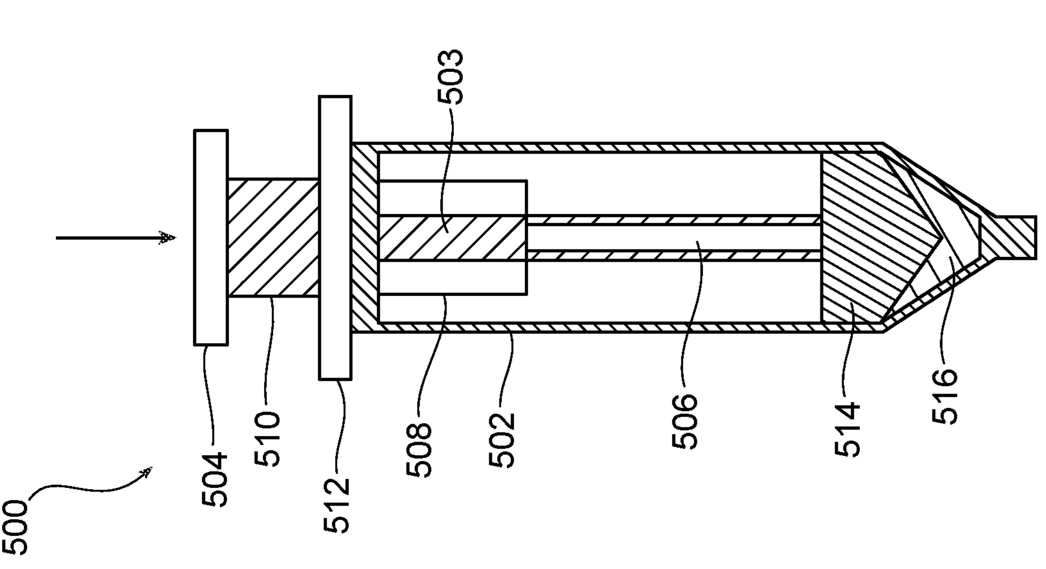

FIG. 15C depicts syringe 500 upon the rotation of plunger rod 503 by 90 degrees. In this configuration, projections 508 may now fit through flange 512, as shown in FIG. 15D. Plunger rod 503 may then move distally until its movement is stopped by stopper 510, which may have a shape and/or size that is not configured to fit through flange 512 in any orientation. Movement of plunger rod 503 as shown from FIG. 15C to FIG. 15D may dispense a volume of drug product 516 equivalent to a suitable or desired dose for a patient (e.g., by a needle, cannula, tube, or other attachment to the distal end of syringe 500). While plunger rod 503 is depicted as rotation 90 degrees between FIGS. 15C and 15D, it is understood that projections 506 and 508 may be rotationally offset by any suitable amount.

In some embodiments, as shown in FIG. 15D, upon dispensing the desired or suitable volume of drug product 516, plunger 514 may not be flush with a distal end of the interior of barrel 502 and a volume of drug product 516 may remain in barrel 502. In some embodiments, this may allow for increased accuracy in the volume of dose delivered from syringe 500, as discrepancies in size or shape between stopper 514 and the distal end of barrel 502 will not prevent the desired or suitable dose volume from being dispensed. Moreover, this (and other embodiments herein) may eliminate the need for a dose line on syringe 500, which may reduce or eliminate inaccuracies that may occur when placing a dose line on barrel 502 during manufacturing, and/or when visually gauging whether a volume of drug product 516 is aligned with a dose line on barrel 502.

It should be noted that while projections 506, 508 are depicted as having a particular shape and size, it is contemplated that they and the corresponding opening in flange 512 may have any suitable shape and size allowing for passage of projections 506, 508 through flange 512. Moreover, it should be noted that while an opening is being shown in flange 512, any suitably shaped opening may be incorporated in any part of syringe 500 suitable to regulate movement of plunger rod 503 (e.g., into a finger flange, a stopper fixed at a proximal end portion of barrel 502, a proximal side of barrel 502, or any other suitable portion of syringe 500).

Referring now to FIGS. 16A-16E, views of another syringe 600 with a further embodiment of a dose expel control mechanism are depicted. Syringe 600 may include a barrel 602 and a plunger rod 603 having a depressor 604 and a projection 606. A plunger 608 is disposed in an interior of barrel 602. A removable key 610 is disposed at a proximal end of barrel 602. The interior of barrel 602 may also house a volume of a drug product 612. A proximal end of barrel 602 may be closed or closed off in any suitable manner, having an opening configured to allow passage of the thin portion of plunger rod 603.

In some aspects of this embodiment, projection 606 may be sized and configured such that it is unable to pass beyond key 610. Thus, plunger rod 603 may only be depressed distally until projection 606 contacts key 610. Projection 606 may be affixed to plunger rod 603 in any suitable manner, or may be of a piece with (e.g., molded as a part of) plunger rod 603.

In some embodiments, key 610 may be made as a separate structure from other aspects of syringe 600. In further embodiments, key 610 may be of a piece with another component of syringe 600, such as, e.g., a removable finger flange (not shown).

Figure 16A:
Figure 16A:
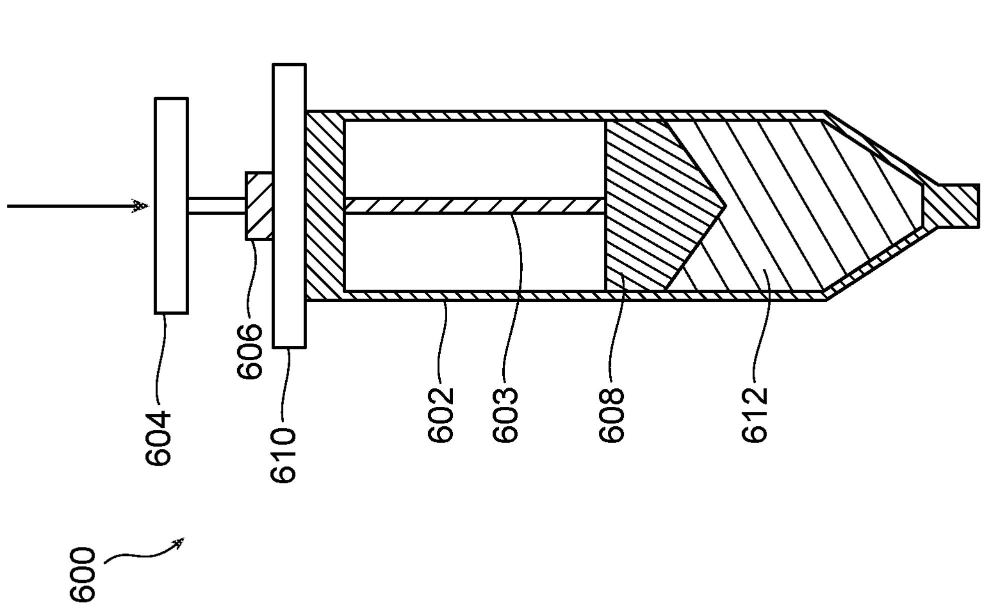
Figure 16A:
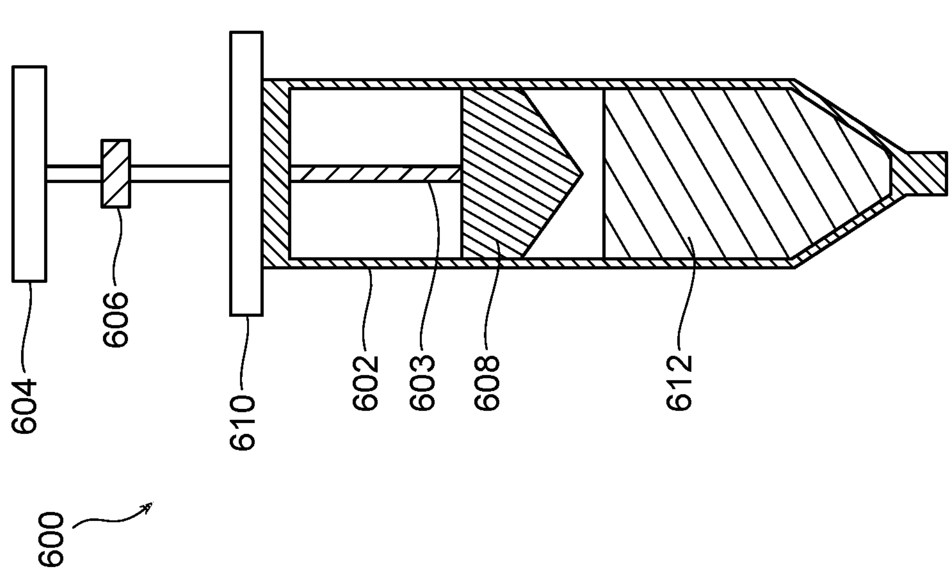

An initial configuration of syringe 600 is depicted in FIG. 16A. As shown, plunger rod 603 and plunger 608 are located proximally from the volume of drug product 612 disposed in the interior of barrel 602. Projection 606 is located a distance proximally from key 610. As shown in FIG. 16B, plunger rod 603 may be allowed to move distally (e.g., via depression of depressor 604) until projection 606 contacts key 610. The extent of the distal movement allowed in this configuration may be sufficient to prime syringe 600 and remove air between plunger 608 and drug product 612. As shown in FIG. 16B, plunger rod 603 may be prevented from moving further by the contact between key 610 and projection 606.

FIG. 16C depicts syringe 600 upon removal of key 610. A height of key 610 may be proportional to a desired or suitable dosage volume of drug product 612, such that once key 610 is removed, plunger rod 603 and projection 606 are free to move further distally until projection 606 contacts, and is obstructed by, a proximal end of barrel 602 (FIG. 16D) or other component of syringe 600 located at a distal end portion of barrel 602 (e.g., a flange, lid, or stopper). This movement of plunger rod 603 allows for plunger 608 to likewise expel a desired or suitable dosage volume of drug product 612 (e.g., via needle, cannula, tube, or other mechanism connected to a distal end of syringe 600).

Figures 17A, 17B, 17C:
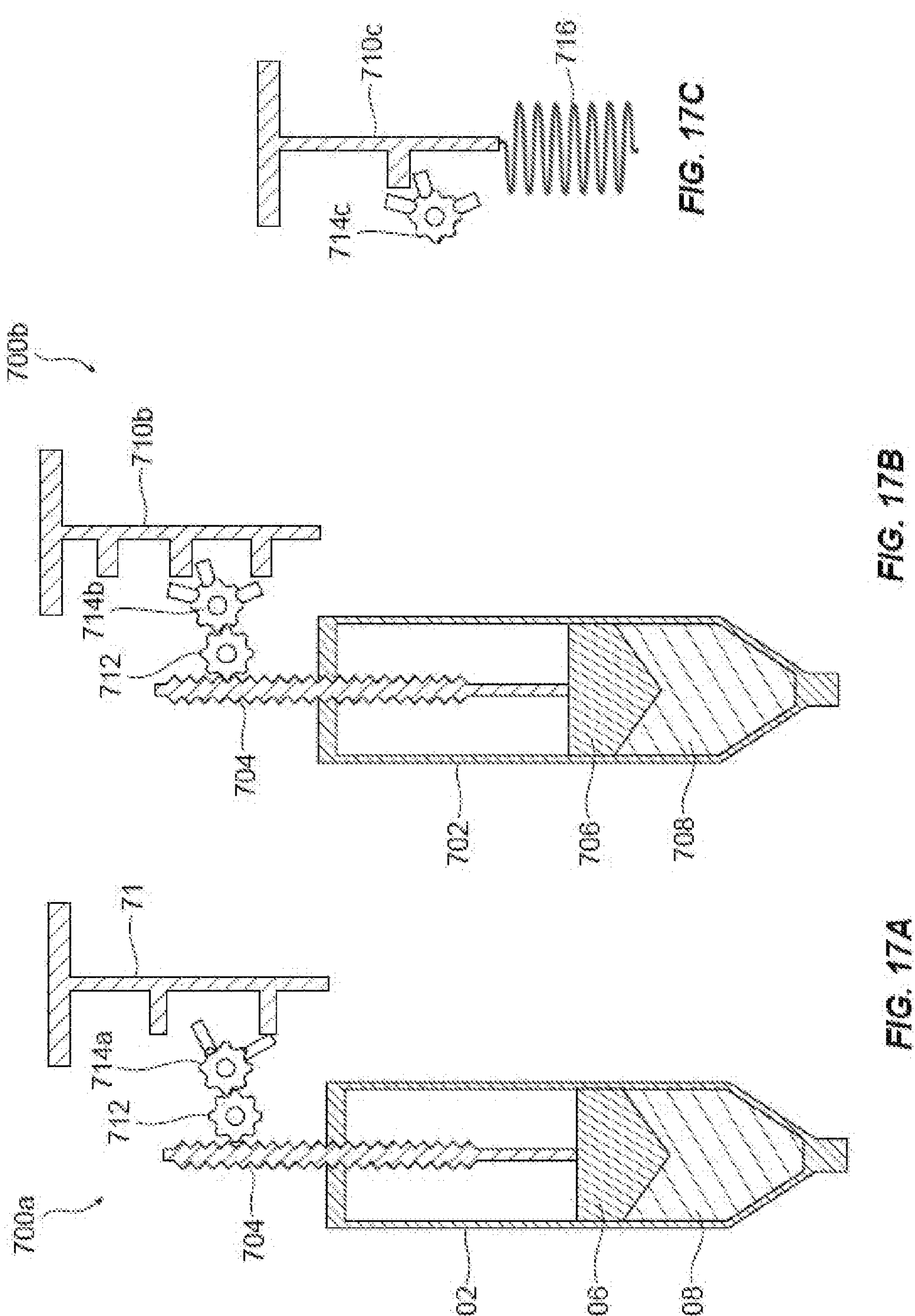
FIGS. 17A-17C depict further exemplary delivery devices and mechanisms according to additional embodiments of the present disclosure.

Referring now to FIGS. 17A-17B, two schematic views of additional embodiments of delivery devices with dose expel control mechanisms are depicted. FIG. 17A depicts a syringe 700*a*, having a body 702, a plunger rod 704 with a plurality of teeth, a plunger 706, and a volume of drug product 708. The teeth of plunger rod 704 may be configured to engage with complementary teeth on an intermediate gear 712, which may in turn be configured to engage with teeth on a driving gear 714*a*. Driving gear 714*a* is depicted with two longer teeth, which are configured to engage with tabs on an offset actuator 710*a*.

Priming and dispensing of a dose from syringe 700*a* may both be accomplished by depression of offset actuator 710*a* (e.g., to a first depressed position and a second depressed position). The tabs of offset actuator 710*a* may be sized and configured to interact with (e.g., push on) the long teeth of driving gear 714*a* at desired intervals corresponding to priming of syringe 700*a* (the lower tab and a first of the long teeth of driving gear 714*a* and dispensing of a desired dosage amount of drug product 708 (the upper tab of actuator 710*a* and a second of the long teeth of driving gear 714*a*. FIG. 17A depicts, for example, a position of driving gear 714*a* and actuator 710*a* after syringe 700*a* has been primed (e.g., a first depressed position). In some embodiments, driving gear 714*a*, intermediate gear 712, or plunger rod 704 may be configured to provide audio, visual, or tactile feedback upon movement of actuator 710*a* to a first or second depressed position (e.g., by providing a clicking sound, or by resisting movement beyond the depressed position). In some embodiments, the interaction between actuator 710*a* and driving gear 714*a* may resemble that of a Geneva drive. In some embodiments, rotation of driving gear 714*a* may be stopped by contact between a long tooth of driving gear 714*a* and intermediate gear 712.

Multiple configurations of a driving gear and an actuator are possible in order to achieve priming and/or drug dispensing steps by depression of the actuator. For example, FIG. 17B depicts a second syringe 700*b* with a driving gear 714*b* having three long teeth, instead of two, and an actuator 710*b* having three tabs, instead of two. In such an embodiment, it is contemplated that actuator 710*b* may be depressed multiple times (e.g., to a first depth, a second depth, and a third depth) to achieve a desired result (e.g., priming of syringe 700*b*). Each contact between a tab of actuator 710*b* and a long tooth of driving gear 714*b* may be accompanied by tactile, audio, or visual feedback, and may correspond with partially or fully priming syringe 700*b*, removing air bubbles from syringe 700*b*, or dispensing a desired dose volume from syringe 700*b*. In some embodiments, an actuator may have only one tab configured to interact with the long tooth or teeth of a driving gear (See, e.g., actuator 710*c* and driving gear 714*c* depicted in FIG. 17C).

In some embodiments, an actuator may be spring-loaded, such that after depressing the actuator to a predetermined extent (e.g., enough for a tab of the actuator to push, contact, rotate, and/or otherwise interact with a single long tooth of the driving gear), the actuator may be returned to its pre-depressed location by, e.g., a spring return or other return mechanism. Such an embodiment is schematically depicted in FIG. 17C, where depression of actuator 710*c* may compress spring 716, which may in turn cause actuator 710*c* to return to its pre-depressed location upon release. When actuator 710*c* is depressed again to a predetermined extent, the tab on actuator 710*c* may push, contact, rotate, and/or otherwise interact with another single long tooth of the driving gear. Each depression of the actuator may serve a separate function (e.g., to prime and/or remove air from a syringe, or to dispense a suitable dosage volume from a syringe).

While FIGS. 17A-17C depict potential versions of embodiments including a driving gear and an actuator, many more permutations and combinations of driving gears having longer teeth and actuators having tabs are contemplated. Additional variations on these embodiments include that the actuator (e.g., actuator 710*c*) may be spring-loaded or otherwise configured in any suitable manner to return to an initial position after, e.g., completing a priming or dispensing step.

Figures 18A, 18B, 18C:
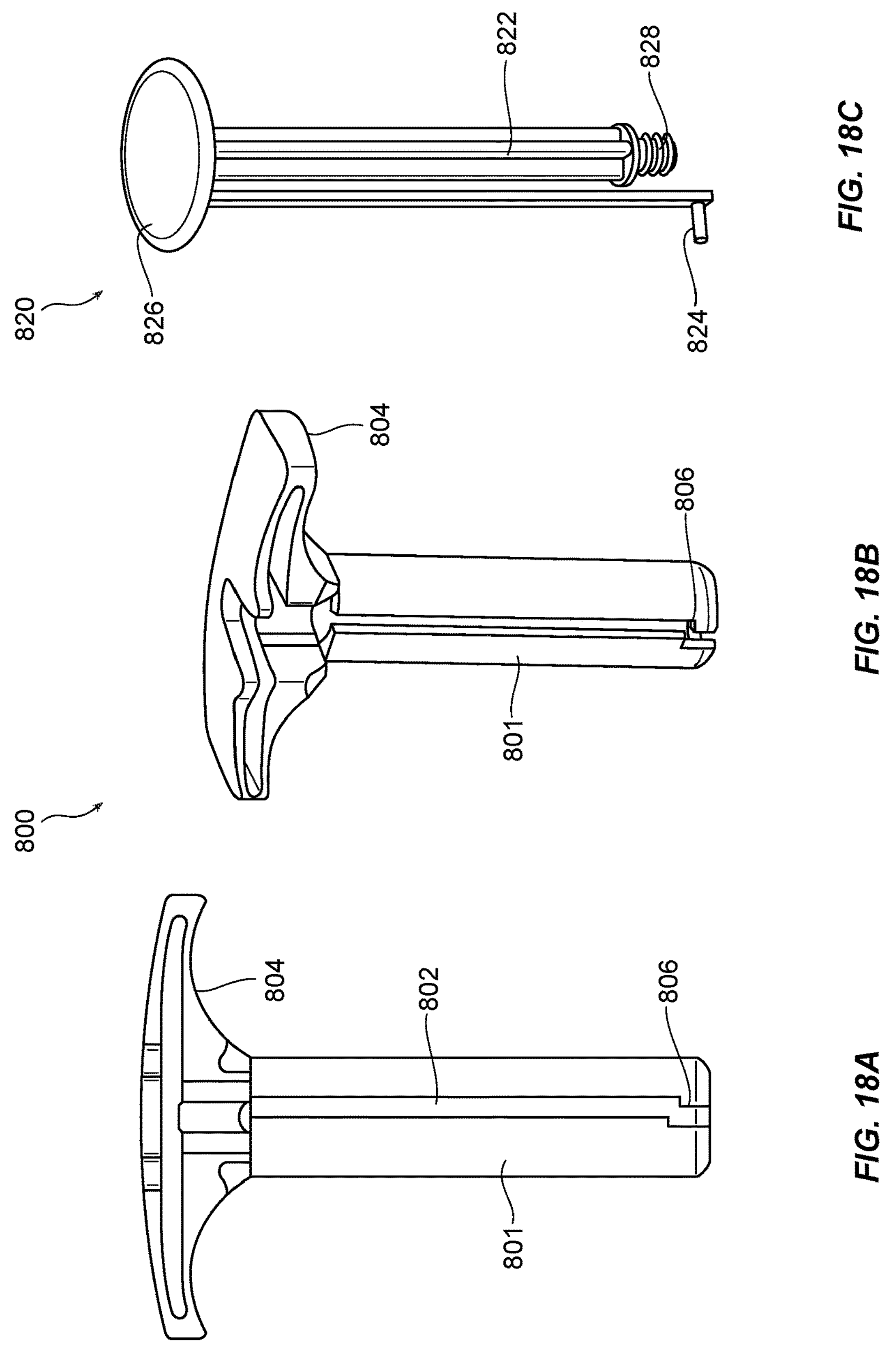
FIGS. 18A-18F depict a locking and priming mechanism for a delivery device according to additional embodiments of the present disclosure.

Referring now to FIGS. 18A-18F, views of another embodiment of a dose expel control mechanism are depicted. FIGS. 18A and 18B depict a front view and an angled view, respectively, of a sleeve 800. Sleeve 800 may be configured to surround and/or attach to, e.g., a syringe barrel, and may include a body 801, a channel 802, a flange 804, and an offset portion 806 of channel 802. Sleeve 800 may be configured to be used in conjunction with a plunger rod 820, depicted in, e.g., FIG. 18C. Plunger rod 820 may include a primary body 822 extending from a cap 826. Primary body 822 may be configured to extend into a body of a syringe barrel. Plunger rod pin arm 824, which may extend from cap 826 separately from primary body 822, may be configured to extend adjacent to a syringe barrel into which primary body 822 is extending. Plunger rod end 828 may be configured to contact, affix to, or otherwise attach to a plunger (not shown).

Figures 18D, 18E, 18F:
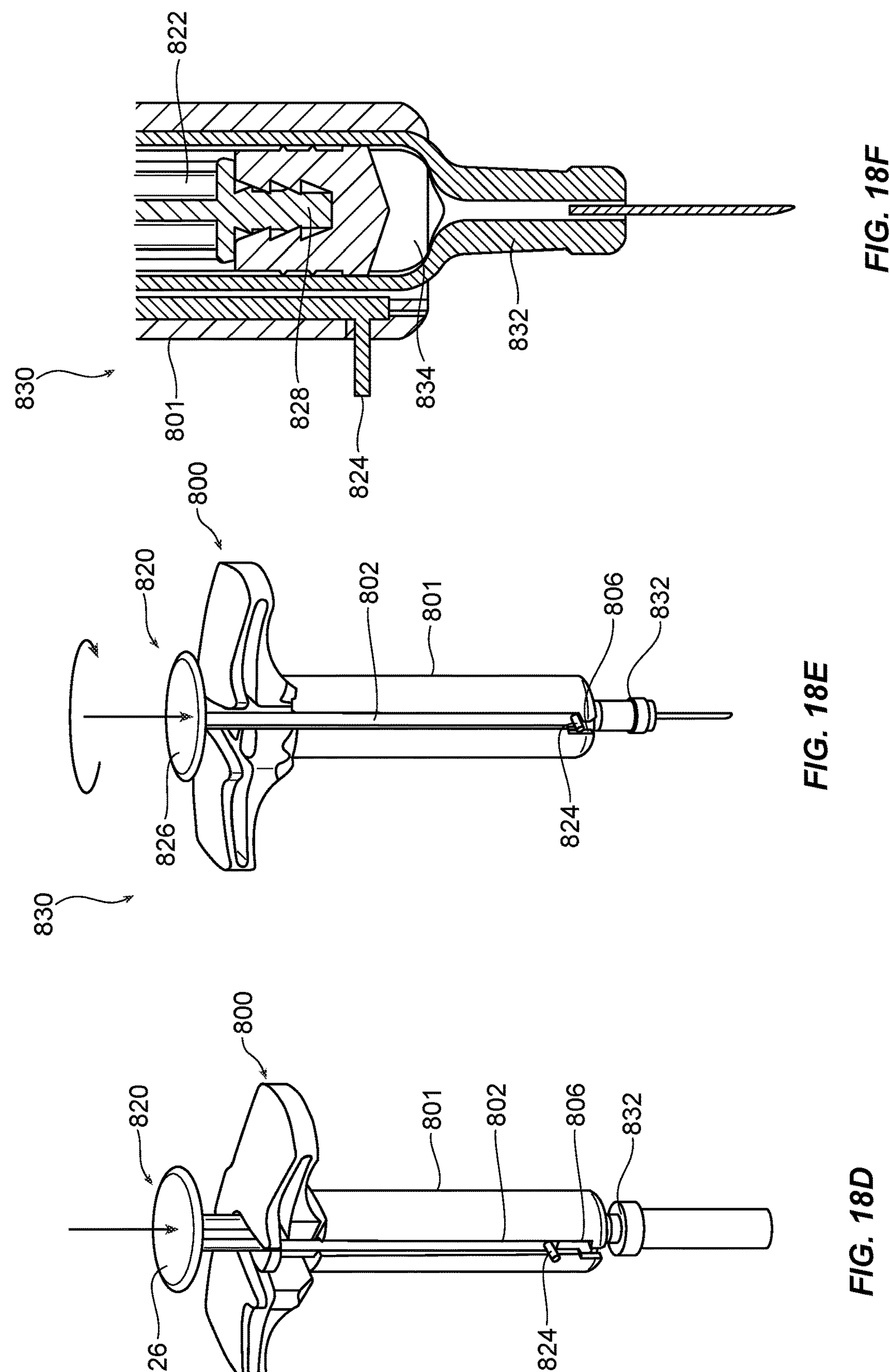

FIG. 18D depicts a syringe assembly 830 including sleeve 800 and plunger rod 820 surrounding a syringe 832. As shown, plunger rod pin arm 824 may be sized and configured to slide through channel 802. As plunger rod 820 is depressed distally into the body of syringe 832, plunger rod pin arm 824 may move distally through channel 802. When plunger rod pin arm 824 reaches the offset portion 806 of channel 802, the shape of channel 802 may stop further progress of plunger rod 820 distally. FIG. 18E depicts that, upon rotation of plunger rod 820 (e.g., turning of cap 826) or separate movement or rotation of plunger rod pin arm 824, plunger rod pin arm 824 may move laterally into offset portion 806 of channel 802, after which further distal movement of plunger rod pin arm 824, and thus plunger rod 820, may be possible.

Syringe 832 may include a volume of a drug product that may be greater than or equal to a desired dose for a patient. Initial distal movement of plunger rod 820 (e.g., prior to plunger rod pin arm 824 approaching offset portion 806 of channel 802) may be used to prime syringe 832. Contact of plunger rod pin arm 824 with the change in shape of channel 802 near offset portion 806 of channel 802 (shown in, e.g., FIG. 18E) may signify that the syringe is primed and that air has been removed from an interior of syringe 832. A length of offset portion 806 of channel 802 may be proportional to a desired dosage volume of a drug product inside syringe 832 after syringe 832 has been primed. Thus, rotation of plunger rod 820 to align plunger rod pin arm 824 with offset portion 806 of channel 802, and subsequent depression of plunger rod 802 such that plunger rod pin arm 824 slides through off set portion 806, may result in delivery of the desired dose of a drug product through the distal end of syringe 832 (depicted in, e.g., FIGS. 18E and 18F as being coupled to a needle).

FIG. 18F depicts a detail cross-sectional side view of assembly 830. Plunger rod pin arm 824 is shown as having contacted the portion of channel 802 where offset portion 806 begins. As such, assembly 830 may be in the "primed" position. The interior 834 of syringe 832 indicated in FIG. 18F may correspond to a desired dose volume of a drug product for delivery to a patient.

Referring now to FIGS. 19A-19E, views of another embodiment of a dose expel control mechanism are depicted. Assembly 900 may include a syringe body 902, a plunger rod 904*a*, a plunger 906, a plunger rod pin arm 908, and a sleeve 910*a*, which may be connected to a sleeve flange 912. Syringe body 902 may house a volume of drug product 914 located distally from plunger 906. Operation of this embodiment may be similar to operation of assembly 830 depicted in FIGS. 18A-18F. Notably, sleeve 910*a* need not extend along a full length of syringe body 902, allowing for visibility of syringe body 902, or into syringe body 902 if syringe body 902 is transparent. A length of sleeve 910*a* (and/or other parts of assembly 900) may be chosen to, e.g., help with ease of handling of assembly 900.

As depicted in FIGS. 19A-D, various configurations of a sleeve and a channel in the sleeve may be used in conjunction with assembly 900, to allow for priming and dispensing of a desired dose of a drug product from assembly 900. For example, sleeve 910*a* depicted in FIG. 19A includes a channel 909*a* which does not extend through the entirety of sleeve 910*a*. In this embodiment, the upper portion of channel 909*a* may correspond to a distance that plunger rod pin arm 908, and thus that plunger rod 904*a*, may travel in order to prime assembly 900, and the offset lower portion of channel 909*a* may be proportional to a desired dosage volume of drug product 914 that may be dispensed from a distal end of assembly 900 by rotation and distal movement of plunger rod 904*a* until plunger rod pin arm 908 is stopped from further distal movement by the end of channel 909*a*. The closed end of channel 909*a* ensures that more than the desired dosage volume is not delivered, and may mitigate variance in, e.g., a desired dosage volume by preventing plunger 906 from moving distally into a tapered distal end portion of syringe body 902. Such variance may be caused by, e.g., variability in geometries of plunger 906 and syringe body 902.

Figure 19D:
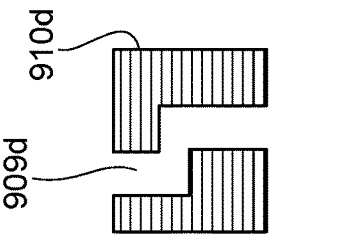
FIGS. 19A-19E depict another locking and priming mechanism for a delivery device according to additional embodiments of the present disclosure.
Figure 19C:
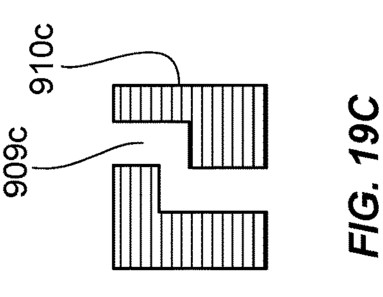
Figure 19E:
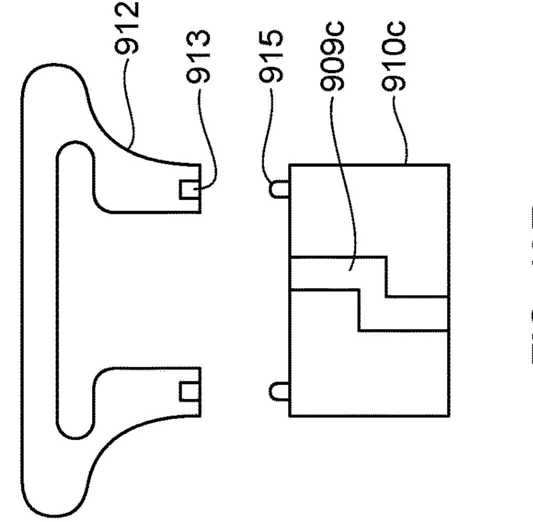
Figure 19B:
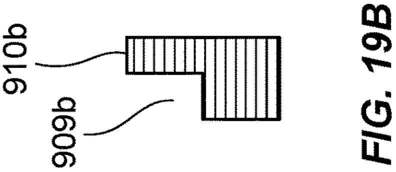
Figure 19A:
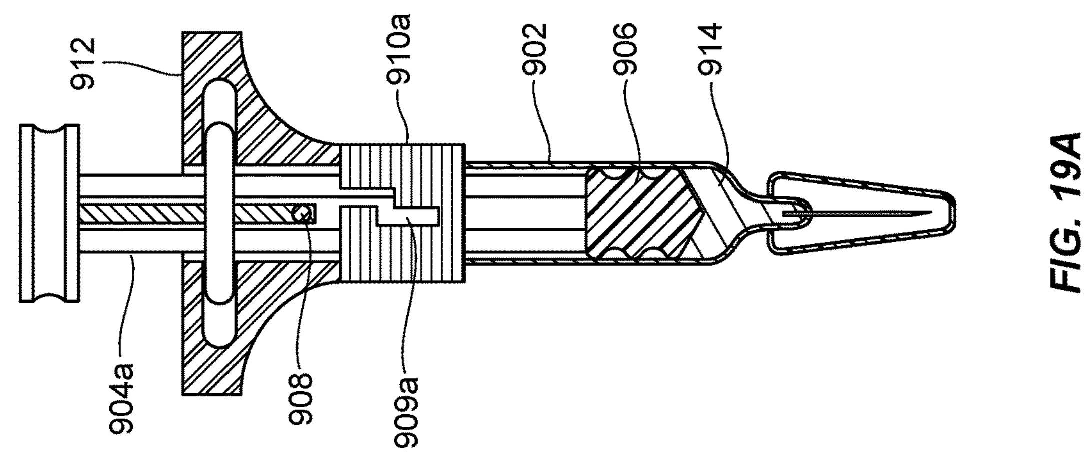

In alternative embodiments, the sleeve may have different configurations such as those depicted in FIGS. 19B-19D. Each of FIGS. 19B-19D depict a cross section of a sleeve having a variation of a channel through which plunger rod pin arm 908 may travel, thus guiding movement of plunger rod 904*a* within syringe body 902. For example, FIG. 19B depicts a front view of a half-sleeve 910*b*. Half-sleeve 910*b* may not wrap around syringe body 902 to create a narrow channel through which plunger rod pin arm 908 may travel; instead, plunger rod pin arm 908 may be guided by the "open" wall of half-sleeve 910*b*, and may travel in area 909*b* adjacent to the open wall of half-sleeve 910*b*. Sleeve 910*c*, depicted in FIG. 19C, provides a configuration similar to that of sleeve 910*a*, except for the open end of channel 909*c*, as opposed to the closed end of channel 909*a*. Such a configuration may allow for, e.g., bottoming out of plunger 906 in syringe body 902, in embodiments in which such bottoming out would allow for dispensing a desired dose of a drug product from assembly 900. Sleeve 910*d*, depicted in FIG. 19D, depicts a channel 909*d* having a bend in a direction opposite to the bend of sleeves 910*a*, 910*b*, and 910*c*.

FIGS. 19A-19D depict exemplary configurations of channels through which a plunger rod pin arm may travel. It is contemplated, however, that many more embodiments of sleeves and/or channels are possible. It is also contemplated that while channel 909*a* is depicted as being disposed distally from sleeve flange 912, a channel (e.g., channel 909*a*, 909*b*, 909*c*, or 909*d*) may be incorporated into a sleeve on or near any portion of a syringe body (e.g., syringe body 902), and/or may be incorporated into the syringe body itself (e.g., via embossing, engraving, molding, or other method).

FIG. 19E depicts sleeve 910C and an exemplary method or mechanism by which a sleeve (e.g., sleeve 910*c*) may connect to a flange portion 912 during assembly. As shown, sleeve 910*c* may include one or more tabs 915 that may interface with complementary slots, holes, or indents 913 in flange 912. The interface between tabs 915 and slots, holes, or indents 913 in flange 912 may be any suitable interface allowing for flange 912 and sleeve 910*c* to connect (e.g., a dovetail connection, a dowel connection, a mortise and tenon connection, or any other now-known or future-developed type of connection). In alternative embodiments, flange 912 may connect to sleeve 910*c* without the use of tabs, slots, holes, or indents (e.g., using an adhesive, a heat connection, etc.).

Attachment of the flange and sleeve in this manner may allow for one of the two components to be added to syringe body 902 first, followed by the other. For example, flange 912 may be configured to slide, surround, snap on, or otherwise combine with syringe body 902, and the sleeve (e.g., sleeve 910*a*, 910*b*, 910*c* or 910*d*) may subsequently be slid onto syringe body 902 and connected to flange 912. As a further example, the sleeve may be added to syringe body 902 first, followed by flange 912. In yet another example, the sleeve and flange 912 may first be connected, and then may slide, surround, snap on or otherwise combine with syringe body 902.

In further embodiments, a sleeve (e.g., sleeve 910*a*, 910*b*, 910*c* or 910*d*) and flange (e.g., flange 912) may be a unitary body (e.g., may be manufactured or molded together), instead of comprising two attached pieces. In some embodiments, the sleeve and/or flange may be made from, or may include, a material rigid enough to allow for a channel in the sleeve to restrict and/or control movement of a plunger rod pin arm, and flexible enough to allow for the sleeve and/or flange to snap onto or otherwise combine with syringe body 902. In some embodiments, for example, the sleeve and/or flange may include polypropylene. In some embodiments, for example, the sleeve and/or flange may include two different materials combined in an overmolding technique (e.g., polypropylene and a second material).

Figure 20C:
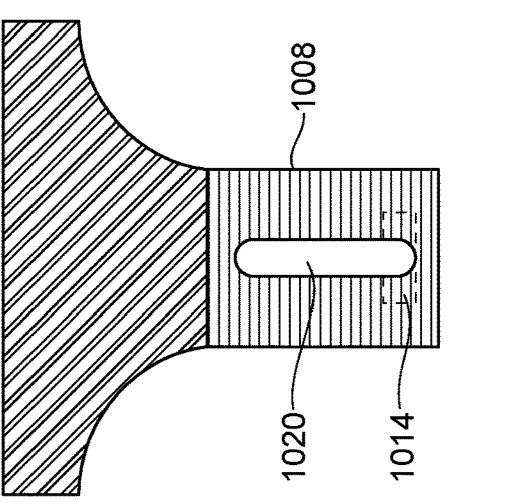
FIGS. 20A-20C depict another locking and priming mechanism for a delivery device according to additional embodiments of the present disclosure.
Figure 20C:
Figure 20B:
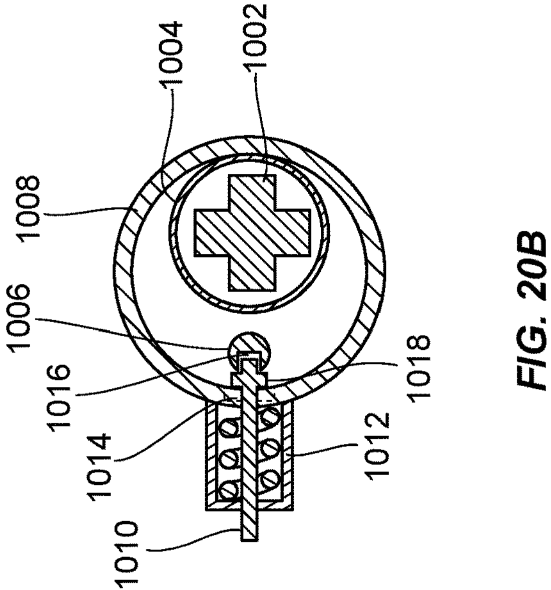
Figure 20A:
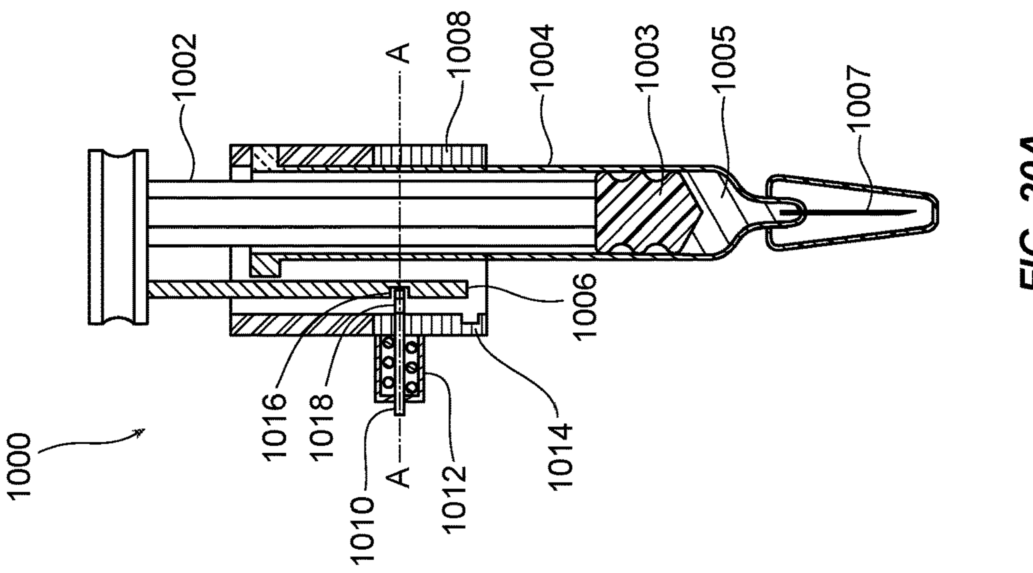
Figure 20A:

Referring now to FIGS. 20A-20C, views of another embodiment of a dose expel control mechanism are depicted. All three are discussed in tandem herein. As shown primarily in the cross-sectional side view of FIG. 20A and the cross section indicated by "A-A" depicted in FIG. 20B, assembly 1000 may include a plunger rod 1002, a plunger 1003, a syringe body 1004, a volume of a drug product 1005 disposed within syringe body 1004, a plunger rod arm 1006 configured to extend from the plunger rod cap separately from, and parallel to, plunger rod 1002, a sleeve 1008, a sleeve pin 1010, a spring-loaded pin casing 1012, a sleeve cavity 1014, a plunger rod arm cavity 1016, a pin protrusion 1018, and a sleeve pin slot 1020 (depicted in the view of sleeve 1008 shown in FIG. 20C).

As with the embodiments depicted in FIGS. 19A-19E, sleeve 1008 may include a flange, and may be configured to wrap around a circumference of syringe body 1004. Assembly 1000 differs from, e.g., assembly 900 in that plunger rod arm 1006 does not include a pin; instead, plunger rod arm 1006 may include a cavity 1016 into which sleeve pin 1010 may extend. Sleeve pin 1010 may be slidably connected to sleeve 1008 such that it extends through pin slot 1020. In some embodiments, pin casing 1012, which may be spring loaded, may exert a force on sleeve pin 1010 in a direction outward from sleeve 1008, while pin protrusion 1018 (depicted in, e.g., FIG. 20B) may prevent sleeve pin 1010 from being pulled out of pin slot 1020. In the configuration depicted in FIG. 20A, sleeve pin 1010 may be pushed distally (e.g., towards the expulsion end of assembly 1000) along the length of pin slot 1020 in order to move plunger rod arm 1006 distally (i.e., so that plunger rod 1002 also moves distally), because sleeve pin 1010 extends into plunger rod arm cavity 1016 (depicted in, e.g., FIG. 20B). This movement of sleeve pin 1010, and the corresponding movement of plunger rod 1002, may serve to prime assembly 1000.

Upon movement of sleeve pin 1010 to the distal end of pin slot 1020, pin protrusion 1018 may become aligned with sleeve cavity 1014, which may be sized and configured to house pin protrusion 1018. The force exerted upon sleeve pin 1010 by pin casing 1012 may cause pin protrusion 1018 to be pulled into sleeve cavity 1014, thus causing sleeve pin 1010 to disengage from plunger rod arm cavity 1016.

After sleeve pin 1010 has become disengaged from plunger rod arm cavity 1016, plunger rod 1002 may be pushed distally independently of sleeve pin 1010 (e.g., by a user) to dispense a desired dosage of drug product 1005.

With respect to any embodiment in the present disclosure that includes a sleeve and a pin that may travel through a channel or slot in the sleeve, it is contemplated that the channel or slot need not necessarily be located within a sleeve. For example, in embodiments where a sleeve wraps fully or partially around a syringe or syringe body, the sleeve may be replaced by, e.g., a channel or slot being imprinted, molded, or otherwise disposed directly upon the syringe or syringe body.

Features enumerated above have been described within the context of particular embodiments. However, features and aspects of the embodiments may be combined, added to other embodiments, subtracted from embodiments, etc. in any manner to assist with controlled preparation and/or delivery of a drug.

Aspects of the embodiments above have been described with respect to priming doses and removing excess air bubbles from within syringes. However, aspects of these embodiments may also be employed for use with fillable syringes and multi-dose vials. For example, syringes according to the present disclosure may provide a more precise method for transferring drug product from a vial to a syringe. Precision during this syringe loading step may reduce or minimize overfilling of syringes from, e.g., vials of drug product. Inhibiting overfilling may in turn decrease wastage of a drug product and may increase or maximize the number of doses that may be administered from one vial.

For example, to fill syringe 10 depicted in FIG. 1, dial 5 may be rotated in the reverse direction to withdraw piston 8 into syringe barrel 9 away from the distal needle end to fill syringe 10 through needle 13.

As a further example, to fill syringe 60 depicted in FIG. 5, plunger rod 61 may be rotated in the direction opposite to the direction needed to prime needle 66 to withdraw piston 68 into syringe barrel 69 away from the distal needle end to fill syringe 60 through needle 66.

While a number of embodiments are presented herein, multiple variations on such embodiments, and combinations of elements from one or more embodiments, are possible and are contemplated to be within the scope of the present disclosure. Moreover, those skilled in the art will appreciate that the conception upon which this disclosure is based may readily be used as a basis for designing other devices, methods, and systems for carrying out the several purposes of the present disclosure.

What is claimed is:

1. A drug delivery device comprising:

a barrel including a proximal end and a distal end;

a plunger rod extending into the barrel through an opening at the proximal end of the barrel, the plunger rod including a projection having a proximal portion and a distal portion; and a flange coupled to the proximal end of the barrel, the flange including a body, an opening with a circumference fully enclosed by the body, a channel, a first surface, and a second surface that is distal of the first surface, wherein the first surface and the second surface define interfaces for engaging the distal portion such that the body is only configured for two longitudinal and distally-directed strokes of the plunger rod that are inhibited by the flange;

wherein the distal portion of the projection is positioned external from the body of the flange prior to an initial stroke of the plunger rod;

wherein, after the initial stroke, the distal portion abuts the first surface such that the flange limits distal movement of the plunger rod, wherein, upon rotating the plunger rod about the central longitudinal axis, the flange allows distal movement of the distal portion of the projection relative to the channel to allow the plunger rod to move until the distal portion abuts the second surface, wherein the second surface defines a closed end of the channel, the flange is configured to inhibit distal movement and rotation of the plunger rod relative to the barrel when the distal portion of the projection is positioned against the closed end of the channel;

wherein the proximal portion of the projection is longitudinally spaced from the first surface when the distal portion abuts the second surface such that the proximal portion is positioned outside and proximal to the opening of the flange.

2. The drug delivery device of claim 1, wherein, prior to the initial stroke, the distal portion of the projection is spaced from the first surface of the flange by a priming distance.

3. The drug delivery device of claim 2, wherein the initial stroke includes advancing the plunger rod distally by the priming distance until the distal portion of the projection contacts the first surface of the flange.

4. The drug delivery device of claim 2, wherein upon moving the initial stroke and rotating the plunger rod about the central longitudinal axis and relative to the flange, the plunger rod is configured to move distally relative to the flange via a final stroke.

5. The drug delivery device of claim 4, wherein the projection is longitudinally aligned with the first surface and longitudinally misaligned with the second surface, in a direction parallel to the central longitudinal axis, upon the plunger rod moving the initial stroke and prior to rotating about the central longitudinal axis.

6. The drug delivery device of claim 4, wherein the projection is longitudinally aligned with the second surface and longitudinally misaligned with the first surface, in a direction parallel to the central longitudinal axis, upon rotating the plunger rod about the central longitudinal axis and moving along the final stroke.

7. The drug delivery device of claim 1, further comprising a plunger inside the barrel and in contact with the plunger rod;

wherein movement of the plunger rod via the initial stroke and the final stroke does not cause the plunger to contact the distal end of the barrel.

8. A drug delivery device comprising:

a barrel including a proximal end and a distal end;

a plunger rod extending into the barrel through an opening at the proximal end of the barrel and along a central longitudinal axis of the drug delivery device, the plunger rod including a projection having a proximal portion and a distal portion; and a flange coupled to the proximal end of the barrel, the flange including a body, a hole with a circumference fully enclosed by the body and a channel;

wherein the distal portion of the projection is longitudinally spaced apart from a first proximally-facing surface of the flange and positioned external from the flange prior to an initial stroke of the plunger rod;

wherein the flange at least partially defines a first path terminating at the first proximally-facing surface, such that the first proximally-facing surface abuts the distal portion after the plunger rod moves the initial stroke through the first path of the flange, wherein the channel is defined by a second proximally-facing surface that is longitudinally offset from the first proximally-facing surface, the channel is only configured for one stroke that is inhibited by the flange after the initial stroke that causes the distal portion to abut the first proximally-facing surface;

wherein the flange defines a second path at least partially defined by sidewalls of the channel, and terminating at the second proximally-facing surface, such that the second proximally-facing surface abuts the distal portion after the plunger rod moves a final stroke through the second path of the flange, the flange is configured to inhibit distal and rotational movement of the plunger rod relative to the barrel with the distal portion of the projection positioned against the second proximally-facing surface; and wherein the second proximally-facing surface is configured to receive the distal portion of the projection with the proximal portion of the projection positioned outside and proximal to the hole of the flange.

9. The drug delivery device of claim 8, wherein the body of the flange has a one-piece construction.

10. The drug delivery device of claim 8, wherein the flange is a finger flange and includes a sleeve defining the first proximally-facing surface and the second proximally-facing surface.

11. The drug delivery device of claim 10, wherein the sleeve is integral with the flange such that the finger flange and the sleeve are a unitary body.

12. The drug delivery device of claim 10, wherein the first proximally-facing surface is positioned proximal to, and laterally offset from, the second proximally-facing surface.

13. The drug delivery device of claim 8, wherein the projection is disposed about, and protrudes in a direction perpendicular to, the central longitudinal axis of the drug delivery device.

14. A method of preparing the drug delivery device of claim 8 for delivering a dose of a drug substance, the method comprising:

advancing the plunger rod distally into the barrel via the initial stroke until the distal portion abuts the first proximally-facing surface; and rotating the plunger rod about the central longitudinal axis, relative to the flange, until the distal portion no longer abuts the first proximally-facing surface.

15. The method of claim 14, the method further comprising:

advancing the plunger rod distally into the barrel via the final stroke until the distal portion abuts the second-proximally facing surface.

16. The method of claim 15, wherein advancing the plunger rod via the initial stroke primes the drug delivery device, and advancing the plunger rod via the final stroke delivers the dose of the drug substance from the drug delivery device.

17. A drug delivery device comprising:

a barrel including a proximal end and a distal end;

a plunger rod extending into the barrel, wherein the plunger rod includes a projection that has a proximal portion and a distal portion; and a flange coupled to the proximal end of the barrel, the flange including a body, an opening, a channel, a first surface, and a second surface that is distal of the first surface, the flange is configured to receive the plunger rod through the opening and the projection through the channel;

wherein, the body is only configured for a pair of distally-directed strokes of the plunger rod that are inhibited by the flange;

wherein, when:

the distal portion of the projection is longitudinally spaced from the first surface by a first distance corresponding to a first stroke of the pair of distally-directed strokes, the distal portion is not in longitudinal alignment with the second surface;

the distal portion of the projection contacts the first surface of the flange, the distal portion is not in longitudinal alignment with the second surface of the flange;

the distal portion of the projection is longitudinally spaced from the second surface by a second distance corresponding to a second stroke of the pair of distally-directed strokes, the distal portion is in longitudinal alignment with the second surface and not in longitudinal alignment with the first surface; and the distal portion of the projection contacts and is in longitudinal alignment with the second surface, the proximal portion of the projection is longitudinally spaced from the first surface and positioned proximal to the opening and outside the flange;

wherein the second surface defines a closed end of the channel, and the flange is configured to inhibit distal movement and rotation of the plunger rod relative to the barrel when the distal portion of the projection is positioned against the closed end of the channel.

18. The drug delivery device of claim 17, further comprising:

a plunger disposed inside the barrel and in contact with the plunger rod;

wherein, when the projection is in contact with the first surface and the second surface, the plunger is not flush with the distal end of the barrel.

19. The drug delivery device of claim 17, further comprising:

a plunger disposed inside the barrel and in contact with the plunger rod;

a first volume of drug product disposed in between the plunger and the distal end of the barrel prior to the plunger rod moving the first stroke;

a second volume of drug product disposed in between the plunger and the distal end of the barrel after the plunger rod moves the first stroke and prior to moving the second stroke, wherein the second volume of drug product is smaller than the first volume of drug product; and a third volume of drug product disposed in between the plunger and the distal end of the barrel after the plunger rod moves the second stroke, wherein the third volume of drug product is smaller than the second volume of drug product and greater than zero.

20. The drug delivery device of claim 17, wherein the first distance is less than the second distance, and the plunger rod is prevented from moving distally relative to the flange after the projection contacts the second surface.

* * * * *